US008486945B2

(12) United States Patent
Ivashchenko et al.

(10) Patent No.: US 8,486,945 B2
(45) Date of Patent: Jul. 16, 2013

(54) HETEROCYCLIC INHIBITORS OF AN HH-SIGNAL CASCADE, MEDICINAL COMPOSITIONS BASED THEREON AND METHODS FOR TREATING DISEASES CAUSED BY THE ABERRANT ACTIVITY OF AN HH-SIGNAL SYSTEM

(75) Inventors: Andrey Ivashchenko, Moscow (RU); Yan Lavrovsky, San Diego, CA (US); Sergey Malyarchuk, Carson City, NV (US); Ilya Okun, San Diego, CA (US); Nikolay Savchuk, Rancho Santa Fe, CA (US); Sergey Tkachenko, San Diego, CA (US); Alexander Khvat, San Diego, CA (US); Alexander Ivashchenko, Encinitas, CA (US)

(73) Assignees: Alexandre Vasilievich Ivachtchenko, Encinitas, CA (US); Andrey Alexandrovich Ivashchenko, Moscow (RU); Nikolay Filippovich Savchuk, Rancho Sante Fe, CA (US)

( * ) Notice: Subject to any disclaimer, the term of this patent is extended or adjusted under 35 U.S.C. 154(b) by 62 days.

(21) Appl. No.: 12/808,152

(22) PCT Filed: Dec. 12, 2008

(86) PCT No.: PCT/IB2008/055258
§ 371 (c)(1),
(2), (4) Date: Nov. 19, 2010

(87) PCT Pub. No.: WO2009/077956
PCT Pub. Date: Jun. 25, 2009

(65) Prior Publication Data
US 2011/0053915 A1    Mar. 3, 2011

(30) Foreign Application Priority Data
Dec. 14, 2007  (RU) ................ 2007146270

(51) Int. Cl.
*A01N 43/58*    (2006.01)
*A61K 31/50*    (2006.01)
*C07D 487/00*   (2006.01)

(52) U.S. Cl.
USPC ......................................... 514/250; 544/236

(58) Field of Classification Search
USPC .......................................... 544/236; 514/250
See application file for complete search history.

(56) References Cited

U.S. PATENT DOCUMENTS
2009/0093415 A1    4/2009  Yamano

FOREIGN PATENT DOCUMENTS
| EP | 1872795 | 1/2008 |
| JP | 61-056180 | 3/1986 |
| JP | 04-191736 | 7/1992 |
| WO | WO2004/011430 | 2/2004 |
| WO | WO2004/069149 | 8/2004 |
| WO | WO2004/072025 | 8/2004 |
| WO | WO2006/115135 | 11/2006 |
| WO | WO2007/019344 | 2/2007 |
| WO | WO2007/019346 | 2/2007 |
| WO | WO2007/064902 | 6/2007 |
| WO | WO2007/087066 | 8/2007 |
| WO | WO2007/117465 | 10/2007 |
| WO | WO2007/124345 | 11/2007 |

OTHER PUBLICATIONS

Pinedo et al McMahon et al.*
DB Registry ACS on STN (online) Reg. No. 898499-62-2, publ. Aug. 3, 2006.
DB Registry ACS on STN (online) Reg. No. 537021-10-6, publ. Jun. 25, 2003.
DB Registry ACS on STN (online) Reg. No. 864936-53-8, publ. Oct. 11, 2005.
DB Registry ACS on STN (online) Reg. No. 923677-65-0, publ. Feb. 27, 2007.
DB Registry ACS on STN (online) Reg. No. 923676-65-7, publ. Feb. 28, 2007.
DB Registry ACS on STN (online) Reg. No. 923165-94-0, publ. Feb. 26, 2007.
DB Registry ACS on STN (online) Reg. No. 923174-45-2, publ. Feb. 26, 2007.
DB Registry ACS on STN (online) Reg. No. 923165-68-8, publ. Feb. 26, 2007.
DB Registry ACS on STN (online) Reg. No. 863020-32-0, publ. Sep. 13, 2005.
DB Registry ACS on STN (online) Reg. No. 862811-49-2, publ. Sep. 9, 2005.

(Continued)

*Primary Examiner* — Paul V. Ward
(74) *Attorney, Agent, or Firm* — Sughrue Mion, PLLC

(57) ABSTRACT

The invention relates to novel heterocyclic compounds and to the use thereof, to pharmaceutical compositions containing said chemical compounds as an active ingredient and to the use thereof for producing medicinal preparations for the human being and warm-blood animals for treating diseases caused by the aberrant activity of an Hedgehog (Hh)-signal system, in particular oncological diseases. The invention also relates to the use of the above-mentioned compounds in the form of 'molecular pharmacological tools' for examining (in vitro and in vivo) the biochemical features of the Hh-signal system, in particular, the interaction of Hh protein and transmembrane proteins, namely, suppressor Patched (Ptc) and protooncogenic proteins. The eight groups of the claimed compounds comprise the derivatives of 2,6-dihydro-7H-pyrazolo[3,4-d]pyridazine-7-one and 1,4-dihydropyrazolo[3,4-b][1,4]thiazine-5-one; N-acidylated 4-imidazo[1,2-a]pyrimidine-2-il-anilines; ([4H-thino[3,2-b]pyrrol-5-il)carbonyl]piperidine-4-carbonic acid amides; 2-(4carbomoilpyperidine-1-il)-isonicotinic acid amides; N-sylphonyl-1,2,3,4-tetrahydroquinoline-6-carbonic acid amides; and pyridine 2-amino-4,5,6,7-tetrahydrothieno[2,3-c]N-acidylated 3-azole derivatives.

5 Claims, 2 Drawing Sheets

OTHER PUBLICATIONS

Figure 1:
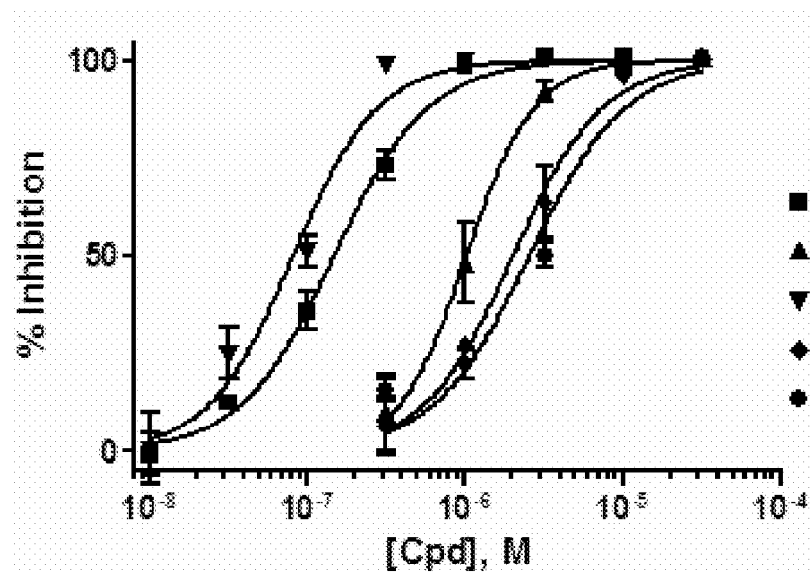

DB Registry ACS on STN (online) Reg. No. 862811-35-6, publ.Sep. 9, 2005.
DB Registry ACS on STN (online) Reg. No. 862811-39-0, publ. Sep. 9, 2005.
DB Registry ACS on STN (online) Reg. No. 862810-08-0.
DB Registry ACS on STN (online) Reg. No. 847387-45-5, publ. Mar. 28, 2005.
DB Registry ACS on STN (online) Reg. No. 862811-00-5, publ.Sep. 9, 2005.
DB Registry ACS on STN (online) Reg. No. 862810-82-0, publ.Sep. 9, 2005).
DB Registry ACS on STN (online) Reg. No. 902896-61-1P.
DB Registry ACS on STN (online) Reg. No. 902896-69-9P.
DB Registry ACS on STN (online) Reg. No. 902896-77-9P.
DB Registry ACS on STN (online) Reg. No. 902896-90-6P.
DB Registry ACS on STN (online) Reg. No. 902897-26-1P.
DB Registry ACS on STN (online) Reg. No. 902896-87-1.
DB Registry ACS on STN (online) Reg. No. 902899-39-2P.
DB Registry ACS on STN (online) Reg. No. 902900-28-1P.
Aparicio A.L.M., et al., Prostate cancer and Hedgehog signalling pathway. *Clin. Transl. Oncol.* 2007; 9(7): 420-8.
Berman D.M., et al., Medulloblastoma growth inhibition by hedgehog pathway blockade. *Science.* 2002; 297(5586): 1559-61.
Claret S., et al., Evidence for a novel feedback loop in the Hedgehog pathway involving Smoothened and Fused. *Cur. Biol.* 2007; 17(15): 1326-33.
Evangelista M., et al., The hedgehog signalling pathway in cancer. *Clin. Cancer Res.* 2006; 12(20 Pt 1):5924-8.
Frank-Kamenetsky M.,et al., Small-molecule modulators of Hedgehog signaling: Identification and characterization of smoothened agonists and antagonists. *J. Biol.* 2002; 1(2): 10.
Ilyin, Alexey P., et al,."Synthesis of heterocyclic compounds possessing the 4H-Thieno [3,2-b] Pyrrole Moiety", J. of Combinatorial Chemistry, 2007, 9(1), 96-106 [online] DB ACS on STN, CA 146:229308.
Kinto N., et al., Fibroblasts expressing Sonic hedgehog induce osteoblast differentiation and ectopic bone formation. *FEBS Lett.* 1997; 404(2-3): 319-23.
Kiselyov A.S., et al., Small-molecule modulators of Hh and Wnt signaling pathways. *Expert Opin. Ther. Targets.* 2007; 11(8): 1087-1101.
Kubo M., et al., Hedgehog signaling pathway is a new therapeutic target for patients with breast cancer. *Cancer Research.* 2004; 64(17): 6071-6074.
Lewis M.T., et al., The hedgehog signaling network, mammary stem cells, and breast cancer: connections and controversies. *Ernst. Schering Found. Symp. Proc.* 2006; 5:181-21.
Meth M.J., et al., Cyclopamine: inhibiting hedgehog in the treatment of psoriasis. *Cutis.* 2006; 78(3):185-8.
Neumann C.J. Hedgehogs as negative regulators of the cell cycle. *Cell Cycle.* 2005; 4(9):1139-40.
Ogden S.K., et al., Regulation of Hedgehog signaling: a complex story. *Biochem. Pharmacol.* 2004; 67(5):805-14.
Park H.L., et al., Mouse Gli1 mutants are viable but have defects in SHH signaling in combination with a Gli2 mutation. *Development.* 2000 127(8): 1593-605.
Pepinsky R.B.,et al., Identification of a palmitic acid-modified form of human Sonic hedgehog. *J. Biol. Chem.* 1998; 273: 14037-45.
Porter J.A., et al., Cholesterol modification of hedgehog signalling proteins in animal development. *Science.* 1996; 274: 1597.
Spinella-Jaegle S., et al., Sonic hedgehog increases the commitment of pluripotent mesenchymal cells into the osteoblastic lineage and abolishes adipocytic differentiation. *J. Cell Sci.* 2001; 114(Pt 11): 2085-94.
Taipale J., et al., Effects of oncogenic mutations in Smoothened and Patched can be reversed by cyclopamine. *Nature.* 2000; 406(6799): 1005-9.
Williams J.A. Hedgehog signaling pathway as a target for therapeutic intervention in basal cell carcinoma. *Drug News Perspect.* 2003; 16(10): 657-62.
Williams J.A., et al., Identification of a small molecule inhibitor of the hedgehog signalling pathway: effects on basal cell carcinoma-like lesions. *Proc. Natl. Acad. Sci.* 2003; 100(8): 4616-21.

\* cited by examiner

HETEROCYCLIC INHIBITORS OF AN HH-SIGNAL CASCADE, MEDICINAL COMPOSITIONS BASED THEREON AND METHODS FOR TREATING DISEASES CAUSED BY THE ABERRANT ACTIVITY OF AN HH-SIGNAL SYSTEM

CROSS REFERENCE TO RELATED APPLICATIONS

This application is a 35 U.S.C. §371 National Stage application of International Application No. PCT/IB2008/055258, filed Dec. 12, 2008, which claims the benefit under 35 U.S.C. §119(a) to Russian Patent Application No. 2007146270, filed Dec. 14, 2007. The disclosure of each of the prior applications is considered part of and is incorporated by reference in the disclosure of this application.

FIELD OF THE INVENTION

The invention relates to the eight groups of novel heterocyclic compounds and their use, and to pharmaceutical compositions comprising the said chemical compounds as active ingredients, to their use for medicament preparations for humans and warm-blooded animals, suitable for treatment diseases associated with aberrant activity of Hedgehog (Hh) signalling system, in particular, oncological diseases. The invention also relates to the use of the said compounds as "molecular pharmacological tools" for investigation (in vitro and in vivo) of biochemical peculiarities of Hh signalling system, in particular, interaction of Hh protein and transmembrane proteins: suppressor Patched (Ptc) and protocancerogenic Smoothened (Smo).

The eight groups of the submitted compounds include the derivatives of 2,6-dihydro-7H-pyrazolo[3,4-d]pyridazin-7-ones and 1,4-dihydropyrazolo[3,4-b][1,4]thiazin-5-one; N-acylated 4-imidazo[1,2-a]pyridin-2-yl- and 4-imidazo[1,2-a]pyrimidin-2-yl-anilines; amides of [(4H-thieno[3,2-b]pyrrol-5-yl)carbonyl]piperidine-4-carboxylic acid; amides of 2-(4-carbamoylpiperidin-1-yl)isonicotinic acid; amides of N-sulfonyl-1,2,3,4-tetrahydroquinoline-6-carboxylic acid; and N-acylated 3-azolyl derivatives of 2-amino-4,5,6,7-tetrahydrothieno[2,3-c]pyridine.

More specifically, the invention relates to inherent physiological activity of the said compounds, consisting in inhibition of Hh signalling cascade, making it possible to use them as active drug substances suppressing so-called Hh signalling pathway and inducing programmed cellular death (apoptosis) and/or inhibiting cellular proliferation; and also to methods for synthesis of the said derivatives, and also to focused libraries, comprising these compounds; and also to pharmaceutical compositions comprising these compounds as active ingredients; and also to a method for treatment of oncological diseases.

BACKGROUND OF THE INVENTION

Family of Hedgehog genes have been studied from the beginning of 1990th years when the first gene of this kind has been found at *drosophila*-fly. *Drosophila*'s maggots exhibiting the mutant version of this gene are covered with sharp excrescences looking like hedgehog needles (from here the gene name hedgehog—a hedgehog). These genes code Hedgehog (Hh) secreted proteins, represented at vertebrated animals by Desert (DHh), Sonic (SHh) and Indian (IHh) Hh proteins. When entering Hh signalling system Hh proteins are subjected to intramolecular splitting and lipidic modification, the latter is catalyzed by C-terminal fragment of protein-precursor acting as cholesterol transferase [Porter J. A., Young K. E., Beachy P. A. Cholesterol modification of hedgehog signalling proteins in animal development. *Science*. 1996; 274: 1597]. As a result of it a peptide with mass about 19 kD esterified at C-termination with cholesterol molecule (HhNp) is formed. This modified peptide is responsible for all known signalling activities of Hh proteins. At mammals SHhNp-protein is subjected to further palmitoylation at N-termination that leads to enhancement of its signalling activity. By means of Hh signalling system Hh proteins regulate the process of various organs and tissues construction in the course of embryonal development [Neumann C. J. Hedgehogs as negative regulators of the cell cycle. *Cell Cycle*. 2005; 4(9):1139-40]. For example, SHh, among other things, is connected with morphogenesis of nervous tissue and intestinal tract, and DHh is involved in differentiation of male genital organs. At healthy adult individuals these proteins are operated by stem cells [Lewis M. T., Visbal A. P. The hedgehog signalling network, mammary stem cells, and breast cancer: connections and controversies. Ernst. Schering Found. *Symp. Proc*. 2006; 5:181-21]. The distortion of Hh signalling system, in particular, its enhanced activity leads to cancerous transformation of tissue [Evangelista M., Tian H., de Sauvage F. J. The hedgehog signalling pathway in cancer. *Clin. Cancer Res*. 2006; 12(20 Pt 1):5924-8]. A simplified model of Hh signalling system including the key components and biotargets in Hh signalling system is described in: [Kiselyov A. S., Tkachenko S. E., Balakin K. V., Ivachtchenko A. V. Small-molecule modulators of Hh and Wnt signalling pathways. *Expert Opin. Ther. Targets*. 2007; 11(8): 1087-1101].

Hh proteins transfer a signal into the cell by means of two transmembrane proteins: suppressor Ptc and protooncogenous Smo. Hh protein is directly linked with 12-tuple membrane penetrating protein Ptc, which is negative Smo protein modulator. Smo protein belonging to serpentine receptor family, penetrates cell membrane seven times and contains N-terminal CRD domain (cysteine-rich domain). There is some similarity of protein Smo to 7-transmembrane receptors connected with G-proteins, however, up to now neither endogenous Smo-modulator, nor corresponding effector G-protein have been found.

In the absence of Hh-peptide Ptc Protein completely inactivates Smo receptor and Hh signalling system does not operate. There are some possible ways of Ptc and Smo proteins interaction [Ogden S. K., Ascano M., Stegman M. A., Robbins D. J. Regulation of Hedgehog signaling: a complex story. *Biochem. Pharmacol*. 2004; 67(5):805-14], in particular, it is supposed the formation of heterodimeric receptor. However, on the basis of experimentally established difference in membrane localizations of these proteins in vivo alternative catalytical models of their interaction were offered.

Not so much is known about the mechanism of action of the molecules participating in the further formation of SHhNp signalling cascade in cytosol. Signalling complex comprising transcriptional factors Gli1, Gli2 or Cli3 (homologues of Cubitus Interruptus (Ci) at flies *Drosophila*), is regulated by physical interaction with microtubules. Serine-threonine kinase Fu (Fused), suppressor Fu (SuFu) and kinesin-alike protein Cos 2 are the components of this complex [Claret S., Sanial M., Plessis A. Evidence for a novel feedback loop in the Hedgehog pathway involving Smoothened and Fused. *Curr Biol*. 2007; 17(15): 1326-33]. In the absence of signal transmission from Hh protein the said components of the complex are associated with microtubules. It is supposed, that the essential role of Fu kinase consists in directing suppressor and Cos 2 protein functions. Kinase Fu mutation leads to the loss of any form of Ci processing, that, eventually, initiates stopping of Hh signalling. It is expected that Fu kinase could be a perspective medicinal biotarget, and its inhibiting will cause blockade of Hh signalling system. At the same time, the mechanism of Fu kinase activation is not entirely clarified, and its analogue at mammals has not been determined yet.

Thus, SHhNp-protein induces phosphorylation and dissociation of signalling complex from the surface of microtubules. This facilitates translocating of transcriptional factors Gli1, Gli2 and/or Cli3 into cell nucleus. There they associate with c-AMP-sensitive binding protein (CBP) and initiate transcription, that leads, among other processes, to enhancement of activity of alkaline phosphatase [Pepinsky R. B., Zeng C. Identification of a palmitic acid-modified form of human Sonic hedgehog. *J. Biol. Chem.* 1998; 273: 14037-45] and cellular proliferation [Chen C. H., Von Kessler D. P., Park W., Wang B., Ma Y., Beachy P. A: Nuclear trafficking of Cubitus interruptus in the transcriptional regulation of Hedgehog target gene expression. *Cell.* 1999; 98(3): 305-16]. It is supposed, that Gli3 carries out regulatory functions at warm-blooded, while Gli1 and Gli2 are activators [Park H. L., Bai C., Platt K. A. Mouse Gli1 mutants are viable but have defects in SHH signaling in combination with a Gli2 mutation. *Development.* 2000 127(8): 1593-605].

It is also supposed that some biological processes and biotargets in Hh-signalling cascade could be sensitive to the action of small molecules and could be controlled by them, the verity of this is supported by the whole series of drug candidates, being at present at various stages of clinical investigation (Table 1, only signalling cascade antagonists are represented) [http://www.integrity.prous.com].

In the context of novel drugs creation protein Smo in this cascade is considered to be one of the most perspective, and that was confirmed by the discovery of various, structurally similar ligands [Frank-Kamenetsky M., Zhang X. M., Bottega S. Small-molecule modulators of Hedgehog signaling: Identification and characterization of smoothened agonists and antagonists. *J. Biol.* 2002; 1(2): 10].

Steroid teratogenic alkaloides cyclopamin and jervine, isolated from poisonous Hellebore (*Veratrum californicum*), are the first discovered small molecule antagonists of Hh-signalling cascade [Williams J. A., Guicherit O. M., Zaharian B. I. Identification of a small molecule inhibitor of the hedgehog signalling pathway: effects on basal cell carcinoma-like lesions. *Proc. Natl. Acad. Sci.* 2003; 100(8): 4616-21]. Cyclopamin inhibits Smo functions, directly binding to heptahelical protein and preserving by that its inactive conformation [Taipale J., Chen J. K., Cooper M. K. Effects of oncogenic mutations in Smoothened and Patched can be reversed by cyclopamine. *Nature.* 2000; 406(6799): 1005-9]. Cyclopamin shows high antitumor activity in vitro and in vivo in models of medulloblastoma [Berman D. M., Karhadkar S. S., Hallahan A. R. Medulloblastoma growth inhibition by hedgehog pathway blockade. *Science.* 2002; 297(5586): 1559-61], basal carcinoma [Williams J. A. Hedgehog signaling pathway as a target for therapeutic intervention in basal cell carcinoma. *Drug News Perspect.* 2003; 16(10): 657-62] and breast cancer, in which Hh-signalling cascade is activated [Kubo M., Nakamura M., Tasaki A. Hedgehog signaling pathway is a new therapeutic target for patients with breast cancer. *Cancer Research.* 2004; 64(17): 6071-6074]. It is also possible, that arrest of Hh-signalling cascade induced by cyclopamin could be used as basically novel approach for treatment of psoriasis

TABLE 1

Hh-signalling cascade modulators at various stages of clinical investigation (data for november 2007)

| Compound | Mechanism | Phase of test | Sponsor | Therapeutic group |
|---|---|---|---|---|
| CUR-61414 (G-024856) | Smo receptor antagonist; Hh-signalling cascade inhibitor | Phase I | Roche, Curis, Genentech | oncology basal carcinoma |
| Cyclopamine | Smo receptor antagonist, Hh signalling inhibitor | Preclinical phase | Johns Hopkins University, Howard Hughes Medical Institute, Curis | oncology |
| HhAntag | Smo receptor antagonist; Hh-signalling cascade inhibitor | Preclinical phase/ Phase I | Curis | oncology |
| SANT-1 | Smo receptor antagonist; Hh-signalling cascade inhibitor | Preclinical phase | Johns Hopkins University | oncology |
| CUR-691 | Smo receptor, antagonist; Hh-signalling cascade inhibitor | Preclinical phase | Curis, Genentech | oncology Brain tumours |
| IPI-609 | Hh-signalling cascade inhibitor | Preclinical phase | Infinity Pharmaceuticals | oncology |
| IPI-926 | Hh-signalling cascade inhibitor | Preclinical phase | Infinity Pharmaceuticals | oncology |
| NSC-75503 | Hh-signalling cascade inhibitor | Preclinical phase | Karolinska Institute | oncology |
| GANT-61 | Hh-signalling cascade inhibitor | Preclinical phase | Karolinska Institute | oncology |
| MEDI-562 | Hh-signalling cascade inhibitor | Preclinical phase | MedImmune | oncology |

[Meth M. J., Weinberg J. M. Cyclopamine: inhibiting hedgehog in the treatment of psoriasis. *Cutis.* 2006; 78(3):185-8].

Abberant activation of Hh-signalling cascade has been found in various tumours of humans [Evangelista M., Hua Tian H., de Sauvage F. J. The Hedgehog Signaling Pathway in *Cancer Clin Cancer Res.* 2006; 12: 5924-5928], in particular, for the most aggressive forms of prostate cancer [Aparicio A. L. M., Campelo G. R., Espinosa C. J., Ayerbes V. M., Lopez R. M., Prado D. S., Gallego A. G. Prostate cancer and Hedgehog signalling pathway. *Clin. Transl. Oncol.* 2007; 9(7): 420-8]. That is the reason for the high interest to antagonists of this cascade as to essentially novel low-toxic oncolytic drug substances.

Thus, searching for effective inhibitors of Hh-signalling cascade is an extremely important, urgent and promising problem.

For the purpose of finding out novel highly effective oncolytic drug substances the authors of the invention carried out a broad screening investigation of compounds with low-molecular weight of different structures among which hit-compounds and leader-compounds belonging to eight families of heterocyclic compounds have been found, directed modifications of many positions of discovered structures were performed, and as a result of all that series of novel derivatives of the said heterocycles have been synthesized which are original and highly effective inhibitors of Hh signalling cascade. The prepared physiologically active heterocyclic compounds include derivatives of 2,6-dihydro-7H-pyrazolo[3,4-d]pyridazin-7-one and 1,4-dihydropyrazolo[3,4-b]thiazin-5(6H)-one; N-acylated 4-imidazo[1,2-a]pyridin-2-yl- and 4-imidazo[1,2-a]pyrimidin-2-yl-anilines; amides of [(4H-thieno[3,2-b]pyrrol-5-yl)carbonyl]piperidine-4-carboxylic acid; amides of 2-(4-carbamoylpiperidin-1-yl)isonicotinic acid; amides of N-sulfonyl-1,2,3,4-tetrahydroquinoline-6-carboxylic acid; and N-acylated 3-azolyl derivatives of 2-amino-4,5,6,7-tetrahydrothieno[2,3-c]pyridine as well. The prepared compounds have not been described before; their ability to inhibit Hh signalling cascade has not been known either.

DISCLOSURE OF THE INVENTION

In the context of the present invention, the terms are generally defined as follows:

"Agonists" means ligandes, being combined with receptors of definite type, actively promote transferring their specific signal and by that cause the biological answer of cell.

"Azaheterocycle" means aromatic or nonaromatic mono- or polycyclic system with, at least, one nitrogen atom, for example, piperidine, morpholine.

"Alkyl" means aliphatic hydrocarbon straight or branched chain with 1-12 carbon atoms. Branched means that the alkyl chain has one or more "lower alkyl" substituents. Alkyl group may have one or more substituents of the same or different structure ("alkyl substituent") including halogen, alkenyloxy, cycloalkyl, aryl, heteroaryl, heterocyclyl, aroyl, cyano, hydroxy, alkoxy, carboxy, alkynyloxy, aralkoxy, aryloxy, aryloxycarbonyl, alkylthio, heteroarylthio, aralkylthio, arylsulfonyl, alkylsulfonyl, heteroaralkyloxy, annelated heteroarylcycloalkenyl, annelated heteroarylcycloalkyl, annelated heteroarylheterocyclenyl, annelated heteroarylheterocyclyl, annelated arylcycloalkenyl, annelated arylcycloalkyl, annelated arylheterocyclenyl, annelated arylheterocyclyl, alkoxycarbonyl, aralkoxycarbonyl, heteroaralkyloxycarbonyl or $R_k{}^a R_{k+1}{}^a N-$, $R_k{}^a R_{k+1}{}^a NC(=O)-$, $R_k{}^a R_{k+1}{}^a NC(=S)-$, $R_k{}^a R_{k+1}{}^a NSO_2-$, where $R_k{}^a$ and $R_{k+1}{}^a$ independently of each other represent "amino group substituents", the meanings of which are defined in this section, for example, hydrogen, alkyl, aryl, aralkyl, heteroaralkyl, heterocyclyl or heteroaryl, or $R_k{}^a$ and $R_{k+1}{}^a$ together with the N-atom, they are attached to, form through $R_k{}^a$ and $R_{k+1}{}^a$ 4-7-membered heterocyclyl or heterocyclenyl. The preferred alkyl group are methyl, trifluoromethyl, cyclopropylmethyl, cyclopentylmethyl, ethyl, n-propyl, iso-propyl, n-butyl, tert-butyl, n-pentyl, 3-pentyl, methoxyethyl, carboxymethyl, methoxycarbonylmethyl, ethoxycarbonylmethyl, benzyloxycarbonylmethyl, methyloxycarbonylmethyl and pyridilmethyloxycarbonylmethyl. The preferred "alkyl substituents" are cycloalkyl, aryl, heteroaryl, heterocyclyl, hydroxy, alkoxy, alkoxycarbonyl, aralkoxy, aryloxy, alkylthio, heteroarylthio, aralkylthio, alkylsulfonyl, arylsulfonyl, alkoxycarbonyl, aralkoxycarbonyl, heteroaralkyloxycarbonyl or $R_k{}^a R_{k+1}{}^a N-$, $R_k{}^a R_{k+1}{}^a NC(=O)-$, annelated arylheterocyclenyl, annelated arylheterocyclyl.

Used in the given above definitions and subsequent description the term "lower alkyl" means straight or branched alkyl group with 1-7 C atoms, examples of which are methyl, ethyl, isopropyl, butyl, sec-butyl, tert-butyl and others. Terms "alkenyl" and "alkynyl" have analogous meanings, but their hydrocarbon chains contain double and triple C—C bonds.

"Alkoxy" means AlkO-group, in which alkyl is defined above. Methoxy, ethoxy, butoxy and analogous groups are examples of alkoxy groups.

"Annelated cyclic structure" (condensed cyclic structure) means bi- or polycyclic system in which the annelated cyclic structure and cyclic structure or polycyclic structure to which it is "annelated" have at least two common atoms.

"Antagonists" mean ligands which are bound with definite receptors and do not cause active cellular response. Antagonists prevent bounding agonists and receptors and by that blocking specific signal transfer.

"Aryl" means aromatic mono- or polycyclic system with 6-14 carbon atoms, preferably from 6 to 10 C-atoms. Aryl may have one or more "cyclic system substituents" of the same or different structure. Phenyl or naphthyl, substituted phenyl or substituted naphthyl are the representatives of aryl groups. Aryl could be annelated with nonaromatic cyclic system or heterocycle.

"Aralkyl" means aryl-alkyl group, in which aryl and alkyl are defined in this section.

"Acyl" means COR'-group (in which R' represents H, alkyl, aryl, heterocyclyl and aralkyl, the meanings of which are defined in this section). Acetyl, benzoyl, phenylacetyl and others are the examples of acyl groups.

"Halogen" means fluorine, chlorine, bromine and iodine.

"Heterocycle" means one or more optionally fully saturated or aromatic cycles with 5, 6 or 7 atoms, at least, one of them is heteroatom. The preferable heteroatoms are S, O and N. "Heterocycle" could be condensed polycycle, as benzimidazole, benzoxazole, benzothiazole, quinoline, or noncondensed, as bipyridile. "Substituted heterocycle" have one or more substituents.

"Heteroannelated cyclic structure" means that the cyclic structure that is attached (annelated or condenced) to another cyclic or polycyclic structure contains at least one heteroatom.

"Heterocyclyl" means an aromatic or nonaromatic saturated monocyclic or polycyclic system containing 3 to 10 carbon atoms, preferably 5 to 6 carbon atoms, in which one or several carbon atoms are replaced with a heteroatom such as nitrogen, oxygen or sulfur. The prefixes "aza", "oxa" or "thia" preceding the word "heterocyclyl" indicate the presence of a nitrogen atom, an oxygen atom, or a sulfur atom, respectively, in the cyclic system. Heterocyclyl may have one or more "cyclic system substituents" that may be identical or different. Nitrogen atom and sulfur atom in heterocyclyl fragment may be oxidized to an N-oxide, an S-oxide and an S-dioxide. Heterocyclyls are represented by piperidinyl, pyrrolidinyl, piperazinyl, morpholinyl, thiomorpholinyl, thiazolidinyl, 1,4-dioxan-2-yl, tetrahydrofuranyl, tetrahydrothiophenyl, and so on.

"Substituent" means a chemical radical which is attached to a template, scaffold or intermediate product during their preparation.

"NH-Protective substituent" means a chemical radical attached to a template, scaffold or synthetic intermediate for temporary protection of amino group in multifunctional compounds, including, but not limited to: amide substituent, such as formyl, optionally substituted acetyl (for example, trichloroacetyl, trifluoroacetyl, 3-phenylpropionyl and others), optionally substituted benzoyl and others; carbamate substituent, such as optionally substituted $C_1$-$C_7$-alkoxycarbonyl, for example, methyloxycarbonyl, ethyloxycarbonyl, tert-butyloxycarbonyl, 9-fluorenylmethyloxycarbonyl (Fmoc) and others; optionally substituted $C_1$-$C_7$-alkyl substituent, for example, tert-butyl, benzyl, 2,4-dimethoxybenzyl, 9-phenylfluorenyl and others; sulfonyl substituent, for example, benzenesulfonyl, p-toluenesulfonyl and others. More specifically "Protective groups" are described in the book: Protective groups in organic synthesis, Third Edition, Green, T. W. and Wuts, P. G. M. 1999, p. 494-653. Jon Wiley & Sons, Inc., New York, Chichester, Weinheim, Brisbane, Toronto, Singapore.

"Inert substituent" ("non-interfering substituent") means a low- or non-reactive radical, including, but not limited to: $C_1$-$C_7$ alkyl, $C_2$-$C_7$ alkenyl, $C_2$-$C_7$ alkynyl, $C_1$-$C_7$ alkoxy, $C_7$-$C_{12}$ aralkyl, substituted by inert substituents aralkyl, $C_7$-$C_{12}$ heterocyclylalkyl, substituted by inert substituents heterocyclylalkyl, $C_7$-$C_{12}$ alkaryl, $C_3$-$C_{10}$ cycloalkyl, $C_3$-$C_{10}$ cycloalkenyl, phenyl, substituted phenyl, toluoyl, xylenyl, biphenyl, $C_2$-$C_{12}$ alkoxyalkyl, $C_2$-$C_{10}$ alkylsulfinyl, $C_2$-$C_{10}$ alkylsulfonyl, $(CH_2)_m$—O—($C_1$-$C_7$ alkyl), —$(CH_2)_m$—N($C_1$-$C_7$ alkyl)$_n$, aryl; aryl substituted by inert substituent; alkoxy group substituted by inert substituent; fluoroalkyl, aryloxyalkyl, heterocyclyl; heterocyclyl substituted by inert substituents and nitroalkyl; where m and n are varied from 1 to 7. $C_1$-$C_7$ Alkyl, $C_2$-$C_7$ alkenyl, $C_2$-$C_7$ alkynyl, $C_1$-$C_7$ alkoxy, $C_7$-$C_{12}$ aralkyl, $C_7$-$C_{12}$ alkaryl, $C_3$-$C_{10}$ cycloalkyl, $C_3$-$C_{10}$ cycloalkenyl, phenyl; phenyl substituted by inert substituents; $(CH_2)_m$—O—($C_1$-$C_7$ alkyl), —$(CH_2)_m$—N($C_1$-$C_7$ alkyl)$_n$, aryl; aryl substituted by inert substituents, heterocyclyl and heterocyclyl substituted by inert substituents are the preferred inert substituents.

"Combinatorial library" means a collection of compounds produced by parallel synthesis and intended for searching a hit or leader compounds, and for optimization of physiological activity of the hit or leader (for example, physiological activity, selectiveness, bioavailability and so on) as well, moreover each compound of the library corresponds to the common template.

"Drug substance" means physiologically active compound of synthetic or others (biotechnological, vegetable, animal, microbal and others) origin with pharmacological activity which is an active ingredient of pharmaceutical composition employed in production and preparation of medicine (drug).

"Medicine" (drug)—is a compound (or a mixture of compounds in the form of pharmaceutical composition), intended for restoration, improvement or modification of physiological functions at humans and animals, and for treatment and prophylaxis of diseases, diagnostics, anesthesia, contraception, cosmetology and others.

"Ligandes" (from latin ligo) represent chemical compounds (small molecule, peptide, protein and others) or inorganic ion, capable to interact with receptors which convert this interaction into specific signal.

"Nucleophylic" means electron-excessive reagent.

"Nucleophylic substituent" means a chemical radical attached to the template or scaffold as a result of a reaction with a nucleophylic reagent, for example, one selected from a group of primary or secondary amines, alcohols, phenols, mercaptans and thiophenols.

"Parallel synthesis" means a method for carrying out a chemical synthesis of combinatorial library of individual compounds.

"Receptors" (from latin recipere) represent biological macromolecules located either on cytoplasmic cell membrane or intracellular, capable specifically interact with restricted number of physiologically active substances (ligandes) and transform the signal about this interaction to definite cellular response.

"Signalling cascade" (signalling system, cascade of signal transferring) means a plurality of related consecutive and parallel molecular processes of cellular metabolism regulation by external (primary) signals, transporting information to the cell, and this property in principle distinguishes them from other chemical compounds penetrating into the cell which are the source of energy and matter for it. Molecular mechanisms of external signal transduction into the cell means not only transport of signals as themselves, but the whole complex of events connected with it, including enhancement, attenuation and suppression (or stopping) of signals.

"Scaffold" means common or similar molecular frame of compounds typical for all compounds composing combinatorial and/or focused library.

"Leader compound" (leader) means a compound with confirmed outstanding (maximum) physiological activity found in the series of similar physiologically active compounds. Leader compound should possess a number of certain properties making it possible to create a potential drug candidate. These properties are: selectivity of action, absence of toxicofors in its structure, and a number of physico-chemical characteristics providing its high bioavailability (for example, validity to Lipinski rule) [Lipinski C. A., Lombardo F., Dominy B. W., Feeney P. J. Experimental and computational approaches to estimate solubility and permeability in drug discovery and development settings. *Adv. Drug Deliv. Rev.* 2001; 46(1-3):3-26]).

"Hit compound" (hit) means a compound demonstrated the desired physiological activity during the primary screening process.

"Template" means common structural fragment or invariable part of compounds, typical for all comprising combinatorial library compounds.

"Therapeutic cocktail" is a simultaneously administered combination of two or more drug substances with different mechanism of pharmacological action and aimed at different biotargets taking part in pathogenesis of the disease.

"Leaving group" means a group, which are substituted by another atom or group.

"Pharmaceutical composition" means a composition comprising a drug substance (or a number of them) and, at least, one of the components selected from the group, consisted of pharmaceutically acceptable and pharmacologically compatible excipients, solvents, diluents, carriers, auxiliary, distributing and perceiving means, means acting as a vehicle, such as preserving agents, stabilizers, excipients, grinders, wetting agents, emulsifying and suspending agents, thickeners, sweeteners, flavouring agents, antibacterial agents, fungicides, lubricants, regulators of the prolonged delivery, the choice and suitable proportions of which depends on the nature and the way of administration and dosage.

"Pharmacologically acceptable salts" incorporate all the salts yielded by compounds (bases) and pharmacologically acceptable acids, such as inorganic (for example, hydrochloric acid, sulfuric acid, phosphoric acid and others) and organic acids (for example, succinic acid, citric acid, tartaric acid, maleic acid, methanesulphonic acid, p-toluenesulfonic acid and others). Besides, "pharmacologically acceptable salts" could be synthesized as metal salts (sodium, potassium, lithium, calcium, magnesium) and salts of organic bases (for example, various amines, hydroxyalkylamines, aminoacids with high basicity and so on).

"Focused library" is a combinatorial library or a combination of several combinatorial libraries, or a combination of libraries and compounds arranged in a special way to enhance the probability of finding hits and leaders or to improve the efficiency of their optimization. The design of focused libraries is, as a rule, associated with the directed search for effectors (inhibitors, activators, agonists, antagonists and so on) of definite biotargets (enzymes, receptors, ion channels and so on) and based upon the information (or hypothesis) about the properties of biotarget (target-oriented design) or peculiarities of known effectors of this (or related) biotarget (ligand-oriented design).

"Cycloalkenyl" means cyclic unsaturated hydrocarbon group with 5-7 C atoms, for example cyclopentenyl, cyclohexenyl and others.

"Cycloalkyl" means non-aromatic monocyclic or polycyclic system containing from 3 to 10 carbon atoms. Cycloalkyl may have one or more "cyclic system substituents" that may be identical or different. The cyclic system groups are represented by cyclopropyl, cyclobutyl, cyclopentyl, cyclohexyl, decalinyl, norbornyl, adamant-1-yl, and so on. Cycloalkyl may be annelated to aromatic cycle or heterocycle. The preferred "cyclic system substituents" are represented by alkyl, aralkoxy, hydroxy or $R_k{}^a R_{k+1}{}^a N—$, the values of which are defined in this section.

"Electrophilic" means electrono-deficient reagent.

"Electrophilic substituent" means a chemical radical attached to the template or scaffold as a result of a reaction with an electrophilic reagent, for example, one selected from a group of organic halides, organic acids or their derivatives (anhydrides, imidazolides, acid halides), organic sulfonic acid esters or chlorides, organic haloformates, organic isocyanates and organic isothiocyanates.

The purpose of the present invention—is synthesis of eight groups of novel heterocyclic compounds, which are derivatives of 2,6-dihydro-7H-pyrazolo[3,4-d]pyridazin-7-one of the general formula I and 1,4-dihydropyrazolo[3,4-b][1,4]thiazin-5-one of the general formula II; N-acylated 4-imidazo[1,2-a]pyridin-2-yl- and 4-imidazo[1,2-a]pyrimidin-2-yl-anilines of the general formulas III and IV respectively; amides of [(4H-thieno[3,2-b]pyrrol-5-yl)carbonyl]piperine-4-carboxylic acid of the general formula V; amides of 2-(4-carbamoylpiperidin-1-yl)isonicotinic acid of the general formula VI; amides of N-sulfonyl-1,2,3,4-tetrahydroquinoline-6-carboxylic acid of the general formula VII; and N-acylated 3-benzazolyl derivatives of 2-amino-4,5,6,7-tetrahydrothieno[2,3-c]pyridine of the general formula VIII as well (some of these compounds having substituents with acid or base functions could be presented either as acids or bases or their pharmacologically acceptable salts),

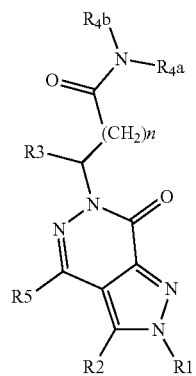

I

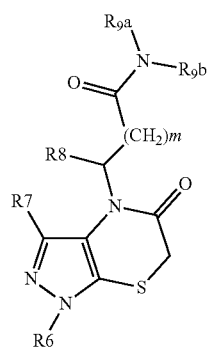

II

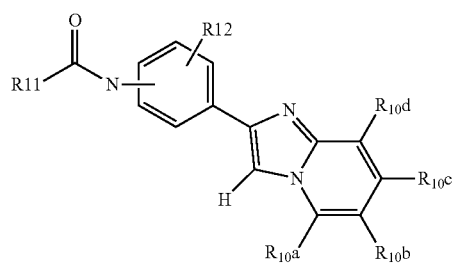

III

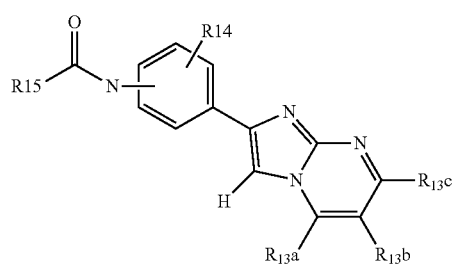

IV

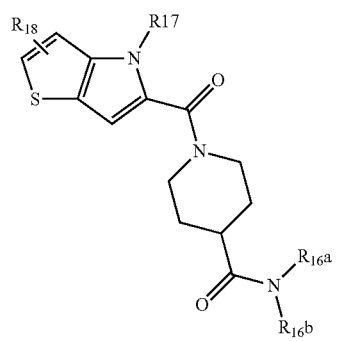

V

-continued

VI

VII

VIII

X = O, S wherein:
X represents oxygen atom or sulfur atom;
n and m are integer number 0, 1, 2 or 3;
R1 represents H, inert, NH-protected or erectrophylic substituent;
R2, R5 represent H or lower alkyl;
R3 represents H or inert substituent;
R4 represents H or inert substituent, or R4a and R4b together with the N atom they are attached to via R4a and R4b could form optionally substituted azaheterocycle (for example, pyrrolidine, piperidine, piperazine, homopiperidine, homopiperazine, mopholine, thiomorpholine and others);
R6 represents H, inert, NH-protected or erectrophylic substituent;
R7 represents H or inert substituent;
R8 represents H or inert substituent;
R9 represents H or inert substituent, or R9a and R9b together with the N atom they are attached to via R9a and R9b could form optionally substituted azaheterocycle (for example, pyrrolidine, piperidine, piperazine, homopiperazine, mopholine, thiomorpholine and others);
R10 represents H or inert substituent;
R11 represents H or inert substituent;

R12 represents H, halogen, $CF_3$, $CF_3O$, CN, $NO_2$ group or inert substituent;
R13 represents H or inert substituent;
R14 represents H, halogen, $CF_3$, $CF_3O$, CN, $NO_2$ group or inert substituent;
R15 represents H or inert substituent;
R16 represents H or inert substituent, or R16a and R16b together with the N atom they are attached to via R16a and R16b could form optionally substituted azaheterocycle (for example, pyrrolidine, piperidine, piperazine, homopiperazine, mopholine, thiomorpholine and others);
R17 represents H, inert, NH-protected or erectrophylic substituent;
R18 represents H or inert substituent;
R19 represents H or inert substituent, or R19a and R19b together with the N atom they are attached to via R19a and R19b could form optionally substituted azaheterocycle (for example, pyrrolidine, piperidine, piperazine, homopiperazine, mopholine, thiomorpholine and others);
R20 represents H or inert substituent, or R20a and R20b together with the N atom they are attached to via R20a and R20b could form optionally substituted azaheterocycle (for example, pyrrolidine, piperidine, piperazine, homopiperazine, mopholine, thiomorpholine and others);
R21 represents H or inert substituent;
R22 represents H or inert substituent, or R22a and R22b together with the N atom they are attached to via R22a and R22b could form optionally substituted azaheterocycle (for example, pyrrolidine, piperidine, piperazine, homopiperazine, mopholine, thiomorpholine and others);
R23 represents H or inert substituent;
R24 represents H, inert, NH-protected or erectrophylic substituent;
R25 represents H, halogen, $CF_3$, $CF_3O$, CN, $NO_2$ group or inert substituent.

According to the invention among the eight groups of compounds of the general formulas I-VIII, the preferable compounds are the following eight subgroups of compounds of the general formulas (I-1), (II-1), (III-1a and III-1b), (IV-1a and IV-1b), (V-1), (VI-1), (VII-1) and (VIII-1), shown below:

I-1

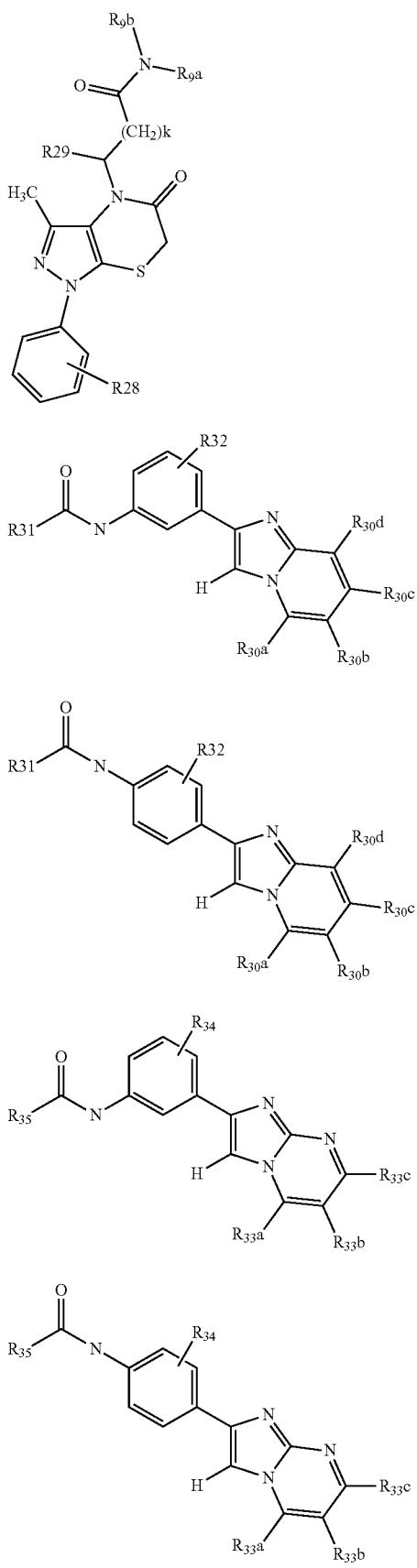
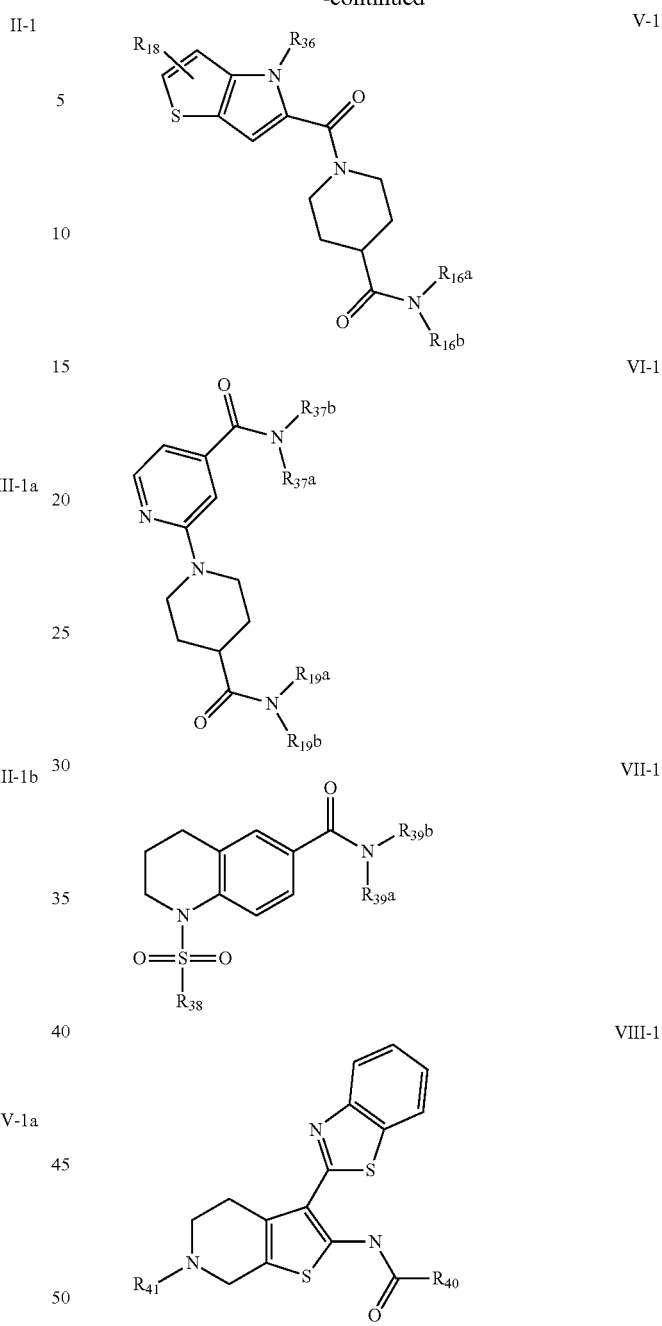

wherein:
 i and k are integer number 0, 1, or 2;
 R4, R9, R16 and R19 are all as defined above;
 R26 represents H, halogen, CF3, CF3O, CN, NO2 group or inert substituent;
 R27 represents H, optionally substituted benzyl, optionally substituted aryl or optionally substituted lower alkyl;
 R28 represents H, halogen, CF3, CF3O, CN, NO2 or inert substituent;
 R29 represents H, optionally substituted benzyl, optionally substituted aryl or optionally substituted lower alkyl;
 R30 represents H, halogen, methoxy group or lower alkyl;
 R31 represents inert substituent;
 R32, R33, R34 represent H, halogen, methoxy group or lower alkyl;

R35 represents inert substituent;

R36 represents H, optionally substituted benzyl, optionally substituted aryl, optionally substituted hetaryl or optionally substituted lower alkyl;

R37 represents H, optionally substituted benzyl, optionally substituted aryl, optionally substituted hetaryl or optionally substituted lower alkyl, or R37a и R37b, together with the N atom they are attached to via R37a and R37b could form optionally substituted azaheterocycle (for example, pyrrolidine, piperidine, piperazine, homopiperazine, morpholine, thiomorpholine and others);

R38 represents optionally substituted benzyl, optionally substituted aryl, optionally substituted hetaryl or optionally substituted lower alkyl;

R39 represents H, optionally substituted benzyl, optionally substituted aryl, optionally substituted hetaryl or optionally substituted lower alkyl, or R39a and R39b, together with the N atom they are attached to via R39a and R39b could form optionally substituted azaheterocycle (for example, pyrrolidine, piperidine, piperazine, homopiperazine, morpholine, thiomorpholine and others);

R40 represents inert substituent;

R41 represents inert substituent.

The most preferable compounds are the following individual compounds of the general formulas I-VIII and their pharmaceutically acceptable salts:

I-1001. 2-Phenyl-3,4-dimethyl-6-{2-[4-(3-methoxyphenyl)piperazin-1-yl]-2-oxoethyl}-2,6-dihydro-7H-pyrazolo[3,4-d]pyridazin-7-one;

I-1002. 2-Phenyl-3,4-dimethyl-6-{2-[4-(3-chlorophenyl)piperazin-1-yl]-2-oxoethyl}-2,6-dihydro-7H-pyrazolo[3,4-c]pyridazin-7-one;

I-1003. 2-Phenyl-3,4-dimethyl-6-{2-[4-phenylpiperazin-1-yl]-2-oxoethyl}-2,6-dihydro-7H-pyrazolo[3,4-c]pyridazin-7-one;

I-1004. 2-Phenyl-3,4-dimethyl-6-{2-[4-(2,3-dimethylphenyl)piperazin-1-yl]-2-oxoethyl}-2,6-dihydro-7H-pyrazolo[3,4-d]pyridazin-7-one;

I-1005. 2-Phenyl-3,4-dimethyl-6-{2-[4-(2,5-dimethylphenyl)piperazin-1-yl]-2-oxoethyl}-2,6-dihydro-7H-pyrazolo[3,4-d]pyridazin-7-one;

I-1006. 2-Phenyl-3,4-dimethyl-6-{2-[4-(4-fluorophenyl)piperazin-1-yl]-2-oxoethyl}-2,6-dihydro-7H-pyrazolo[3,4-d]pyridazin-7-one;

I-1007. 2-Phenyl-3,4-dimethyl-6-{2-[4-(2-fluorophenyl)piperazin-1-yl]-2-oxoethyl}-2,6-dihydro-7H-pyrazolo[3,4-d]pyridazin-7-one;

I-1008. 2 Phenyl-3,4-dimethyl-6-[1-methyl-2-(4-phenylpiperazin-1-yl)-2-oxoethyl]-2,6-dihydro-7H-pyrazolo[3,4-d]pyridazin-7-one;

I-1009. 2-Phenyl-3,4-dimethyl-6-{1-methyl-2-[4-(3-chlorophenyl)piperazin-1-yl]-2-oxoethyl}-2,6-dihydro-7H-pyrazolo[3,4-d]pyridazin-7-one;

I-1010. 2-Phenyl-3,4-dimethyl-6-{1-methyl-2-[4-cyclohexylpiperazin-1-yl]-2-oxoethyl}-2,6-dihydro-7H-pyrazolo[3,4-d]pyridazin-7-one;

I-1011. 2-Phenyl-3,4-dimethyl-6-{1-methyl-2-[4-(2,3-dimethylphenyl)piperazin-1-yl]-2-oxoethyl}-2,6-dihydro-7H-pyrazolo[3,4-d]pyridazin-7-one;

I-1012. 2-Phenyl-3,4-dimethyl-6-{1-methyl-2-[4-benzylpiperazin-1-yl]-2-oxoethyl}-2,6-dihydro-7H-pyrazolo[3,4-d]pyridazin-7-one;

I-1013. 2-Phenyl-3,4-dimethyl-6-{1-methyl-2-[4-(2-fluorophenyl)piperazin-1-yl]-2-oxoethyl}-2,6-dihydro-7H-pyrazolo[3,4-d]pyridazin-7-one;

I-1014. 2-[2-(2,4-dimethylphenyl)-3,4-dimethyl-7-oxo-2,7-dihydro-6H-pyrazolo[3,4-c]pyridazin-6-yl]-N-(2-fluorophenyl)acetamide;

I-1015. 2-Phenyl-3,4-dimethyl-6-[1-(morpholin-4-ylcarbonyl)propyl]-2,6-dihydro-7H-pyrazolo[3,4-c]pyridazin-7-one;

I-1016. 2-[2-(4-Methylphenyl)-3,4-dimethyl-7-oxo-2,7-dihydro-6H-pyrazolo[3,4-d]pyridazin-6-yl]-N-[(5-methylfuran-2-yl)methyl]acetamide;

I-1017. 2-[2-(4-Methylphenyl)-3,4-dimethyl-7-oxo-2,7-dihydro-6H-pyrazolo[3,4-d]pyridazin-6-yl]-N-[2-(thien-2-yl)ethyl]propanamide;

I-1018. 2-[2-(4-Methylphenyl)-3,4-dimethyl-7-oxo-2,7-dihydro-6H-pyrazolo[3,4-c]pyridazin-6-yl]-N-(cyclopropyl)butanamide;

I-1019. 3-(2-Phenyl-3,4-dimethyl-7-oxo-2,7-dihydro-6H-pyrazolo[3,4-c]pyridazin-6-yl)-N-(pyridin-3-ylmethyl)propanamide;

I-1020. 3-(2-Phenyl-3,4-dimethyl-7-oxo-2,7-dihydro-6H-pyrazolo[3,4-c]pyridazin-6-yl)-N-(furan-2-ylmethyl)propanamide;

I-1021. 2-Phenyl-3,4-dimethyl-6-(3-(morpholin-4-yl)-3-oxopropyl)-2,6-dihydro-7H-pyrazolo[3,4-c]pyridazin-7-one;

I-1022. 3-(2-Phenyl-3,4-dimethyl-7-oxo-2,7-dihydro-6H-pyrazolo[3,4-c]pyridazin-6-yl)-N-(thien-2-ylmethyl)propanamide;

I-1023. 4-[2-(4-Methylphenyl)-3,4-dimethyl-oxo-2,7-dihydro-6H-pyrazolo[3,4-d]pyridazin-6-yl]-N-[2-(furan-2-yl)ethyl]butanamide;

I-1024. 2-(4-Methylphenyl)-3,4-dimethyl-6-[4-(4-ethylpiperazin-1-yl)-4-oxobutyl]-2,6-dihydro-7H-pyrazolo[3,4-c]pyridazin-7-one;

I-1025. 2-Phenyl-3,4-dimethyl-6-[4-(morpholin-4-yl)-4-oxobutyl]-2,6-dihydro-2H-pyrazolo[3,4-c]pyridazin-7-one;

I-1026. 4-(2-Phenyl-3,4-dimethyl-7-oxo-2,7-dihydro-6H-pyrazolo[3,4-d]pyridazin-6-yl)-N-[(1-methylethyl)phenyl]butanamide;

I-1027. 2-(2-Phenyl-3,4-dimethyl-7-oxo-2H-pyrazolo[4,3-d]pyridazin-6-yl)-N-[2-(4-benzylpiperidin-1-yl)ethyl]acetamide;

I-1028. 2-Phenyl-3,4-dimethyl-2H-pyrazolo[4,3-d]pyridazin-6-[2-(4-benzylpiperazin-1-yl)-4-oxoethyl]-7-one;

I-1029. 4-(2-p-Tolyl-3,4-dimethyl-7-oxo-2H-pyrazolo[3,4-c]pyridazin-6-yl)-N-(benzo[d][1,3]-dioxol-5-ylmethyl)butylamide;

I-1030. 2-p-Tolyl-3,4-dimethyl-6-[4-oxo-4-(4-(pyridin-2-yl)piperazin-1-yl)butyl]-2H-pyrazolo[3,4-c]pyridazin-7-one;

II-1001. 3-Methyl-4-[2-(3-methyl-4-m-tolylpiperazin-1-yl)-2-oxoethyl]-1-phenyl-1,4-dihydro-pyrazolo[3,4-b][1,4]thiazin-5-one;

II-1002. 2-(3-Methyl-5-oxo-1-phenyl-5,6-dihydro-1H-pyrazolo[3,4-b][1,4]thiazin-4-yl)-N-(3-trifluoromethylphenyl)acetamide;

II-1003. 2-(3-Methyl-5-oxo-1-phenyl-5,6-dihydro-1H-pyrazolo[3,4-b][1,4]thiazin-4-yl)-N-(pyridin-2-ylmethyl)acetamide;

II-1004. N-Cyclopentyl-2-(3-methyl-5-oxo-1-phenyl-5,6-dihydro-1H-pyrazolo[3,4-b][1,4]thiazin-4-yl)acetamide;

II-1005. N-[2-(3,4-Dimethoxyphenyl)ethyl]-2-(3-methyl-5-oxo-1-phenyl-5,6-dihydro-1H-pyrazolo[3,4-b][1,4]thiazin-4-yl)acetamide;

II-1006. N-(Furan-2-ylmethyl)-2-(3-methyl-5-oxo-1-phenyl-5,6-dihydro-1H-pyrazolo[3,4-b][1,4]thiazin-4-yl)acetamide;

II-1007. N-(4-Methoxybenzyl)-2-(3-methyl-5-oxo-1-phenyl-5,6-dihydro-1H-pyrazolo[3,4-b][1,4]thiazin-4-yl)acetamide;

II-1008. N-Isopropyl-2-(3-methyl-5-oxo-1-phenyl-5,6-dihydro-1H-pyrazolo[3,4-b][1,4]thiazin-4-yl)acetamide;

II-1009. 2-(3-Methyl-5-oxo-1-phenyl-5,6-dihydro-1H-pyrazolo[3,4-b][1,4]thiazin-4-yl)-N-(thiophen-2-ylmethyl)acetamide;

II-1010. 2-(3-Methyl-5-oxo-1-phenyl-5,6-dihydro-1H-pyrazolo[3,4-b][1,4]thiazin-4-yl)-N-(2-morpholin-4-yl)ethylacetamide;

II-1011. N-Methyl-2-(3-methyl-5-oxo-1-phenyl-5,6-dihydro-1H-pyrazolo[3,4-b][1,4]thiazin-4-yl)acetamide;

II-1012. 4-{2-[4-(4-Chlorophenyl)piperazin-1-yl]-2-oxoethyl}-3-methyl-1-phenyl-1,4-dihydropyrazolo[3,4-b][1,4]thiazin-5-one;

II-1013. 3-Methyl-4-[2-oxo-2-(pyrrolidin-1-yl)ethyl]-1-phenyl-1,4-dihydropyrazolo[3,4-b][1,4]thiazin-5-one;

II-1014. 3-Methyl-4-[2-(morpholin-4-yl)-2-oxoethyl]-1-phenyl-1,4-dihydropyrazolo[3,4-b][1,4]thiazin-5-one;

II-1015. N-(5-Methylfuran-2-ylmethyl)-2-(3-methyl-5-oxo-1-phenyl-5,6-dihydro-1H-pyrazolo[3,4-b][1,4]thiazin-4-yl)acetamide;

II-1016. N-(3-Chlorobenzyl)-4-(3-methyl-5-oxo-1-phenyl-5,6-dihydro-1H-pyrazolo[3,4-b][1,4]thiazin-4-yl)butyramide;

II-1017. 4-(3-Methyl-5-oxo-1-phenyl-5,6-dihydro-1H-pyrazolo[3,4-b][1,4]thiazin-4-yl)-N-(pyridin-2-ylmethyl)butyramide;

II-1018. N-(3-Methoxyphenyl)-4-(3-methyl-5-oxo-1-phenyl-5,6-dihydro-1H-pyrazolo[3,4-b][1,4]thiazin-4-yl)butyramide;

II-1019. N-(Furan-2-yl)methyl-4-(3-methyl-5-oxo-1-phenyl-5,6-dihydro-1H-pyrazolo[3,4-b][1,4]thiazin-4-yl)butyramide;

II-1020. N-(2-Methoxyethyl)-4-(3-methyl-5-oxo-1-phenyl-5,6-dihydro-1H-pyrazolo[3,4-b][1,4]thiazin-4-yl)butyramide;

II-1021. N-Methyl-4-(3-methyl-5-oxo-1-phenyl-5,6-dihydro-1H-pyrazolo[3,4-b][1,4]thiazin-4-yl)butyramide;

II-1022. 4-[(4-Azepan-1-yl)-4-oxobutyl]-3-methyl-1-phenyl-1,4-dihydropyrazolo[3,4-b][1,4]thiazin-5-one;

II-1023. 3-Methyl-4-[4-oxo-4-(4-phenylpiperazin-1-yl)butyl]-1-phenyl-1,4-dihydropyrazolo[3,4-b][1,4]thiazin-5-one;

II-1024. 3-Methyl-4-[4-(morpholin-4-yl)-4-oxobutyl]-1-phenyl-1,4-dihydropyrazolo[3,4-b][1,4]thiazin-5-one;

II-1025. 3-Methyl-4-[4-oxo-4-((4-pyridin-2-yl)piperazin-1-yl)butyl]-1-phenyl-1,4-dihydropyrazolo[3,4-b][1,4]thiazin-5-one;

II-1026. N-(4-Methoxyphenyl)-4-(3-methyl-5-oxo-1-phenyl-5,6-dihydro-1H-pyrazolo[3,4-b][1,4]thiazin-4-yl)butyramide;

III-1001. N-(4-(Imidazo[1,2-a]pyridin-2-yl)phenyl)-3-methoxybenzamide;

III-1002. N-(4-(Imidazo[1,2-a]pyridin-2-yl)phenyl)propionamide;

III-1003. N-(4-(Imidazo[1,2-a]pyridin-2-yl)phenyl)isonicotinamide;

III-1004. N-(4-(Imidazo[1,2-a]pyridin-2-yl)phenyl)thiophen-2-carboxamide;

III-1005. 4-Chloro-N-(4-(imidazo[1,2-a]pyridin-2-yl)phenyl)benzamide;

III-1006. N-(4-(Imidazo[1,2-a]pyridin-2-yl)phenyl)-4-methoxybenzamide;

III-1007. N-(4-(Imidazo[1,2-a]pyridin-2-yl)phenyl)acetamide;

III-1008. N-[4-(8-Methylimidazo[1,2-a]pyridin-2-yl)phenyl]acetamide;

III-1009. N-[4-(8-Methylimidazo[1,2-a]pyridin-2-yl)phenyl]propionamide;

III-1010. 2-Methyl-N-[4-(8-methylimidazo[1,2-a]pyridin-2-yl)phenyl]propionamide;

III-1011. 2-Fluoro-N-[4-(8-methylimidazo[1,2-a]pyridin-2-yl)phenyl]benzamide;

III-1012. 2-Methoxy-N-[4-(8-Methylimidazo[1,2-a]pyridin-2-yl)phenyl]benzamide;

III-1013. N-[4-(8-Methylimidazo[1,2-a]pyridin-2-yl)phenyl]-2-phenylacetamide;

III-1014. N-(3-(Imidazo[1,2-a]pyridin-2-yl)phenyl)propionamide;

III-1015. 4-Fluoro-N-(3-(imidazo[1,2-a]pyridin-2-yl)phenyl)benzamide;

III-1016. Thiophene-2-carboxylic acid N-(3-(imidazo[1,2-a]pyridin-2-yl)phenyl)amide;

III-1017. 4-Methyl-2-phenylthiazol-5-carboxylic acid [3-(7-methylimidazo[1,2-a]pyridin-2-yl)phenyl]amide;

III-1018. N-(3-(Imidazo[1,2-a]pyridin-2-yl)phenyl)-4-methoxybenzamide;

III-1019. 4-Methoxy-N-[3-(5-methylimidazo[1,2-a]pyridin-2-yl)phenyl]benzamide;

III-1020. N-[3-(8-Methylimidazo[1,2-a]pyridin-2-yl)phenyl]nicotinamide;

III-1021. N-[3-(5-Methylimidazo[1,2-a]pyridin-2-yl)phenyl]acetamide;

III-1022. Thiophene-2-carboxylic acid [3-(5-methylimidazo[1,2-a]pyridin-2-yl)phenyl]amide;

III-1023. N-[3-(5-Methylimidazo[1,2-a]pyridin-2-yl)phenyl]isobutyramide;

III-1024. N-[3-(8-Methylimidazo[1,2-a]pyridin-2-yl)phenyl]acetamide;

III-1025. N-[3-(8-Methylimidazo[1,2-a]pyridin-2-yl)phenyl]propionamide;

III-1026. Thiophene-2-carboxylic acid [3-(8-methylimidazo[1,2-a]pyridin-2-yl)phenyl]amide;

III-1027. N-[3-(8-Methylimidazo[1,2-a]pyridin-2-yl)phenyl]-2-phenylacetamide;

III-1028. N-[3-(7-Methylimidazo[1,2-a]pyridin-2-yl)phenyl]propionamide;

III-1029. N-[4-(8-Methylimidazo[1,2-a]pyridin-2-yl)phenyl]-2-bromobenzamide;

III-1030. 4-Methyl-2-phenylthiazol-5-carboxylic acid [3-(imidazo[1,2-a]pyridin-2-yl)phenyl]amide;

III-1031. N-[4-(8-Methylimidazo[1,2-a]pyridin-2-yl)phenyl]-2-methylbenzamide;

III-1032. N-[4-(8-Methylimidazo[1,2-a]pyridin-2-yl)phenyl]-2-chlorobenzamide;

III-1033. N-[4-(8-Methylimidazo[1,2-a]pyridin-2-yl)phenyl]-2,6-dimethylbenzamide;

III-1034. N-[4-(8-Methylimidazo[1,2-a]pyridin-2-yl)phenyl]-2,6-dichlorobenzamide;

III-1035. N-[4-(8-Methylimidazo[1,2-a]pyridin-2-yl)phenyl]-2,6-difluorobenzamide;

III-1036. N-[4-(Imidazo[1,2-a]pyridin-2-yl)phenyl]-2-bromobenzamide;

III-1037. N-[4-(Imidazo[1,2-a]pyridin-2-yl)phenyl]-2-chlorobenzamide;

III-1038. N-[4-(Imidazo[1,2-a]pyridin-2-yl)phenyl]-2-fluorobenzamide;

III-1039. N-[4-(5-Methylimidazo[1,2-a]pyridin-2-yl)phenyl]-2-fluorobenzamide;

III-1040. N-[4-(5-Methylimidazo[1,2-a]pyridin-2-yl)phenyl]-2-chlorobenzamide;

III-1041. N-[4-(5-Methylimidazo[1,2-a]pyridin-2-yl)phenyl]-2-bromobenzamide;
III-1042. N-[4-(8-Methylimidazo[1,2-a]pyridin-2-yl)phenyl]-2-bromobenzamide;
III-1043. N-[4-(3,8-Dimethylimidazo[1,2-a]pyridin-2-yl)phenyl]-2-bromobenzamide;
IV-1001. N-(4-(Imidazo[1,2-a]pyrimidin-2-yl)phenyl)acetamide;
IV-1002. Cyclopentanecarboxylic acid (4-imidazo[1,2-a]pyrimidin-2-ylphenyl)amide;
IV-1003. N-(4-(Imidazo[1,2-a]pyrimidin-2-yl)phenyl)-2-methoxyacetamide;
IV-1004. N-(4-(Imidazo[1,2-a]pyrimidin-2-yl)phenyl)-2-methoxybenzamide;
IV-1005. N-(4-(Imidazo[1,2-a]pyrimidin-2-yl)phenyl)-2-(thiophen-2-yl)acetamide;
IV-1006. N-[4-(7-Methylimidazo[1,2-a]pyrimidin-2-yl)phenyl]acetamide;
IV-1007. 4-Methyl-N-[4-(7-methylimidazo[1,2-a]pyrimidin-2-yl)phenyl]benzamide;
IV-1008. 2-(4-Methoxyphenyl)-N-[4-(7-methylimidazo[1,2-a]pyrimidin-2-yl)phenyl]acetamide;
IV-1009. Thiophene-2-carboxylic acid [4-(7-methylimidazo[1,2-a]pyrimidin-2-yl)phenyl]amide;
IV-1010. Tetrahydrofuran-2-carboxylic acid [4-(7-methylimidazo[1,2-a]pyrimidin-2-yl)phenyl]amide;
IV-1011. N-(4-(Imidazo[1,2-a]pyrimidin-2-yl)phenyl)-3,5-dimethoxybenzamide;
IV-1012. Benzo[1,3]dioxol-5-carboxylic acid (4-imidazo[1,2-a]pyrimidin-2-yl)phenyl amide;
IV-1013. Thiophene-2-carboxylic acid (4-imidazo[1,2-a]pyrimidin-2-yl)phenyl amide;
IV-1014. N-(3-Imidazo[1,2-a]pyrimidin-2-yl)phenyl-3-methylbenzamide;
IV-1015. N-(3-Imidazo[1,2-a]pyrimidin-2-yl)phenyl-2-(thiophen-2-yl)acetamide;
IV-1016. Cyclopentancarboxylic acid (3-imidazo[1,2-a]pyrimidin-2-ylphenyl)amide;
IV-1017. Furan-2-carboxylic acid (3-imidazo[1,2-a]pyrimidin-2-yl)phenyl amide;
IV-1018. N-(5-Imidazo[1,2-a]pyrimidin-2-yl)-2-methylphenyl isobutyramide;
IV-1019. N-(5-Imidazo[1,2-a]pyrimidin-2-yl)-2-methylphenyl-4-methoxybenzamide;
IV-1020. N-(5-Imidazo[1,2-a]pyrimidin-2-yl)-2-methylphenyl-2-m-tolylacetamide;
IV-1021. Thiophene-2-carboxylic acid (5-imidazo[1,2-a]pyrimidin-2-yl)-2-methylphenyl amide;
IV-1022. N-(5-Imidazo[1,2-a]pyrimidin-2-yl)-2-methoxyphenyl acetamide;
IV-1023. Cyclopropanecarboxylic acid (5-imidazo[1,2-a]pyrimidin-2-yl-2-methoxyphenyl)amide;
IV-1024. N-(5-Imidazo[1,2-a]pyrimidin-2-yl)-2-methoxyphenyl-3-methoxybenzamide;
IV-1025. N-(5-Imidazo[1,2-a]pyrimidin-2-yl)-2-methoxyphenyl-2-phenylacetamide;
IV-1026. Furan-2-carboxylic acid (5-imidazo[1,2-a]pyrimidin-2-yl)-2-methoxyphenyl amide;
V-1001. [4-(4-Fluorobenzyl)-4H-thieno[3,2-b]pyrrol-5-yl][4-(morpholine-4-carbonyl)piperidin-1-yl]methanone;
V-1002. 1-[4-(4-Fluorobenzyl)-4H-thieno[3,2-b]pyrrole-5-carbonyl]piperidine-4-carboxylic acid (3,5-dimethylphenyl)amide;
V-1003. 1-(4-Methyl-4H-thieno[3,2-b]pyrrole-5-carbonyl)piperidine-4-carboxylic acid amide;
V-1004. 1-(4-Ethyl-4H-thieno[3,2-b]pyrrole-5-carbonyl)piperidine-4-carboxylic acid cyclopentylamide;
V-1005. 1-(4-Ethyl-4H-thieno[3,2-b]pyrrole-5-carbonyl)piperidine-4-carboxylic acid (furan-2-ylmethyl)amide;
V-1006. 1-(4-Ethyl-4H-thieno[3,2-b]pyrrole-5-carbonyl)piperidine-4-carboxylic acid 2-methoxybenzylamide;
V-1007. 1-(4-Ethyl-4H-thieno[3,2-b]pyrrole-5-carbonyl)piperidine-4-carboxylic acid (3-pyrrolidine-1-ylpropyl)amide;
V-1008. (4-Ethyl-4H-thieno[3,2-b]pyrrol-5-yl)[4-(4-phenylpiperazine-1-carbonyl)piperidin-1-yl]methanone;
V-1009. (4-Ethyl-4H-thieno[3,2-b]pyrrol-5-yl)[4-(pyrrolidine-1-carbonyl)-piperidin-1-yl]methanone;
V-1010. 1-(4-Methyl-4H-thieno[3,2-b]pyrrole-5-carbonyl)piperidine-4-carboxylic acid (pyridin-2-ylmethyl)amide;
V-1011. 1-(4-Methyl-4H-thieno[3,2-b]pyrrole-5-carbonyl)piperidine-4-carboxylic acid (furan-2-ylmethyl)amide;
V-1012. 1-(4-Methyl-4H-thieno[3,2-b]pyrrole-5-carbonyl)piperidine-4-carboxylic acid 4-methoxybenzylamide;
V-1013. 1-(4-Methyl-4H-thieno[3,2-b]pyrrole-5-carbonyl)piperidine-4-carboxylic acid (2-methoxyethyl)amide;
V-1014. [4-(2,3-Dihydroindole-1-carbonyl)piperidin-1-yl][4-(4-fluorobenzyl)-4H-thieno[3,2-b]pyrrol-5-yl]-methanone;
V-1015. [4-(4-Ethylpiperazine-1-carbonyl)piperidin-1-yl][4-(4-fluorobenzyl)-4H-thieno[3,2-b]pyrrol-5-yl]methanone;
V-1016. 1-[4-(4-Fluorobenzyl)-4H-thieno[3,2-b]pyrrole-5-carbonyl]piperidine-4-carboxylic acid isopropylamide;
V-1017. [4-(4-Chlorobenzyl)-4H-thieno[3,2-b]pyrrol-5-yl][4-(4-methylpiperazine-1-carbonyl)-piperidin-1-yl]methanone;
V-1018. [4-(4-Chlorobenzyl)-4H-thieno[3,2-b]pyrrol-5-yl][4-(piperidine-1-carbonyl)-piperidin-1-yl]methanone;
V-1019. 1-[4-(4-Chlorobenzyl)-4H-thieno[3,2-b]pyrrole-5-carbonyl]piperidine-4-carboxylic acid (pyridine-3-ylmethyl)amide;
V-1020. (4-Ethyl-4H-thieno[3,2-b]pyrrol-5-yl)-[4-(4-methylpiperazine-1-carbonyl)piperidin-1-yl]methanone;
V-1021. [4-(1,4-Dioxa-8-aza-spiro[4.5]decan-8-carbonyl)piperidin-1-yl]-(4-ethyl-4H-thieno[3,2-b]pyrrol-5-yl)methanone;
V-1022. (4-Methyl-4H-thieno[3,2-b]pyrrol-5-yl)-[4-(4-phenylpiperazine-1-carbonyl)piperidin-1-yl]methanone;
V-1023. 1-[4-(4-Fluorobenzyl)-4H-thieno[3,2-b]pyrrole-5-carbonyl]piperidine-4-carboxylic acid (pyridin-2-yl)methyl amide;
V-1024. 1-[4-(4-Fluorobenzyl)-4H-thieno[3,2-b]pyrrole-5-carbonyl]piperidine-4-carboxylic acid cyclopentylamide;
V-1025. 1-[4-(4-Fluorobenzyl)-4H-thieno[3,2-b]pyrrole-5-carbonyl]piperidine-4-carboxylic acid (4-ethylphenyl)amide;
V-1026. 1-[4-(4-Fluorobenzyl)-4H-thieno[3,2-b]pyrrole-5-carbonyl]piperidine-4-carboxylic acid (2-morpholin-4-ylethyl)amide;
V-1027. [4-(4-Chlorobenzyl)-4H-thieno[3,2-b]pyrrol-5-yl]-[4-(pyrrolidin-1-carbonyl)piperidin-1-yl]methanone;
V-1028. 1-[4-(4-Chlorobenzyl)-4H-thieno[3,2-b]pyrrole-5-carbonyl]piperidine-4-carboxylic acid (2-methoxy-ethyl)amide;
V-1029. 1-[4-(4-Chlorobenzyl)-4H-thieno[3,2-b]pyrrole-5-carbonyl]piperidine-4-carboxylic acid (thiophen-2-ylmethyl)amide;
V-1030. 1-[4-(2,4-Difluorobenzyl)-4H-thieno[3,2-b]pyrrole-5-carbonyl]piperidine-4-carboxylic acid [(pyridin-2-yl)methyl]amide;
V-1031. 1-[4-(4-Fluorobenzyl)-4H-thieno[3,2-b]pyrrole-5-carbonyl]piperidine-4-carboxylic acid (pyridin-3-yl)methyl)amide;

V-1032. 1-[4-(4-Fluorobenzyl)-4H-thieno[3,2-b]pyrrole-5-carbonyl]piperidine-4-carboxylic acid 3-(diethylamino)propylamide;

V-1033. 1-[4-(4-Fluorobenzyl)-4H-thieno[3,2-b]pyrrole-5-carbonyl]piperidine-4-carboxylic acid [(4-methylphenyl)methyl]amide;

V-1034. 1-[4-(4-Fluorobenzyl)-4H-thieno[3,2-b]pyrrole-5-carbonyl]piperidine-4-carboxylic acid (2,4-dimethylphenyl)amide;

V-1035. 1-[4-(4-Fluorobenzyl)-4H-thieno[3,2-b]pyrrole-5-carbonyl]piperidine-4-carboxylic acid (3,4-dimethylphenyl)amide;

V-1036. 1-[4-(4-Fluorobenzyl)-4H-thieno[3,2-b]pyrrole-5-carbonyl]piperidine-4-carboxylic acid (2-methoxyethyl)amide;

V-1037. 1-[4-(4-Fluorobenzyl)-4H-thieno[3,2-b]pyrrole-5-carbonyl]piperidine-4-carboxylic acid [(4-fluorophenyl)methyl]amide;

V-1038. 1-[4-(4-Fluorobenzyl)-4H-thieno[3,2-b]pyrrole-5-carbonyl]piperidine-4-carboxylic acid [(1-ethylpyrrolidin-2-yl)methyl]amide;

V-1039. 1-[4-(4-Fluorobenzyl)-4H-thieno[3,2-b]pyrrole-5-carbonyl]piperidine-4-carboxylic acid (3-ethoxypropyl)amide;

V-1040. 1-[4-(4-Fluorobenzyl)-4H-thieno[3,2-b]pyrrole-5-carbonyl]piperidine-4-carboxylic acid (3-methoxypropyl)amide;

V-1041. 1-[4-(2,4-Difluorobenzyl)-4H-thieno[3,2-b]pyrrole-5-carbonyl]piperidine-4-carboxylic acid (2-N-morpholinoethyl)amide;

V-1042. 1-[4-(4-Fluorobenzyl)-4H-thieno[3,2-b]pyrrole-5-carbonyl]piperidine-4-carboxylic acid (3-N-pyrrolidinopropyl)amide;

V-1043. 1-[4-(4-Chlorobenzyl)-4H-thieno[3,2-b]pyrrole-5-carbonyl]piperidine-4-carboxylic acid hexamethylene amide;

V-1044. 1-[4-(4-Chlorobenzyl)-4H-thieno[3,2-b]pyrrole-5-carbonyl]piperidine-4-carboxylic acid tetramethylenamide;

V-1045. 1-[4-(4-Chlorobenzyl)-4H-thieno[3,2-b]pyrrole-5-carbonyl]piperidine-4-carboxylic acid [(pyridin-2-yl)methyl]amide;

V-1046. 1-[4-(4-Chlorobenzyl)-4H-thieno[3,2-b]pyrrole-5-carbonyl]piperidine-4-carboxylic acid [(tetrahydrofuran-2-yl)methyl]amide;

V-1047. 1-[4-(4-Chlorobenzyl)-4H-thieno[3,2-b]pyrrole-5-carbonyl]piperidine-4-carboxylic acid (3-methoxypropyl)amide;

V-1048. [4-(4-Fluorobenzyl)-4H-thieno[3,2-b]pyrrol-5-yl]-[4-(4-methylpiperazine-1-carbonyl)piperidin-1-yl]methanone;

V-1049. [4-(3-Chlorobenzyl)-4H-thieno[3,2-b]pyrrol-5-yl]-[4-(4-methylpiperazine-1-carbonyl)piperidin-1-yl]methanone;

V-1050. [4-(3-Fluorobenzyl)-4H-thieno[3,2-b]pyrrol-5-yl]-[4-(4-methylpiperazine-1-carbonyl)piperidin-1-yl]methanone;

V-1051. [4-(2-Fluorobenzyl)-4H-thieno[3,2-b]pyrrol-5-yl]-[4-(4-methylpiperazine-1-carbonyl)piperidin-1-yl]methanone;

V-1052. [4-(2-Chlorobenzyl)-4H-thieno[3,2-b]pyrrol-5-yl]-[4-(4-methylpiperazine-1-carbonyl)piperidin-1-yl]methanone;

V-1053. [4-(4-Methoxybenzyl)-4H-thieno[3,2-b]pyrrol-5-yl]-[4-(4-methylpiperazine-1-carbonyl)piperidin-1-yl]methanone;

V-1054. [4-(4-Dimethylaminobenzyl)-4H-thieno[3,2-b]pyrrol-5-yl]-[4-(4-methylpiperazine-1-carbonyl)piperidin-1-yl]methanone;

V-1055. [4-(3,4-Methylendioxybenzyl)-4H-thieno[3,2-b]pyrrol-5-yl]-[4-(4-methylpiperazine-1-carbonyl)piperidin-1-yl]methanone;

V-1056. [4-(4-Chlorobenzyl)-2-methyl-4H-thieno[3,2-b]pyrrol-5-yl]-[4-(4-methylpiperazine-1-carbonyl)piperidin-1-yl]methanone;

V-1057. [4-(4-Chlorobenzyl)-2,3-dimethyl-4H-thieno[3,2-b]pyrrol-5-yl]-[4-(4-methylpiperazine-1-carbonyl)piperidin-1-yl]methanone;

V-1058. [4-(4-Chlorobenzyl)-2,3,6-trimethyl-4H-thieno[3,2-b]pyrrol-5-yl]-[4-(4-methylpiperazine-1-carbonyl)piperidin-1-yl]methanone;

V-1059. (4-Pyridin-4-ylmethyl)-4H-thieno[3,2-b]pyrrol-5-yl)-[4-(4-methylpiperazine-1-carbonyl)piperidin-1-yl]methanone;

V-1060. (4-Cyclohexylmethyl)-4H-thieno[3,2-b]pyrrol-5-yl)-[4-(4-methylpiperazine-1-carbonyl)piperidine-1-yl]methanone;

V-1061. (4-Hydroxybenzyl-4H-thieno[3,2-b]pyrrol-5-yl)-[4-(4-methylpiperazine-1-carbonyl)piperidin-1-yl]methanone;

V-1062. (4-Pyridin-3-ylmethyl)-4H-thieno[3,2-b]pyrrol-5-yl)-[4-(4-methylpiperazine-1-carbonyl)piperidin-1-yl]methanone;

V-1063. [4-(2,4-Dichlorobenzyl)-4H-thieno[3,2-b]pyrrol-5-yl)][4-(4-methylpiperazine-1-carbonyl)piperidine-1-yl]methanone;

V-1064. [4-(2,4-Dimethoxybenzyl-4H-thieno[3,2-b]pyrrol-5-yl)][4-(4-methylpiperazine-1-carbonyl)piperidin-1-yl]methanone;

V-1065. [4-(2,4-Difluorobenzyl-4H-thieno[3,2-b]pyrrol-5-yl)][4-(4-methylpiperazine-1-carbonyl)piperidin-1-yl]methanone;

V-1066. 4-(Benzyl-4H-thieno[3,2-b]pyrrol-5-yl)[4-(4-methylpiperazine-1-carbonyl)piperidin-1-yl]methanone;

V-1067. [4-(3,5-Dichlorobenzyl-4H-thieno[3,2-b]pyrrol-5-yl)][4-(4-methylpiperazine-1-carbonyl)piperidin-1-yl]methanone;

V-1068. [(4-Bromobenzyl-4H-thieno[3,2-b]pyrrol-5-yl)][4-(4-methylpiperazine-1-carbonyl)piperidin-1-yl]methanone;

V-1069. {4-[4-(2-Hydroxyethoxy)benzyl]-4H-thieno[3,2-b]pyrrol-5-yl}[4-(4-methylpiperazine-1-carbonyl)piperidin-1-yl]methanone;

VI-1001. 3,4,5,6-Tetrahydro-2H-[1,2']bipyridinyl-4,4'-carboxylic acid 4'-[(4-ethoxyphenyl)amide] 4-[(3-phenylpropyl)amide];

VI-1002. 3,4,5,6-Tetrahydro-2H-[1,2']bipyridinyl-4,4'-carboxylic acid 4-[(3,4-dimethylphenyl)amide] 4'-[(4-ethoxyphenyl)amide];

VI-1003. 3,4,5,6-Tetrahydro-2H-[1,2']bipyridinyl-4,4'-carboxylic acid 4-[(3,5-dimethylphenyl)amide] 4'-[(4-ethoxyphenyl)amide];

VI-1004. 3,4,5,6-Tetrahydro-2H-[1,2']bipyridinyl-4,4'-carboxylic acid 4-[(3,5-dimethylphenyl)amide] 4'-[(4-ethoxyphenyl)amide];

VI-1005. 3,4,5,6-Tetrahydro-2H-[1,2']bipyridinyl-4,4'-carboxylic acid 4'-[(4-ethoxyphenyl)amide] 4-[(4-isopropylphenyl)amide];

VI-1006. 3,4,5,6-Tetrahydro-2H-[1,2']bipyridinyl-4,4'-carboxylic acid 4'-[(4-ethoxyphenyl)amide] 4-[(2-methoxyphenyl)amide];

VI-1007. 3,4,5,6-Tetrahydro-2H-[1,2']bipyridinyl-4,4'-carboxylic acid 4'-[(4-ethoxyphenyl)amide] 4-[(4-fluorophenyl)amide];

VI-1008. 4-(Morpholine-4-carbonyl)-3,4,5,6-tetrahydro-2H-[1,2']bipyridinyl-4-carboxylic acid (4-ethoxyphenyl)amide;

VI-1009. 3,4,5,6-Tetrahydro-2H-[1,2']bipyridinyl-4,4'-carboxylic acid 4-(4-chlorobenzylamide) 4'-[(3-methoxyphenyl)amide];

VI-1010. 3,4,5,6-Tetrahydro-2H-[1,2']bipyridinyl-4,4'-carboxylic acid 4'-[(3-methoxyphenyl)amide] 4-[(thiophen-2-ylmethyl)amide];

VI-1011. 3,4,5,6-Tetrahydro-2H-[1,2']bipyridinyl-4,4'-carboxylic acid 4-cyclopentylamide 4'-[(3-methoxyphenyl)amide];

VI-1012. 3,4,5,6-Tetrahydro-2H-[1,2']bipyridinyl-4,4'-carboxylic acid 4'-[(3-methoxyphenyl)amide] 4-(phenethylamide);

VI-1013. 3,4,5,6-Tetrahydro-2H-[1,2']bipyridinyl-4,4'-carboxylic acid 4'-[(2-fluorophenyl)amide] 4-[(4-isopropylphenyl)amide];

VI-1014. 3,4,5,6-Tetrahydro-2H-[1,2]bipyridinyl-4,4'-carboxylic acid 4'-[(2-fluorophenyl)amide] 4-(3-methoxybenzylamide);

VI-1015. 4'-(Morpholine-4-carbonyl)-3,4,5,6-tetrahydro 2H-[1,2]bipyridinyl-4-carboxylic acid 4-fluorobenzylamide;

VI-1016. 4'-(Morpholine-4-carbonyl)-3,4,5,6-tetrahydro-2H-[1,2']bipyridinyl-4-carboxylic acid (benzo[1,3]dioxol-5-ylmethyl)amide;

VI-1017. 4'-(Pyrrolidine-1-carbonyl)-3,4,5,6-tetrahydro-2H-[1,2']bipyridinyl-4-carboxylic acid 2-methoxybenzylamide;

VI-1018. 4'-(Pyrrolidine-1-carbonyl)-3,4,5,6-tetrahydro-2H-[1,2']bipyridinyl-4-carboxylic acid (2,4-dimethylphenyl)amide;

VI-1019. 4'-(Pyrrolidine-1-carbonyl)-3,4,5,6-tetrahydro-2H-[1,2']bipyridinyl-4-carboxylic acid (4-ethoxyphenyl)amide;

VI-1020. 4'-(Pyrrolidine-1-carbonyl)-3,4,5,6-tetrahydro-2H-[1,2']bipyridinyl-4-carboxylic acid (3-methoxyphenyl)amide;

VI-1021. 4'-(Piperidine-1-carbonyl)-3,4,5,6-tetrahydro-2H-[1,2']bipyridinyl-4-carboxylic acid phenylamide;

VI-1022. 4'-(Piperidine-1-carbonyl)-3,4,5,6-tetrahydro-2H-[1,2']bipyridinyl-4-carboxylic acid 4-bromobenzylamide;

VI-1023. 4'-(Piperidine-1-carbonyl)-3,4,5,6-tetrahydro-2H-[1,2']bipyridinyl-4-carboxylic acid 4-bromobenzylamide;

VI-1024. 3,4,5,6-Tetrahydro-2H-[1,2']bipyridinyl-4,4'-carboxylic acid 4-(2-methoxybenzylamide) 4'-[(2-methoxyphenyl)amide];

VI-1025. 3,4,5,6-Tetrahydro-2H-[1,2]bipyridinyl-4,4'-carboxylic acid 4-[(2,4-dimethylphenyl)amide] 4'-[(2-methoxyphenyl)amide];

VI-1026. 3,4,5,6-Tetrahydro-2H-[1,2']bipyridinyl-4,4'-carboxylic acid 4-[(2,3-dihydrobenzo[1,4]dioxin-6-yl)amide] 4'-[(2-methoxyphenyl)amide];

VII-1001. 1-Tosyl-1,2,3,4-tetrahydroquinoline-6-carboxylic acid (2,4,6-mesityl)amide;

VII-1002. 1-Methylsulfonyl-1,2,3,4-tetrahydroquinoline-6-carboxylic acid methylamide;

VII-1003. 1-Methylsulfonyl-1,2,3,4-tetrahydroquinoline-6-carboxylic acid 4-methoxybenzylamide;

VII-1004. 1-Methylsulfonyl-1,2,3,4-tetrahydroquinoline-6-carboxylic acid (pyridin-2-ylmethyl)amide;

VII-1005. 1-Methylsulfonyl-1,2,3,4-tetrahydroquinoline-6-carboxylic acid (benzo[1,3]dioxol-5-yl)amide;

VII-1006. [(1-Methylsulfonyl-1,2,3,4-tetrahydroquinolin-6-yl)morpholin-4-yl]methanone;

VII-1007. [4-(4-Fluorophenyl)piperazin-1-yl]-(1-methylsulfonyl-1,2,3,4-tetrahydroquinolin-6-yl)methanone;

VII-1008. 1-Phenylsulfonyl-1,2,3,4-tetrahydroquinoline-6-carboxylic acid ethylamide;

VII-1009. 1-Phenylsulfonyl-1,2,3,4-tetrahydroquinoline-6-carboxylic acid 4-methylbenzylamide;

VII-1010. 1-Phenylsulfonyl-1,2,3,4-tetrahydroquinoline-6-carboxylic acid [2-(3,4-dimethoxyphenyl)ethyl]amide;

VII-1011. 1-Phenylsulfonyl-1,2,3,4-tetrahydroquinoline-6-carboxylic acid (pyridin-3-ylmethyl)amide;

VII-1012. 1-Phenylsulfonyl-1,2,3,4-tetrahydroquinoline-6-carboxylic acid (4-fluorophenyl)amide;

II-1013. (1-Phenylsulfonyl-1,2,3,4-tetrahydroquinolin-6-yl)pyrrolidin-1-ylmethanone;

VII-1014. 1-Tosyl-1,2,3,4-tetrahydroquinoline-6-carboxylic acid (4-methoxyphenyl)amide;

VII-1015. 1-(4-Chlorophenylsulfonyl)-1,2,3,4-tetrahydroquinoline-6-carboxylic acid ethylamide;

VII-1016. 1-(4-Chlorophenylsulfonyl)-1,2,3,4-tetrahydroquinoline-6-carboxylic acid (furan-2-ylmethyl)amide;

VII-1017. 1-(4-Chlorophenylsulfonyl)-1,2,3,4-tetrahydroquinoline-6-carboxylic acid (3,4-dimethylphenyl)amide;

VII-1018. [1-(4-Chlorophenylsulfonyl)-1,2,3,4-tetrahydroquinolin-6-yl]piperidin-1-ylmethanone;

VII-1019. 1-(4-Chlorophenylsulfonyl)-1,2,3,4-tetrahydroquinoline-6-carboxylic acid (2-morpholin-4-ylethyl)amide;

VII-1020. 1-(4-Bromophenylsulfonyl)-1,2,3,4-tetrahydroquinoline-6-carboxylic acid p-tolylamide;

VII-1021. 1-(4-Bromophenylsulfonyl)-1,2,3,4-tetrahydroquinoline-6-carboxylic acid (4-methylbenzyl)amide;

VII-1022. 1-(4-Bromophenylsulfonyl)-1,2,3,4-tetrahydroquinoline-6-carboxylic acid cyclohexylamide;

VII-1023. 1-Ethylsulfonyl-1,2,3,4-tetrahydroquinoline-6-carboxylic acid (2-methoxyethyl)amide;

VII-1024. 1-Ethylsulfonyl-1,2,3,4-tetrahydroquinoline-6-carboxylic acid (pyridin-3-ylmethyl)amide;

VII-1025. 1-Ethylsulfonyl-1,2,3,4-tetrahydroquinoline-6-carboxylic acid (2-fluorophenyl)amide;

VII-1026. (1-Ethylsulfonyl-1,2,3,4-tetrahydroquinoline-6-yl)-morpholin-4-ylmethanone;

VIII-1001. Cyclohexanecarboxylic acid (3-benzo[d]thiazol-2-yl-6-methyl-4,5,6,7-tetrahydrothieno[2,3-c]pyridin-2-yl)amide;

VIII-1002. N-(3-Benzo[d]thiazol-2-yl-6-methyl-4,5,6,7-tetrahydrothieno[2,3-c]pyridin-2-yl)propionylamide;

VIII-1003. Cyclopropanecarboxylic acid (3-benzo[d]thiazol-2-yl-6-methyl-4,5,6,7-tetrahydrothieno[2,3-c]pyridin-2-yl)amide;

VIII-1004. N-(3-Benzo[d]thiazol-2-yl-6-methyl-4,5,6,7-tetrahydrothieno[2,3-c]pyridin-2-yl)terephthalic acid methyl ester;

VIII-1005. N-(3-Benzo[d]thiazol-2-yl-6-ethyl-4,5,6,7-tetrahydrothieno[2,3-c]pyridin-2-yl)-4-chlorobenzamide;

VIII-1006. Thiophene-2-carboxylic acid (3-benzo[d]thiazol-2-yl-6-ethyl-4,5,6,7-tetrahydrothieno[2,3-c]pyridin-2-yl)amide;

VIII-1007. N-(3-Benzo[d]thiazol-2-yl-6-ethyl-4,5,6,7-tetrahydrothieno[2,3-c]pyridin-2-yl)-4-methoxybenzamide;

VIII-1008. N-(3-Benzo[d]thiazol-2-yl-6-benzyl-4,5,6,7-tetrahydrothieno[2,3-c]pyridin-2-yl)-acetamide;

VIII-1009. N-(3-Benzo[d]thiazol-2-yl-6-benzyl-4,5,6,7-tetrahydrothieno[2,3-c]pyridin-2-yl)-isobutyramide;

VIII-1010. Furan-2-carboxylic acid (3-benzo[d]thiazol-2-yl-6-benzyl-4,5,6,7-tetrahydrothieno[2,3-c]pyridin-2-yl)amide;

VIII-1011. N-(3-Benzo[d]thiazol-2-yl-6-isopropyl-4,5,6,7-tetrahydrothieno[2,3-c]pyridin-2-yl)-4-fluorobenzamide;

VIII-1012. N-(3-Benzo[d]thiazol-2-yl-6-isopropyl-4,5,6,7-tetrahydrothieno[2,3-c]pyridin-2-yl)acetamide;

VIII-1013. Thiophene-2-carboxylic acid (3-benzo[d]thiazol-2-yl-6-isopropyl-4,5,6,7-tetrahydrothieno[2,3-c]pyridin-2-yl)amide;

VIII-1014. 2,3-Dihydrobenzo[b][1,4]dioxine-6-carboxylic acid (6-acetyl-3-benzo[d]thiazol-2-yl-4,5,6,7-tetrahydrothieno[2,3-c]pyridin-2-yl)amide;

VIII-1015. Furan-2-carboxylic acid (6-acetyl-3-benzo[d]thiazol-2-yl-4,5,6,7-tetrahydrothieno[2,3-c]pyridin-2-yl)amide;

VIII-1016. Cyclohexanecarboxylic acid (6-acetyl-3-benzo[d]thiazol-2-yl-4,5,6,7-tetrahydrothieno[2,3-c]pyridin-2-yl)amide;

VIII-1017. N-(6-Acetyl-3-benzo[d]thiazol-2-yl-4,5,6,7-tetrahydrothieno[2,3-c]pyridin-2-yl)-2-phenylacetamide;

VIII-1018. Benzo[d]thiazole-6-carboxylic acid (6-acetyl-3-benzo[d]thiazol-2-yl-4,5,6,7-tetrahydrothieno[2,3-c]pyridin-2-yl)amide;

VIII-1019. N-(6-Acetyl-3-benzo[d]thiazol-2-yl-4,5,6,7-tetrahydrothieno[2,3-c]pyridin-2-yl)-2-(4-fluorophenylsulfanyl)acetamide VIII-1020. 2-Acetylamino-3-benzo[d]thiazol-2-yl-4,7-dihydro-5H-thieno[2,3-c]pyridine-6-carboxylic acid ethyl ester;

VIII-1021. 3-Benzo[d]thiazol-2-yl-2-(4-methoxybenzoylamino)-4,7-dihydro-5H-thieno[2,3-c]pyridine-6-carboxylic acid ethyl ester;

VIII-1022. 3-Benzo[d]thiazol-2-yl-2-propionylamino-4,7-dihydro-5H-thieno[2,3-c]pyridine-6-carboxylic acid ethyl ester;

VIII-1023. 3-Benzo[d]thiazol-2-yl-2-(3-methoxybenzoylamino)-4,7-dihydro-5H-thieno[2,3-c]pyridine-6-carboxylic acid ethyl ester;

VIII-1024. 3-Benzo[d]thiazol-2-yl-2-[(thiophen-2-carbonyl)amino]-4,7-dihydro-5H-thieno[2,3-c]pyridine-6-carboxylic acid ethyl ester;

VIII-1025. N-(3-Benzo[d]thiazol-2-yl)-6-isopropyl-4,5,6,7-tetrahydrothieno[2,3-c]pyridin-2-yl)terephthalic acid methyl ester;

VIII-1026. N-(3-(Benzo[d]thiazol-2-yl)-6-methyl-4,5,6,7-tetrahydrothieno[2,3-c]pyridin-2-yl)-3-trifluoromethyl-benzamide and pharmaceutically acceptable salts thereof.

The subject of the invention is also use of compounds of the general formulas I-VIII, which exhibit physiological activity, that is: the property to influence efficiently on the embryonal signalling systems, in particular, to block Hh-signalling cascade, that makes it possible to use them as drug substances for humans and warm-blooded animals for treatment of diseases associated with abberant activity of Hh signalling system.

The following subject of the invention is a drug substance exhibiting physiological activity to act effectively on embryonal signalling systems and block the Hh-signal cascade which is a compound of the general formulas I-VIII for preparation of pharmaceutical compositions and medicaments.

The next subject of the invention is a novel pharmaceutical composition exhibiting the property to act effectively on embryonal signalling systems, in particularly, to block Hh-signalling cascade. As an active ingredient the said composition comprises pharmaceutically effective amount of a compound of the general formulas I-VIII.

The purpose of the present invention is also a method for preparation of a novel pharmaceutical composition comprising as an active ingredient, at least, one of compounds of the general formulas I-VIII, which are inhibitors of Hh signalling cascade. The method consists in mixing of physiologically effective amount of active ingredient with an inert in relation to the active ingredient excipients and/or solvents, with the subsequent pelletizing, granulation, capsulating, suspending, dissolution or diluting and placing into suitable packing. The distinctive feature of the method consists in utilization as an active ingredient, at least, one of the compounds of the general formulas I-VIII.

The further subject of the invention is a medicament in the form of tablets, capsules or injections, placed in pharmaceutically acceptable packing and comprising a drug substance or pharmaceutical composition including, at least, one of the compounds of the general formulas I-VIII, for prophylaxis and treatment of various diseases, associated with abberant activity of Hh signalling system.

The further subject of the invention is a method for treatment and prophylaxis of oncological diseases of humans and warm-blooded animals. The method consists in use of novel drug substances comprising as an active ingredient an effective amount of, at least, one of the compounds of the general formulas I-VIII. The method is intended for treatment of malignant neoplasms, such as prostate cancer, intestine cancer, hepar cancer, pancreatic gland cancer, stomack cancer, cervix cancer, endometrium cancer, brain cancer, urinary bladder cancer, ovary cancer, android glands cancer, cervix cancer, head cancer, skin cancer (including melanoma and basal carcinoma), white blood cells cancer (including lymphoma and leukaemia), esophagus cancer, breast cancer, soft and connective tissues cancer, lung cancer (including parvicellular and nonparvicellular carcinoma), adrenal cortex cancer, kidney cancer, bones cancer, and thyroid cancer, glioblastoma, mesothelioma, renal and gastro-carcinoma, sarcoma, osteosarcoma, choreacarcinoma, basal carcinoma and testicular seminoma, rhabdomyosarcoma and other malignant neoplasms.

The method is mainly intended for treatment of oncological diseases in pathogenesis of which abberant activation of Hh signalling cascade plays an essential role, in particular, for treatment of basal carcinoma, hepar cancer, pancreas cancer, medulloblastoma, lung cancer, bones cancer, breast cancer, brain tumour, prostate cancer and rhabdomyosarcoma.

The further subject of the invention is a method of treatment and prophylaxis of psoriasis. The method consists in use of a medicament comprising an effective amount of an active ingredient, which is, at least, one of the compounds of the general formulas I-VIII.

The next subject of the invention is also therapeutic cocktail for treatment of oncologic diseases, comprising as one of the components a medicament, prepared on the basis of a pharmaceutical composition, an active ingredient of which is, at least, one of the compounds of the general formulas I-VIII or its pharmaceutically acceptable salt. Therapeutic cocktails for treatment of oncologic diseases (in particular, bazal carcinoma, hepar cancer, pancreas cancer, medulloblastoma, lung cancer, bones cancer, breast cancer, brain tumors, prostate cancer and rhabdomyosarcoma) along with the drug substances disclosed in the invention, may include other antitumor medicaments, for example, such cytostatic and cytotoxic drugs as Taxol, Taxotere, Adriamycin, Daunomycin, winkle-alkaloids (Vinblastine, Vincristine and similar to), Etoposide, Cis-platine (and other metal complexes), metabolic antagonists (for example, Methotreate and others), protein kinase inhibitors (for example, Sorafenib, Imatinib and similar to), pharnesil transferase inhibitors (for example, Arglabine and similar to), hormonal agents, topoisomerasa, aromatase and telomerase inhibitors, and nucleoside analogues, and oligonucleotides, monoclonal antibodies, proteines and stem cells and others. Besides, the combined therapy in parallel with employment of medicaments according to the invention may include radiotherapy, photodynamic therapy and similar to.

The further subject of the invention is physiologically active compounds of the general formulas I-VIII, exhibiting the property to inhibit various elements of Hh-signalling cascade, that makes possible to use them as "molecular instruments" for investigation of peculiarities of embrion signalling cascades, in which proteins Hh, Ptc and Smo play the key role.

The further subject of the invention is method for preparation of compounds of the general formulas I-VIII.

According to the invention the compounds of the general formula I could be prepared as shown in scheme 1. Thus, the reaction of chloroacylacetic esters a1 with hydrazines gives substituted α-chlorohydrazones a2, the latter by the action of β-dicarbonyl compounds could be converted to the corresponding acylpyrazolecarboxylates a3, which give pyrazolo[3,4-d]pyridazines a4 under the action of hydrazine. Alkylation of a4 by various (α-γ)-halogencarboxylates gives rise to the series of esters a5. Base hydrolysis of a5 and subsequent interaction of obtained acids with various primary and secondary amines in the presence of condensing agents give rise to the compounds of the general formula I.

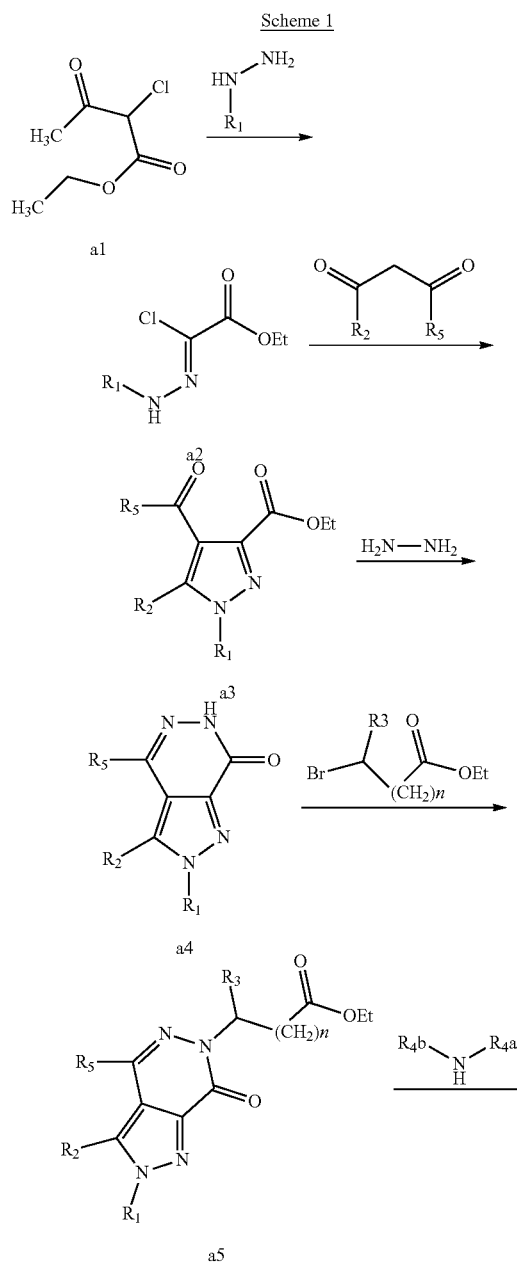

-continued

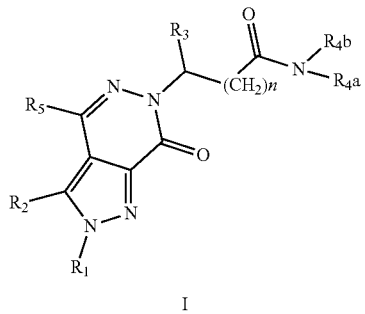

I

According to the invention compounds of the general formula II could be prepared as shown in scheme 2.

Thus, the starting N-substituted pyrazolin-3-ones were successively subjected to deoxychlorination and nitration and obtained, as a result of it, 2-substituted 3-chloro-4-nitropyrazolines b1 by the action of mercaptoacetic acid ester were converted into pyrazolines b2. Series of 1-substituted 1,4-dihydropyrazolo[3,4-b][1,4]thiazin-5-ones b3 was prepared by the action of dithionite natrium excess at pyrazolines b2 in base medium. Alkylation of heterocycles b3 by various (α-γ)-halogencarboxylates gives rise to the series of esters b4. Base hydrolysis of b4 and subsequent interaction of the obtained acids with various primary and secondary amines in the presence of condensing agents give rise to the compounds of the general formula II.

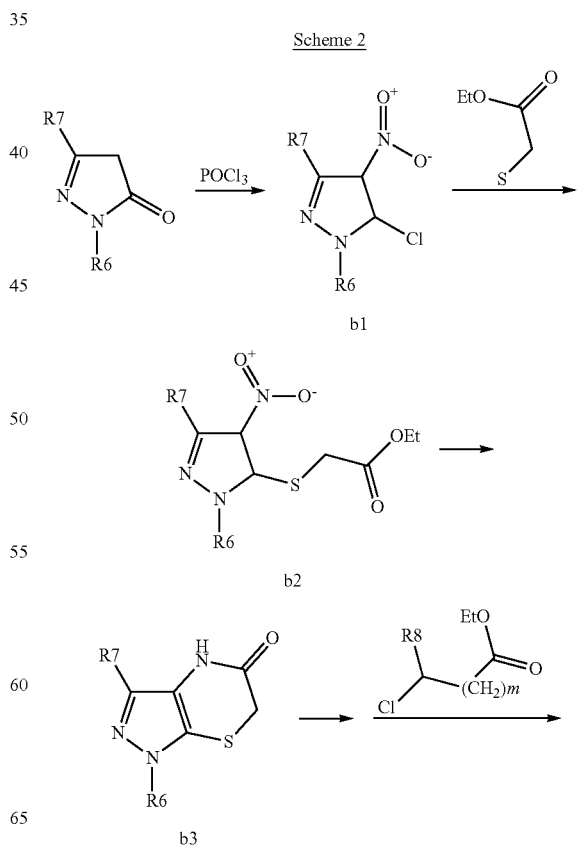

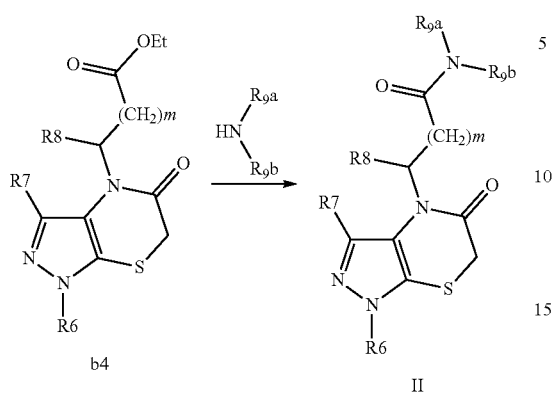

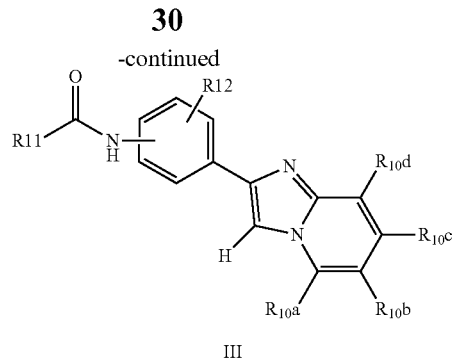

According to the invention compounds of the general formula III could be prepared as shown in scheme 3.

Thus, condensation of 2-aminopyridines c1 with nitrophenacylbromides c2 gave a series of nitroarylated imidazo[1,2-a]pyridines c3, reduction of nitro group of which and subsequent acylation of the prepared anilines c4 gave rise to the compounds of the general formula III.

According to the invention compounds of the general formula IV could be prepared as shown in scheme 4.

Scheme 3

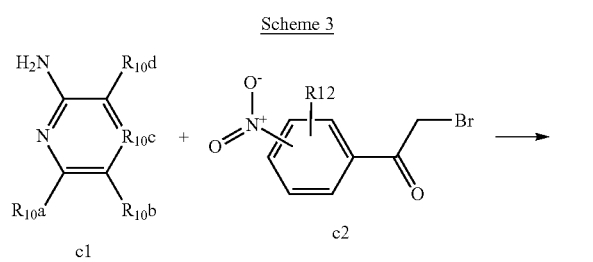

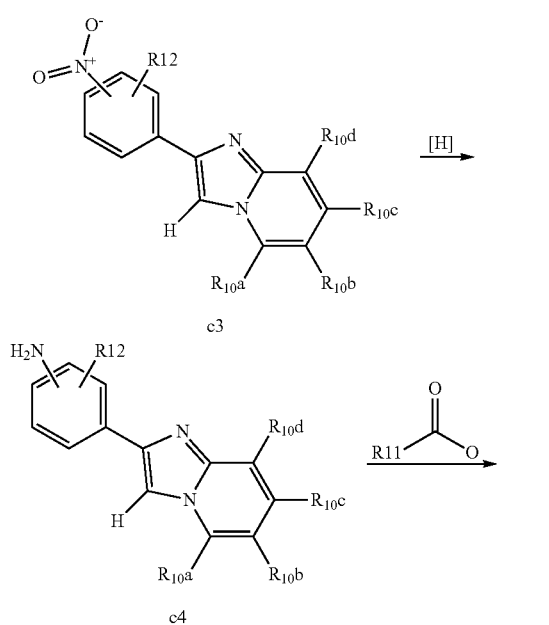

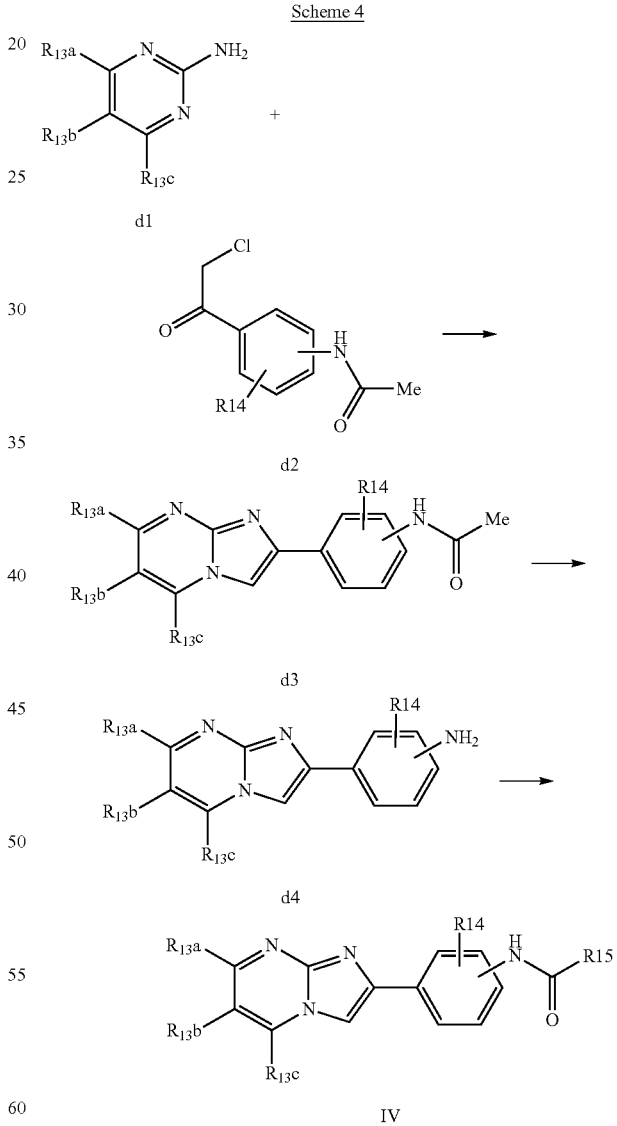

Thus, condensation of 2-aminopyrimidines d1 with acetamidophenacyl halides d2 leads to the series of acetamidoarylated imidazo[1,2-a]pyrimidines d3, deacylation of which and subsequent acylation of prepared anilines d4 give rise to amides of the general formula IV.

According to the invention compounds of the general formula V could be prepared as shown in scheme 5.

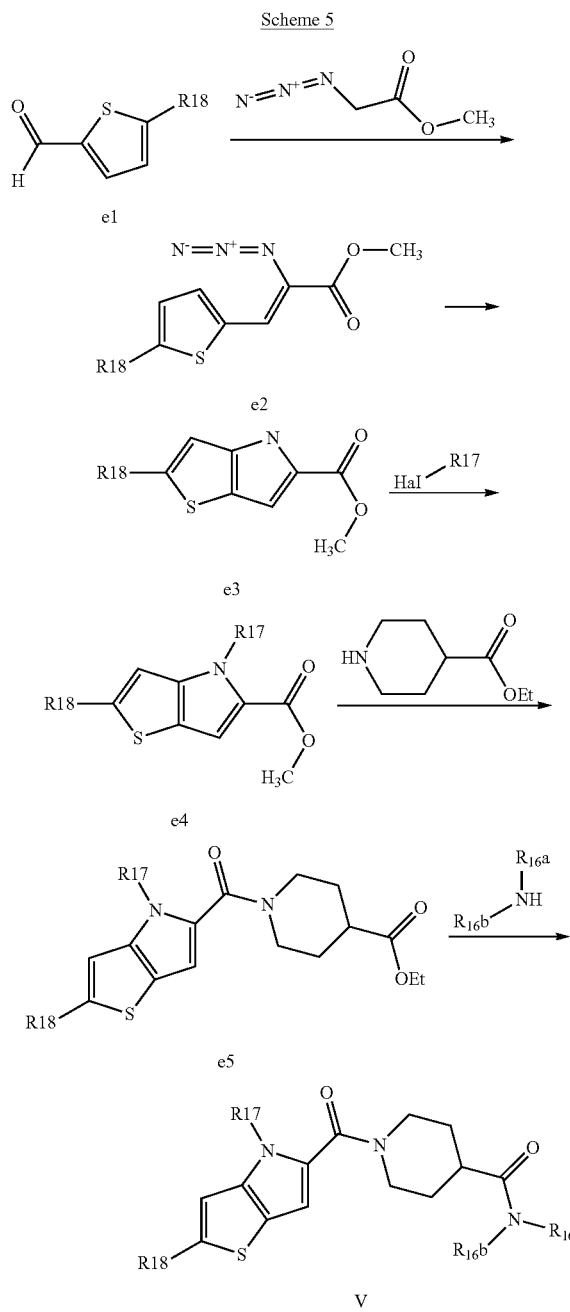

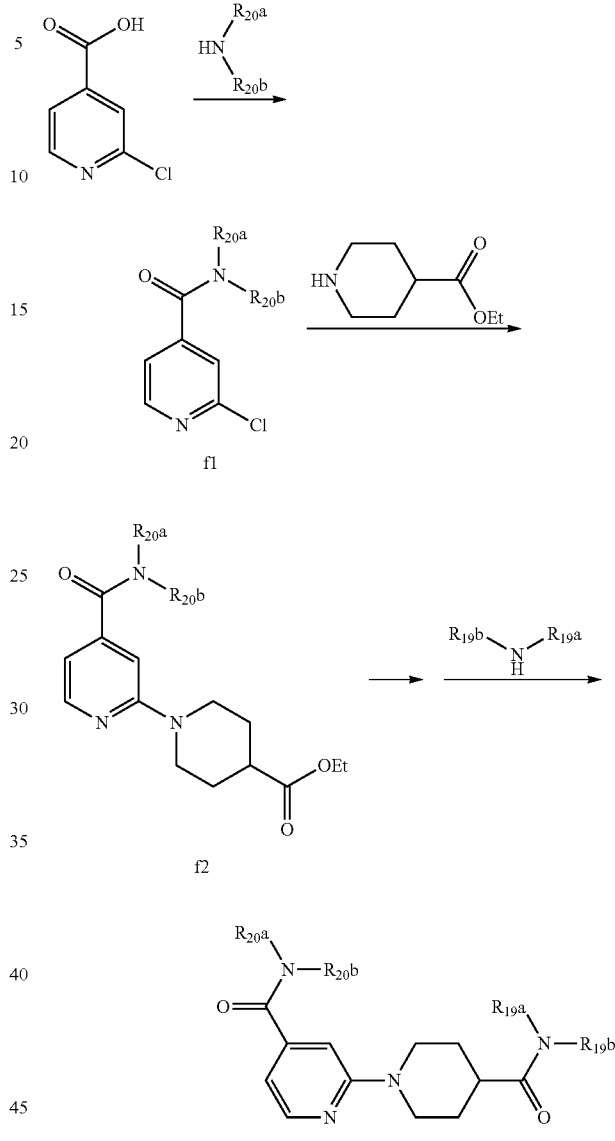

Thus, 2-azido-3-thien-2-ylacrylic esters e2 prepared by condensation of substituted 2-formylthiophenes e1 with ethyl azidoacetate are subjected to intramolecular cyclization at heating and give thieno[3,2-b]pyrroles e3. N-Alkylation of e3 and subsequent interaction of e4 with ethyl isonipecotate give a series of amidoesters e5. Base hydrolysis of e5 and subsequent interaction of the obtained acids with various primary and secondary amines in the presence of condensing agents give rise to the compounds of the general formula V.

According to the invention compounds of the general formula VI could be prepared as shown in scheme 6.

Thus, interaction of 2-chloroisonicotinic acid with various primary and secondary amines in the presence of condensing agents leads to amides of the general formula f1, the latter with isonipecotic esters give amidoesters f2. Base hydrolysis of f2 and subsequent interaction of the obtained acids with various primary and secondary amines in the presence of condensing agents give rise to compounds of the general formula VI.

According to the invention compounds of the general formula VII could be prepared as shown in scheme 7.

Thus, interaction of various sulfonyl chlorides with 6-methyl-1,2,3,4-tetrahydroquinoline gives sulfamides g1. Oxidation of methyl group in these compounds leads to the series of corresponding acids g2, the latter with various primary and secondary amines in the presence of condensing agents give rise to compounds of the general formula VII.

Scheme 7

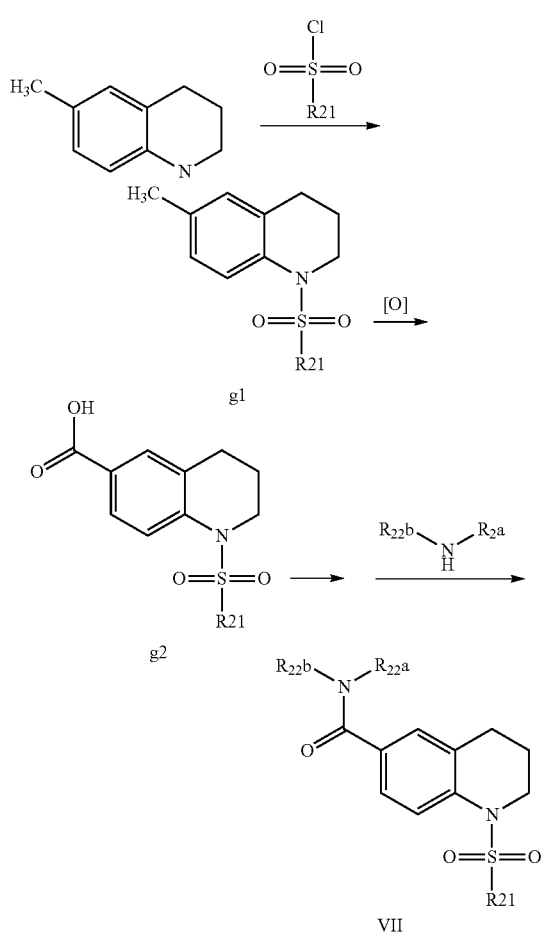

According to the invention compounds of the general formula VIII could be prepared as shown in scheme 8.

Thus, condensation of N-substituted piperidin-4-ones with benzoazolylacetonitriles h1 and sulfur gives 2-amino-4,5,6,7-tetrahydrothieno[2,3-c]pyridines h2, acylation of which leads to compounds of the general formula VIII.

Scheme 8

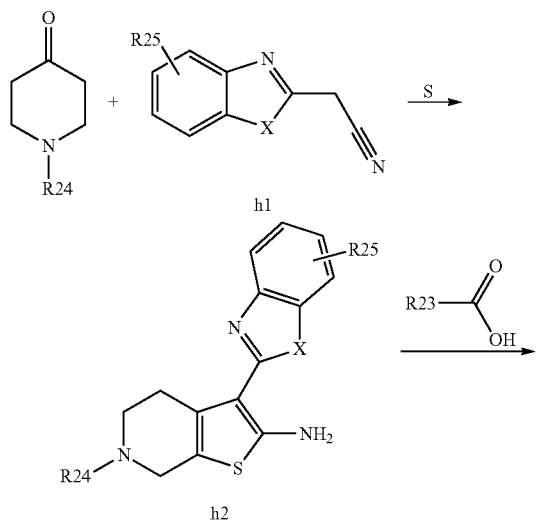

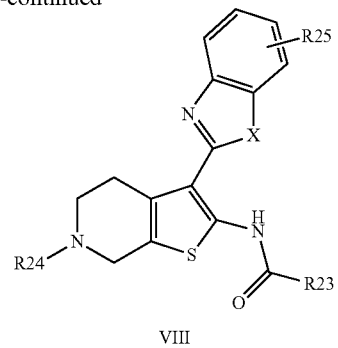

VIII

BEST EMBODIMENT OF THE INVENTION

The invention is illustrated by the following figures:

FIG. 1 Concentration dependences of inhibition of alkaline phosphatase induction caused by SHh (0.3 μg/ml) in cells C3H10T1/2 by tested compounds. (■—concentration dependence for III-1004; ▲—for III-1029; ▼—for VII-1001; ♦—IV—for 1004; ●—for V-1027).

Figure 2:
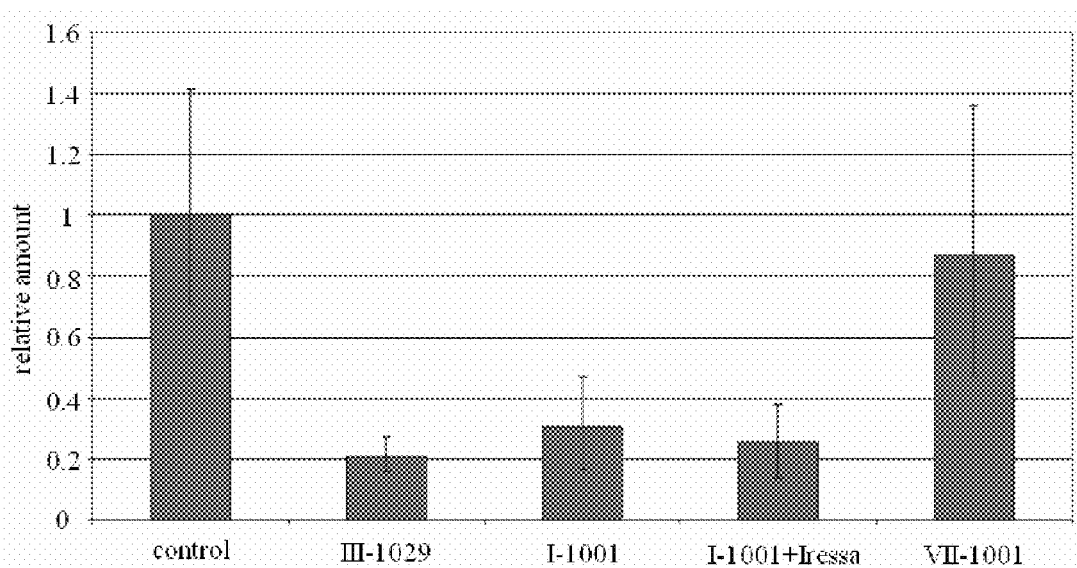

FIG. 2. Examples of suppression of the transcription factor Gli1 induction in the cell culture of human tumors Panc1 by compounds of the general formulas I-VIII.

Figure 3:
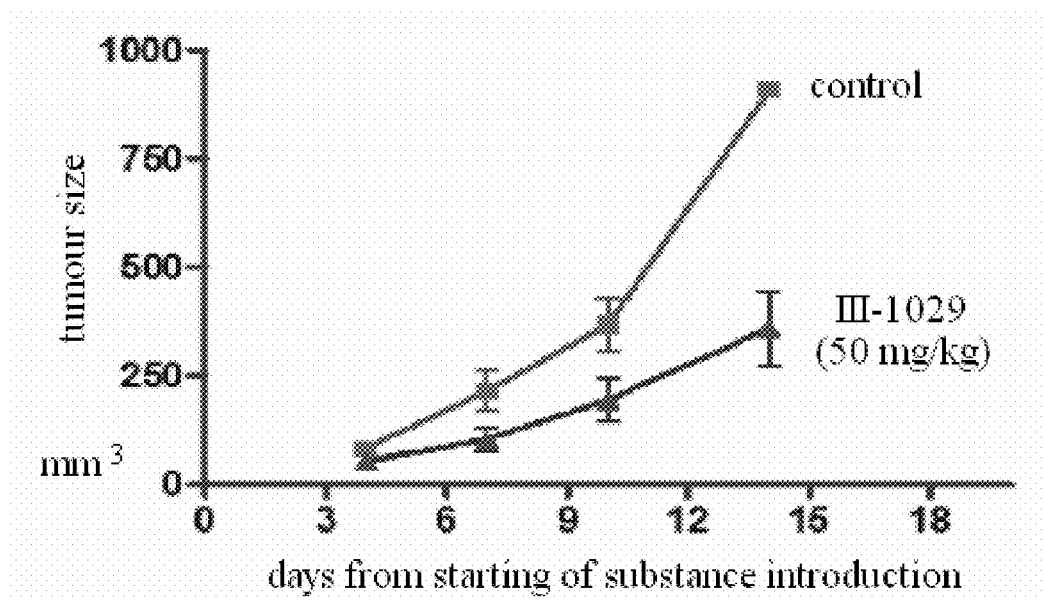

FIG. 3. Example of antitumour action of compound III-1029 on human's pancreatic carcinoma Panc1, inoculated to immunodeficient transgenic (naked) mice of Balb-c/nude line.

Figure 4:
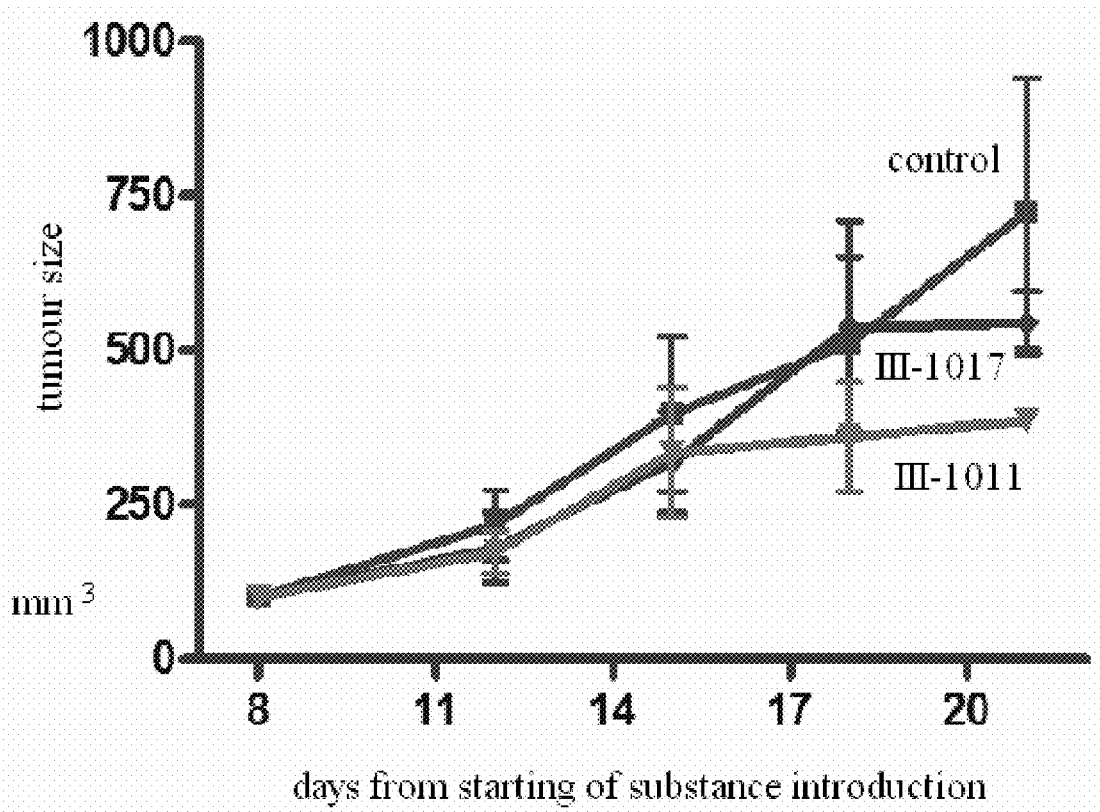

FIG. 4. Example of antitumour action of compound III-1017 and III-1011 on human's pancreatic carcinoma Panc1, inoculated to immunodeficient transgenic (naked) mice of Balb-c/nude line.

Below the invention is described by means of specific examples, which illustrate but not limit the scope of the invention.

All solvents and reagents used were received from commercial sources, such as Acros (Belgium), Sigma-Aldrich (USA), Lancaster (England) and ChemDiv (USA). Melting points were determined with instrument Buchi (Switzerland), model B-520. $^1H$ and $^{13}C$ NMR spectra were measured with spectrometer Gemini-300 (300 MHz) (Varian) in $CDCl_3$, chemical shifts are given in δ (m.d.). Internal standard is tetramethylsilane.

The basic product level was controlled by HPLC method with Shimadzu instrument 10-AV (colomn Luna-C18, Phenomenex, 25 cm×4.6 mm, UV detecting at 215 and 254 nm) and LCMS with Applied Biosystems instrument (Shimadzu 10-AV LC, Gilson-215 automatic delivery of the sample, mass spectrometer API 150EX, detectors UV (215 and 254 nm) and ELS, colomn Luna-C18, Phenomenex, 5 cm×2 mm).

Analytical TLC was carried out using Silufol $UV_{254}$ (5 sm×15 sm) (Kavalier, Czech Republic) or glass plates with 0.25 mm silica gel 60 $F_{254}$ (Merck, Germany) layer. Visualisation was performed by UV light at 254 nm. Silica gel 5-40 μm (Chemapol, Czech Republic) and 63 μm (EM Science, USA) were used for chromatographic purification of compounds. According to LCMS data all synthesized compounds were of 95% purity.

EXAMPLE 1

Screening of the Compound Library

C3H10T1/2 Cells were used for identification of inhibitors of SHh-protein signaling cascade. SHh-protein activates C3H10T1/2 cells, that leads to their osteogenic differentiation [1] Kinto N., Iwamoto M., Enomoto-Iwamoto M., Noji S., Ohuchi H., Yoshioka H., Kataoka H., Wada Y., Yuhao G., Takahashi H. E., Yoshiki S., Yamaguchi A. Fibroblasts expressing Sonic hedgehog induce osteoblast differentiation and ectopic bone formation. *FEBS Lett.* 1997; 404(2-3): 319-23. 2) Spinella-Jaegle S., Rawadi G., Kawai S., Gallea S., Faucheu C., Mollat P., Courtois B., Bergaud B., Ramez V., Blanchet A. M., Adelmant G., Baron R., Roman-Roman S. Sonic hedgehog increases the commitment of pluripotent mesenchymal cells into the osteoblastic lineage and abolishes adipocytic differentiation. *J. Cell Sci.* 2001; 114(Pt 11): 2085-94] and, in particular, to expression enhancement of alkaline phosphatase enzyme.

The cells were cultivated in DMEM medium with 10% embryonal calfish serum in incubator at 37° C., 100% humidity and 5% $CO_2$ content. The cells were placed in 384-well plates and left for night. On the next day the tested compounds in concentration of 10 μM were added to the cells, incubated for 30 min, then recombinant (R & D Systems, USA) SHh protein in concentration of 0.3 μg/ml was added and incubation was continued for 3 days. Cells with DMSO instead of a test compound and cells without SHh protein were used as test control. For determination of the cell alkaline phosphatase activity the cells were lysed in the buffer containing 0.2% Triton-X100, lisates were incubated together with pro-luminescent substrate CSPD (Applied Biosystems, USA) and the resultant luminescence was measured using reader VICTOR²V (PerkinElmer, USA).

For elimination of compounds nonspecifically inhibiting alkaline phosphatase the cells were primarily incubated with SHh protein for 3 days, lysed and before determination of alkaline phosphatase activity the tested compounds were added. For elimination of cytotoxic compounds the cells were incubated together with the tested compounds and SHh proteins for 3 days and the amount of living cells in the corresponding well using reagent CellTiter-Blue (Promega, USA) was determined.

EXAMPLE 2

Inhibiting Activity (IC50) Determination

The ability of the compounds to inhibit Hh-signalling cascade was determined using C3H10T1/2 cells in 384-well plates as described in example 1. The compounds were added in triplicates in various concentrations, prepared by multiple dilution of starting solutions (concentration dependences of cell alkaline phosphatase inhibition induced by the addition of tested compounds are shown in FIG. 1). Activity of the compounds was characterized by their concentrations produced half maximal inhibition of stimulation of cell alkaline phosphatase SHh (IC50). Activity values for some inhibitors are presented in Table 2.

Inhibiting activity of the compounds given in Table 2 is presented in the following manner:

A—$IC_{50}$: <500 nM; B—$IC_{50}$: <5.0 μM; C—$IC_{50}$: <50 μM; D—$IC_{50}$: >50 μM

TABLE 2

| IC50 values for tested compounds | |
|---|---|
| No of compound | IC50 |
| I-1001 | A |
| I-1002 | A |
| I-1003 | A |
| I-1004 | A |
| I-1005 | A |
| I-1006 | A |
| I-1007 | A |
| I-1008 | A |
| I-1009 | A |
| I-1010 | A |
| I-1011 | A |
| I-1012 | A |
| I-1013 | A |
| I-1014 | B |
| I-1015 | B |
| I-1016 | B |
| I-1017 | B |
| I-1018 | B |
| I-1019 | B |
| I-1020 | B |
| I-1021 | B |
| I-1022 | B |
| I-1023 | C |
| I-1024 | C |
| I-1025 | C |
| I-1026 | C |
| II-1001 | A |
| II-1012 | A |
| II-1023 | A |
| II-1025 | A |
| II-1002 | A |
| II-1003 | B |
| II-1005 | C |
| II-1007 | C |
| II-1026 | C |
| II-1008 | D |
| II-1010 | D |
| II-1011 | D |
| II-1013 | D |
| III-1001 | A |
| III-1002 | C |
| III-1003 | A |
| III-1004 | B |
| III-1005 | B |
| III-1006 | B |
| III-1007 | D |
| III-1013 | B |
| III-1015 | A |
| III-1017 | A |
| III-1018 | A |
| III-1019 | A |
| III-1029 | A |
| III-1030 | A |
| IV-1002 | C |
| IV-1004 | A |
| V-1001 | A |
| V-1002 | A |
| V-1008 | C |

TABLE 2-continued

IC50 values for tested compounds

| No of compound | IC50 |
|---|---|
| V-1030 | B |
| V-1031 | B |
| V-1032 | A |
| V-1033 | A |
| V-1034 | A |
| V-1035 | A |
| V-1036 | A |
| V-1037 | C |
| V-1038 | A |
| V-1039 | A |
| V-1040 | A |
| V-1041 | A |
| V-1042 | A |
| V-1043 | B |
| V-1044 | A |
| V-1045 | B |
| V-1046 | B |
| V-1047 | A |
| V-1048 | A |
| V-1049 | A |
| V-1050 | A |
| V-1051 | A |
| V-1052 | A |
| V-1053 | A |
| V-1054 | A |
| V-1055 | A |
| VI-1001 | A |
| VI-1002 | B |
| VI-1003 | B |
| VI-1004 | B |
| VI-1005 | B |
| VI-1006 | B |
| VI-1007 | B |
| V-1027 | B |
| VII-1001 | A |
| VII-1005 | A |
| VII-1012 | B |
| VII-1014 | B |
| VII-1017 | A |
| VII-1020 | B |
| VII-1025 | B |
| VIII-1001 | A |
| VIII-1003 | B |
| VIII-1016 | B |
| VIII-1017 | C |
| VIII-1025 | C |
| VIII-1026 | C |

EXAMPLE 3

Synthesis of Compounds of the General Formula I, (Scheme 1)

Compounds a2. Water solution of $NaNO_2$ (1.05 mol in 150 ml of water) cooled to 0° C. was slowly added at vigorous stirring to the mixture of amine (1 mol), water (1000 ml) and HCl (230 ml). The prepared diazo solution was added drop by drop at stirring and temperature 0-5° C. to prepared beforehand solution of compound a1 (1 mol) and sodium acetate (1.5 mol) in the mixture of 100 ml of ethanol and minimal amount of water. The reaction mixture was stirred for an hour, the obtained precipitate was filtered off, washed with water and dried in the open air. Yield of compounds a2 was 50-75%. It was used in the next stage without additional purification.

Compounds a3. Solution of sodium ethylate (1 mol of sodium in 300 ml of absolute ethanol) was added to solution of β-dicarbonyl compound (1 mol) in 100 ml of ether at stirring and room temperature, after stirring for an hour compound a2 (1 mol) was added to the reaction mixture in portions. The resultant mixture was stirred for 15 hours at room temperature and evaporated at reduced pressure. The residue was crystallized from ethanol. The yield of compounds a3 was 25-35%.

Compounds a4. Hydrazine hydrate (1.1 mol) was added drop by drop at stirring to the solution of compound a3 (1 mol) in ethanol (100 ml). The reaction mixture was boiled for 24 hours, after that cooled to 0° C. The resultant precipitate was filtered off, washed with ethanol and dried in the open air. If necessary, the product was recrystallized from ethanol. The yield of compounds a4 was 35-55%.

Compounds a5. NaH (1.15 mol) was added in small portions to cooled to 0° C. solution of compound a4 (1 mol) in absolute DMF (500 ml) at vigorous stirring holding up the temperature about 0° C. After stirring for an hour the solution of halogenalkylcarboxylate (1.1 mol) in minimal amount of absolute DMF was added to the reaction mixture during an hour, after that stirring was continued for additional 5 hours. Then the reaction mixture was poured into 10-fold volume of water and ice at vigorous stirring. The resultant precipitate was filtered off, washed with water and recrystallized from ethanol. The yield of compounds a5 was 75-82%.

Compounds of the general formula I. Kalium hydroxide (0.025 mol) was added in portions to water suspension of compound a5 (0.021 mol in 100 ml of water). The mixture was boiled until complete dissolution of solid, then cooled to 0° C. and aciditied with 10% HCl solution to pH=5-6. The resultant precipitate was filtered off, washed with water and dried in the open air. If necessary, the product was recrystallized from water-ethanol mixture. The yield of acids was 80-89%. Then to the solution of acid (1 mmol) in absolute DMF (5 ml) 1,1'-carbonyldiimidazole (1.15 mmol) was added and the resultant mixture was stirred at 80° C. for an hour in nitrogen atmosphere. Primary or secondary amine (1.4 mmol) was added to the obtained mixture and stirring was continued at the same temperature for additional 6 hours. After cooling to room temperature the reaction mixture was poured into 3% solution of $Na_2CO_3$ (50 ml) and stirred until solid precipitated, the latter was filtered off, washed twice with water and dried in the open air. If necessary, the product was recrystallised from the proper solvent. Oily products were extracted with methylene chloride, organic layer was washed twice with water, dried over $MgSO_4$ and evaporated under reduced pressure. The prepared crude product was purified either by recrystallization from the proper solvent or by flash chromatography on silica gel. The yield of amides of the general formula I was 20-85%, some of them are presented in Table 3.

TABLE 3

Spectral data for compounds of the general formula I.

| No | Formula | $^1$H NMR, DMSO-d6, δ, ppm; LCMS, m/z (M + 1) |
|---|---|---|
| I-1001 | | $^1$H NMR (DMSO, 400 MHz) δ: 2.45 (s, 3H), 2.63 (s, 3H), 3.15-3.29 (m, 4H), 3.55-3.78 (m, 7H), 5.00 (s, 2H), 6.40 (d, J = 7.8 Hz, 1H), 6.50 (s, 1H), 6.56 (d, J = 7.8 Hz, 1H), 7.14 (t, J = 7.8 Hz, 1H), 7.54-7.67 (m, 5H); LCMS m/z 473 (M + 1); M.p. 218-220° C. |
| I-1002 | | $^1$H NMR (DMSO, 400 MHz) δ: 2.45 (s, 3H), 2.65 (s, 3H), 3.12-3.40 (m, 4H), 3.50-3.75 (m, 4H), 5.00 (s, 2H), 6.82 (d, J = 7.7 Hz, 1H), 6.94 (d, J = 7.7 Hz, 1H), 6.98 (s, 1H), 7.24 (t, J = 7.7 Hz, 1H), 7.64 (br s, 5H); LCMS m/z 477 (M + 1); M.p. 257-259° C. |
| I-1003 | | $^1$H NMR (DMSO, 300 MHz) δ: 2.49 (s, 3H), 2.64 (s, 3H), 3.09-3.27 (m, 4H), 3.57-3.75 (m, 4H), 4.91 (s, 2H), 6.76 (t, J = 7.5 Hz, 1H), 6.91 (t, J = 7.5 Hz, 2H), 7.28 (d, J = 7.5 Hz, 2H), 7.55 (br s, 5H); LCMS m/z 443 (M + 1); M.p. 252-254° C. |

TABLE 3-continued

Spectral data for compounds of the general formula I.

| No | Formula | $^1$H NMR, DMSO-d6, δ, ppm; LCMS, m/z (M + 1) |
|---|---|---|
| I-1004 | | $^1$H NMR (DMSO, 300 MHz) δ: 2.19 (s, 3H), 2.21 (s, 3H), 2.54 (s, 3H), 2.63 (s, 3H), 2.45-2.80 (m, 4H), 3.53-3.78 (m, 4H), 4.99 (s, 2H), 6.91 (d, J = 8.0 Hz, 2H), 7.06 (t, J = 8.0 Hz, 1H), 7.64 (br s, 5H); LCMS m/z 471 (M + 1); M.p. 249-251° C. |
| I-1005 | | $^1$H NMR (DMSO, 300 MHz) δ: 2.22 (s, 3H), 2.25 (s, 3H), 2.52 (s, 3H), 2.63 (s, 3H), 2.73-2.97 (m, 4H), 3.54-3.77 (m, 4H), 5.02 (s, 2H), 6.80 (d, J = 8.1 Hz, 1H), 6.86 (s, 1H), 7.06 (d, J = 8.1 Hz, 1H), 7.64 (br s, 5H); LCMS m/z 471 (M + 1); M.p. 232-234° C. |
| I-1006 | | $^1$H NMR (DMSO, 300 MHz) δ: 2.51 (s, 3H), 2.63 (s, 3H), 3.00-3.23 (m, 4H), 3.52-3.77 (m, 4H), 5.02 (s, 2H), 6.95-7.13 (m, 4H), 7.63 (br s, 5H); LCMS m/z 461 (M + 1); M.p. 257-259° C. |

TABLE 3-continued
Spectral data for compounds of the general formula I.
| No | Formula | $^1$H NMR, DMSO-d6, δ, ppm; LCMS, m/z (M + 1) |
|---|---|---|
| I-1007 | 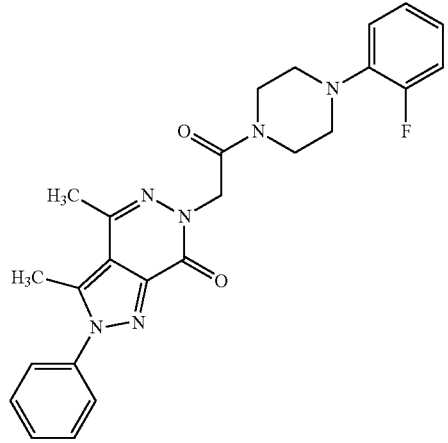 [SMILES: Cc1nn(CC(=O)N2CCN(c3ccccc3F)CC2)c(=O)c2nn(-c3ccccc3)c(C)c12] | $^1$H NMR (DMSO, 300 MHz) δ: 2.51 (s, 3H), 2.62 (s, 3H), 2.93-3.14 (m, 4H), 3.55-3.78 (m, 4H), 5.02 (s, 2H), 6.96-7.20 (m, 4H), 7.63 (br s, 5H); LCMS m/z 461 (M + 1); M.p. 240-242° C. |
| I-1008 | 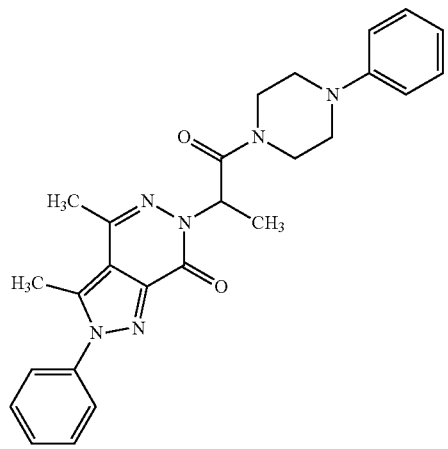 [SMILES: Cc1nn(C(C)C(=O)N2CCN(c3ccccc3)CC2)c(=O)c2nn(-c3ccccc3)c(C)c12] | $^1$H NMR (DMSO, 300 MHz) δ: 1.42 (d, J = 6.5 Hz, 3H), 2.51 (s, 3H), 2.61 (s, 3H), 2.82-3.75 (m, 8H), 5.83 (qv, J = 6.5 Hz, 1H), 6.78 (d, J = 7.8 Hz, 2H), 6.90 (t, J = 7.8 Hz, 1H), 7.18 (d, J = 7.8 Hz, 2H), 7.55-7.71 (m, 5H); LCMS m/z 457 (M + 1); M.p. 193-195° C. |
| I-1009 | 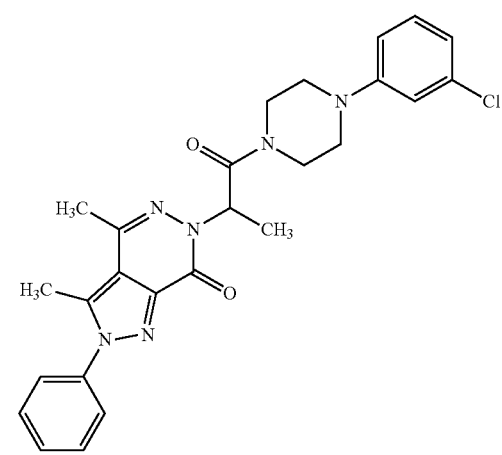 [SMILES: Cc1nn(C(C)C(=O)N2CCN(c3cccc(Cl)c3)CC2)c(=O)c2nn(-c3ccccc3)c(C)c12] | $^1$H NMR (DMSO, 300 MHz) δ: 1.44 (d, J = 6.4 Hz, 3H), 2.49 (s, 3H), 2.62 (s, 3H), 2.86-3.77 (m, 8H), 5.82 (qv, J = 6.4 Hz, 1H), 6.72-6.96 (m, 3H), 7.20 (d, J = 7.9 Hz, 1H), 7.55-7.71 (m, 5H); LCMS m/z 491 (M + 1); M.p. 194-196° C. |

TABLE 3-continued

Spectral data for compounds of the general formula I.

| No | Formula | $^1$H NMR, DMSO-d6, δ, ppm; LCMS, m/z (M + 1) |
|---|---|---|
| I-1010 | | $^1$H NMR (DMSO, 300 MHz) δ: 0.90-1.59 (m, 6H), 1.44 (d, J = 6.4 Hz, 3H), 1.53-1.85 (m, 5H), 2.10-2.52 (m, 4H), 2.56 (s, 3H), 2.68 (s, 3H), 3.16 (br s, 1H), 3.25-3.90 (m, 2H), 3.64 (br s, 1H), 5.19 (q, J = 6.4 Hz, 1H), 7.49-7.64 (m, 5H); LCMS m/z 463 (M + 1); M.p. 132-135° C. |
| I-1011 | | $^1$H NMR (DMSO, 400 MHz) δ: 1.47 (d, J = 6.5 Hz, 3H), 2.17 (s, 3H), 2.23 (s, 3H), 2.50-2.90 (m, 10H), 3.30-3.95 (m, 4H), 5.79 (qv, J = 6.5 Hz, 1H), 6.70-6.82 (m, 2H), 6.96 (t, J = 7.9 Hz, 1H), 7.58 (br s, 5H); LCMS m/z 485 (M + 1); M.p. 136-138° C. |
| I-1012 | | $^1$H NMR (DMSO, 300 MHz) δ: 1.39 (d, J = 6.5 Hz, 3H), 1.98-2.38 (m, 4H), 2.49 (s, 3H), 2.64 (s, 3H), 3.15-3.56 (m, 6H), 5.74 (qv, J = 6.5 Hz, 1H), 7.18-7.36 (m, 5H), 7.63 (br s, 5H); LCMS m/z 471 (M + 1); M.p. 152-154° C. |

TABLE 3-continued

Spectral data for compounds of the general formula I.

| No | Formula | $^1$H NMR, DMSO-d6, δ, ppm; LCMS, m/z (M + 1) |
|---|---|---|
| I-1013 | | $^1$H NMR (DMSO, 300 MHz) δ: 1.44 (d, J = 6.5 Hz, 3H), 2.53 (s, 3H), 2.63 (s, 3H), 2.70-3.06 (m, 4H), 3.38-3.80 (m, 4H), 5.82 (qv, J = 6.5 Hz, 1H), 6.90-7.19 (m, 4H), 7.63 (br s, 5H); LCMS m/z 463 (M + 1) |
| I-1014 | | $^1$H NMR (DMSO, 300 MHz) δ: 2.00 (s, 3H), 2.44 (s, 3H), 2.46 (s, 3H), 2.57 (s, 3H), 5.93 (s, 2H), 6.96-7.14 (m, 3H), 7.15-7.31 (m, 3H), 8.14 (t, J = 7.2Hz, 1H), 9.80 (br s, 1H) |
| I-1015 | | $^1$H NMR (DMSO, 300 MHz) δ: 0.81 (t, J = 6.9 Hz, 3H), 1.07 (t, J = 6.2 Hz, 1H), 1.95 (qv, J = 6.9 Hz, 2H), 2.39-2.55 (m, 4H), 2.61 (s, 3H), 3.16-3.65 (m, 6H), 5.61 (t, J = 6.0 Hz, 1H), 7.63 (br s, 5H) |
| I-1016 | | $^1$H NMR (DMSO, 300 MHz) δ: 2.22 (s, 3H), 2.43 (s, 3H), 2.51 (s, 3H), 2.60 (s, 3H), 4.21 (d, J = 3.8 Hz, 2H), 4.66 (s, 2H), 5.97 (d, J = 2.1 Hz, 1H), 6.12 (d, J = 2.8 Hz, 1H), 7.38-7.53 (m, 4H), 8.44 (br s, J = 3.8Hz, 1H) |
| I-1017 | | $^1$H NMR (DMSO, 300 MHz) δ: 1.49 (d, J = 6.8 Hz, 3H), 2.44 (s, 3H), 2.61 (s, 3H), 2.90 (t, J = 6.6 Hz, 2H), 3.18-3.38 (m, 2H), 5.44 (qv, J = 6.8 Hz, 1H), 6.84-6.96 (m, 2H), 7.31 (d, J = 5.6 Hz, 1H), 7.41-7.53 (m, 4H), 7.82 (br s, J = 3.7 Hz, 1H) |

TABLE 3-continued

Spectral data for compounds of the general formula I.

| No | Formula | $^1$H NMR, DMSO-d6, δ, ppm; LCMS, m/z (M + 1) |
|---|---|---|
| I-1018 | | $^1$H NMR (DMSO, 300 MHz) δ: 0.37-0.43 (m, 2H), 0.51-0.61 (m, 2H), 0.70-0.80 (m, 3H), 1.88-2.16 (m, 2H), 2.43 (s, 3H), 2.50 (s, 3H), 2.55-2.68 (m, 4H), 5.16-5.25 (m, 1H), 7.39-7.52 (m, 4H), 7.72 (br s, 1H) |
| I-1019 | | $^1$H NMR (DMSO, 300 MHz) δ: 2.49 (s, 3H), 2.56-2.68 (s, 4H), 3.23-3.22 (m, 1H), 4.24-4.36 (m, 4H), 7.26-7.36 (m, 1H), 7.56-7.72 (m, 6H), 8.42-8.55 (m, 3H) |
| I-1020 | | $^1$H NMR (DMSO, 300 MHz) δ: 2.41-2.65 (m, 8H), 4.16-4.34 (m, 4H), 6.19 (d, J = 5.5 Hz, 1H), 6.34-6.38 (m 1H), 7.50-7.72 (m, 6H), 8.38 (br s, J = 4.6 Hz, 1H) |
| I-1021 | | $^1$H NMR (DMSO, 300 MHz) δ: 2.51 (s, 3H), 2.60 (s, 3H), 2.76 (t, J = 8.9 Hz, 2H), 3.18-3.38 (m, 2H), 3.38-3.48 (m, 2H), 3.50-3.60 (m, 2H), 4.25 (t, J = 8.9 Hz, 2H), 7.54-7.68 (m, 5H) |
| I-1022 | | $^1$H NMR (DMSO, 300 MHz) δ: 2.52 (s, 3H), 2.61 (t, J = 7.0 Hz, 2H), 2.66 (s, 3H), 4.23-4.36 (m, 2H), 4.40-4.51 (m, 2H), 6.88 (t, J = 5.5 Hz, 1H), 6.92 (br s, 1H), 7.16 (d, J = 6.1 Hz, 1H), 7.48-7.62 (m, 5H), 8.25 (br s, 1H) |

TABLE 3-continued

Spectral data for compounds of the general formula I.

| No | Formula | $^1$H NMR, DMSO-d6, δ, ppm; LCMS, m/z (M + 1) |
|---|---|---|
| I-1023 | | $^1$H NMR (DMSO, 300 MHz) δ: 1.91 (q, J = 7.0 Hz, 2H), 2.08 (t, J = 7.0 Hz, 2H), 2.42 (s, 3H), 2.50 (s, 3H), 2.67 (s, 3H), 2.72 (t, J = 7.0 Hz, 2H), 3.25 (t, J = 7.0 Hz, 2H), 4.03 (t, J = 7.0 Hz, 2H), 6.09-6.15 (m, 1H), 6.30-6.37 (m, 1H), 7.39-7.52 (m, 5H), 7.91 (br s, 1H) |
| I-1024 | | $^1$H NMR (DMSO, 300 MHz) δ: 0.99 (t, J = 6.8 Hz, 3H), 1.94 (q, J = 6.8 Hz, 2H), 2.20-2.39 (m, 8H), 2.44 (s, 3H), 2.50 (s, 3H), 2.61 (s, 3H), 3.35-3.48 (m, 4H), 4.08 (t, J = 6.8 Hz, 2H), 7.42 (d, J = 8.0 Hz, 2H), 7.48 (d, J = 8.0 Hz, 2H); LCMC m/z 437 (M + 1) |
| I-1025 | | $^1$H NMR (DMSO, 300 MHz) δ: 2.02 (q, J = 7.1 Hz, 2H), 2.31 (t, J = 7.1 Hz, 2H), 2.54 (s, 3H), 2.66 (s, 3H), 3.37-3.68 (m, 8H), 4.10 (t, J = 7.1 Hz, 2H), 7.46-7.63 (m, 5H) |
| I-1026 | | $^1$H NMR (DMSO, 300 MHz) δ: 1.13 (d, J = 6.6 Hz, 6H), 2.02 (qv, J = 7.0 Hz, 2H), 2.33 (t, J = 7.0 Hz, 2H), 2.48 (s 3H), 2.57 (s, 3H), 2.80 (s, J = 6.6 Hz, 1H), 4.09 (t, J = 7.0 Hz, 2H), 7.12 (d, J = 8.5 Hz, 2H), 7.44 (d, J = 8.5 Hz, 2H), 7.55-7.68 (m, 5H), 9.76 (br s, 1H) |

TABLE 3-continued

Spectral data for compounds of the general formula I.

| No | Formula | ¹H NMR, DMSO-d6, δ, ppm; LCMS, m/z (M + 1) |
|---|---|---|
| I-1027 | | LCMS m/z 500 (M + 1) |
| I-1028 | | LCMS m/z 458 (M + 1) |
| I-1029 | | LCMS m/z 475 (M + 1) |
| I-1030 | | LCMS m/z 487 (M + 1) |

EXAMPLE 4

Synthesis of Compounds of the General Formula II, (Scheme 2)

Compounds b1. POCl$_3$ (1.1 mol) was added drop by drop to suspension of N-substituted pyrazin-3-one (1 mol) in pyridine (1.15 mol), holding the temperature below 50° C. The reaction mixture was boiled for 5 hours, poured into 10-fold volume of water and ice and extracted three times with chloroform. The combined organic layers were washed with 3% soda solution, water and dried over MgSO$_4$ and evaporated under reduced pressure. The obtained oil was distilled in vacuum. The yield of chromatographically pure chloro-derivative was 60-80%. Then nitric acid (5 eq., d=1.51) was added drop by drop to the solution of chloro-derivative in acetic anhydride (3 eq.) at stirring and temperature 0° C. The reaction mixture was stirred for an hour at 0° C., then for 4 hours at room temperature and poured into 10-fold volume of water and ice. The solid precipitated was filtered off, washed with water and dried in the open air. The yield of chloro-nitro-derivative b1 was 70-80%.

Compounds b2. Dried K$_2$CO$_3$ (0.12 mol) was added to the solution of compound b1 (0.1 mol) in absolute acetone (350 ml), then at stirring thioglycolic ester (0.11 mol) was added drop by drop. The reaction mixture was boiled for 5 hours, then K$_2$CO$_3$ was filtered off, the solvent was evaporated under reduced pressure. The obtained product was recrystallized from ethanol. The yield of compounds b2 was 65-82%.

Compounds b3. Triethylamine (1 mol) and sodium dithionite (1.5 mol). were added to the solution of compound b2 (0.3 mol) in ethanol (1500 ml). The reaction mixture was boiled at stirring for 12 hours, cooled to room temperature and filtered. Filtrate was evaporated under reduced pressure, the oily residue was dissolved in methylene chloride (500 ml), washed with 5% solution of HCl three times, with water and dried over MgSO$_4$. The solvent was evaporated under reduced pressure, the residue was recrystallized from ethanol. The yield of compounds b3 was 35-45%.

Compounds b4. Dried K$_2$CO$_3$ (0.15 mol) and the corresponding haloalkylcarboxylate (0.11 mol) were added to the solution of compound b3 (0.1 mol) in abs. DMF (150 ml). The reaction mixture was stirred for 5 hours at 50° C., after that it was poured into 10-fold volume of water. The solid precipitated was filtered off, washed with water, dried in the open air and recrystallized from ethanol. The yield of compounds b4 was 68-83%.

Compounds of the general formula II. KOH (0.025 mol) was added to water suspension of compound b4 (0.021 mol in 100 ml of water). The reaction mixture was boiled at stirring until complete dissolution of compound b4, then cooled and acidified with 10% solution of HCl to pH=5-6. The precipitate obtained was filtered off, washed with water and dried in the open air. The yield of the corresponding acids was 80-92%. Then, 1,1'-carbonyldiimidazole (1.15 mmol) was added to the solution of acid (1 mmol) in absolute DMFA (5 ml) and the mixture was stirred at 80° C. for 1 hour in nitrogen atmosphere. Then primary or secondary amine (1.4 mmol) was added and the mixture was stirred at the same temperature for additional 6 hours. After cooling to room temperature the reaction mixture was poured into 3% solution of soda (50 ml) and stirred until solid precipitated. The latter was filtered off, washed twice with water and dried in the open air. If required, the product was recrystallized from the proper solvent. The oily products were extracted with methylene chloride, organic layer was washed twice with water, dried over MgSO$_4$ and evaporated under reduced pressure. The prepared crude product was purified either by recrystallization from the proper solvent or by flash chromatography on silica gel. The yield of amides of the general formula II was 20-85%, some of them are presented in Table 4.

TABLE 4

Spectral data for compounds of the general formula II.

| No | Formula | $^1$H NMR DMSO-d6, δ, ppm; LCMS, m/z (M + 1) |
|---|---|---|
| II-1001 | 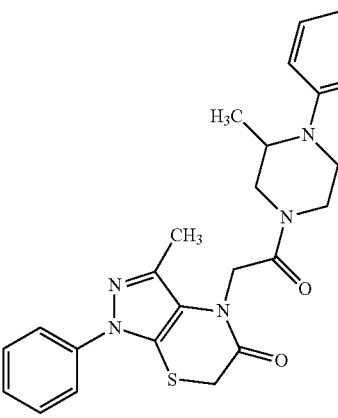 | $^1$H NMR (DMSO, 300 MHz) δ: 0.80-1.11 (m, 3H), 2.26 (s, 3H), 2.88-3.45 (m, 4H), 3.50-3.87 (m, 3H), 3.90-4.12 (m, 2H), 4.61-4.85 (m, 2H), 6.61 (d, J = 7.2 Hz, 1H), 6.68-6.80 (m, 2H), 7.11 (d, J = 7.2 Hz, 1H), 7.34-7.48 (m, 3H), 7.49-7.60 (m, 2H); LCMS m/z 476 (M + 1) |
| II-1002 | 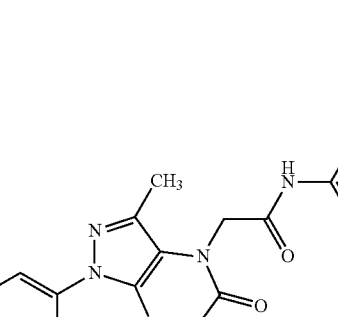 | $^1$H NMR (DMSO, 300 MHz) δ: 2.35 (s, 3H), 3.55 (s, 2H), 4.56 (s, 2H), 7.28-7.33 (m, 2H), 7.37-7.51 (m, 5H), 7.88 (d, J = 7.8 Hz, 1H), 7.96 (s, 1H), 10.22 (br s, 1H) |

TABLE 4-continued

Spectral data for compounds of the general formula II.

| No | Formula | ¹H NMR DMSO-d6, δ, ppm; LCMS, m/z (M + 1) |
|---|---|---|
| II-1003 | | ¹H NMR (DMSO, 300 MHz) δ: 2.25 (s, 3H), 3.69 (s, 2H), 4.41 (d, J = 5.7 Hz, 2H), 4.52 (s, 2H), 7.16-7.33 (m, 2H), 7.35-7.44 (m, 3H), 7.48-7.69 (m, 2H), 7.75 (t, J = 8.26 Hz, 1H), 8.49 (d, J = 7.6 Hz, 1H), 8.71 (br s, J = 5.7 Hz, 1H) |
| II-1004 | | ¹H NMR (DMSO, 300 MHz) δ: 1.30-1.42 (m, 2H), 1.43-1.56 (m, 2H), 1.57-1.70 (m, 2H), 1.72-1.88 (m, 2H), 2.27 (s, 3H), 3.65 (s, 2H), 3.95-4.10 (m, 1H), 4.37 (s 2H), 7.35-7.48 (m, 3H), 7.54 (t, J = 8.0 Hz, 2H), 7.98 (br s, J = 5.9 Hz, 1H) |
| II-1005 | | ¹H NMR (DMSO, 300 MHz) δ: 2.40 (s, 3H), 2.66 (d, J = 6.0 Hz, 2H), 3.55 (d, J = 6.0 Hz, 2H), 3.65 (s, 2H), 3.71 (s, 3H), 3.74 (s, 3H), 4.36 (s, 2H), 6.71 (d, J = 8.5 Hz, 1H), 6.78-6.89 (m, 2H), 7.34-7.48 (m, 3H), 7.49-7.57 (m, 2H), 8.22 (br s, 1H) |
| II-1006 | | ¹H NMR (DMSO, 300 MHz) δ: 2.25 (s, 3H), 3.68 (s, 2H), 4.32 (d, J = 5.3 Hz, 2H), 4.52 (s, 2H), 6.27 (d, J = 2.8 Hz, 1H), 6.38 (s, 1H), 7.38-7.48 (m, 3H), 7.50-7.60 (m, 3H), 8.56 (br s, J = 5.3 Hz, 1H) |
| II-1007 | | ¹H NMR (DMSO, 300 MHz) δ: 2.23 (s, 3H), 3.68 (s, 2H), 3.74 (s, 3H), 4.26 (d, J = 5.8 Hz, 2H), 4.44 (s, 2H), 6.88 (d, J = 8.7 Hz, 2H), 7.19 (d, J = 8.7 Hz, 2H), 7.37-7.48 (m, 3H), 7.50-7.60 (m, 2H), 8.62 (br s, J = 5.8 Hz, 1H) |

TABLE 4-continued

Spectral data for compounds of the general formula II.

| No | Formula | $^1$H NMR DMSO-d6, δ, ppm; LCMS, m/z (M + 1) |
|---|---|---|
| II-1008 | | $^1$H NMR (DMSO, 300 MHz) δ: 1.06 (d, J = 6.5 Hz, 6H), 2.29 (s, 3H), 3.62 (s, 2H), 3.88 (s, J = 6.5 Hz, 1H), 4.35 (s, 2H), 7.34-7.47 (m, 3H), 7.48-7.59 (m, 2H), 7.85 (br d, J = 5.0 Hz, 1H) |
| II-1009 | | $^1$H NMR (DMSO, 300 MHz) δ: 2.23 (s, 3H), 3.68 (s, 2H), 4.43 (s, 2H), 4.50 (d, J = 5.0 Hz, 2H), 6.92-7.02 (m, 2H), 7.34-7.49 (m, 4H), 7.50-7.61 (m, 2H), 8.66 (br s, 1H) |
| II-1010 | | $^1$H NMR (DMSO, 300 MHz) δ: 2.20-2.45 (m, 7H), 3.21 (br s, 4H), 3.55 (br s, 4H), 3.65 (s, 2H), 4.38 (s, 2H), 7.35-7.47 (m, 3H), 7.49-7.62 (m, 2H), 7.93 (br s, 1H) |
| II-1011 | | $^1$H NMR (DMSO, 300 MHz) δ: 2.26 (s, 3H), 2.62 (s, 3H), 3.63 (s, 2H), 4.37 (s, 2H), 7.34-7.48 (m, 3H), 7.50-7.62 (m, 2H), 7.94 (br s, 1H) |
| II-1012 | | $^1$H NMR (DMSO, 300 MHz) δ: 2.27 (s, 3H), 3.23 (br s, 4H), 3.50-3.80 (m, 6H), 4.75 (s, 2H), 6.98 (d, J = 8.6 Hz, 2H), 7.26 (d, J = 8.6 Hz, 2H), 7.34-7.48 (m, 3H), 7.49-7.62 (m, 2H) |
| II-1013 | | $^1$H NMR (DMSO, 300 MHz) δ: 1.71-1.88 (m, 2H), 1.89-2.04 (m, 2H), 2.28 (s, 3H), 3.30-3.42 (m, 2H), 3.47-3.60 (m, 2H), 3.64 (s, 2H), 4.54 (s, 2H), 7.34-7.48 (m, 3H), 7.49-7.60 (m, 2H) |

TABLE 4-continued

Spectral data for compounds of the general formula II.

| No | Formula | ¹H NMR DMSO-d6, δ, ppm; LCMS, m/z (M + 1) |
|---|---|---|
| II-1014 | | ¹H NMR (DMSO, 300 MHz) δ: 2.26 (s, 3H), 3.41-3.75 (m, 10 2H), 4.70 (s, 2H), 7.34-7.49 (m, 3H), 7.50-7.61 (m, 2H) |
| II-1015 | | ¹H NMR (DMSO, 300 MHz) δ: 2.22 (s, 3H), 2.24 (s, 3H), 3.65 (s, 2H), 4.23 (d, J = 4.0 Hz, 2H), 4.41 (s, 2H), 5.97 (br s, 1H), 6.10 (br s, 1H), 7.23-7.60 (m, 5H), 8.44 (br s, 1H) |
| II-1016 | | ¹H NMR (DMSO, 300 MHz) δ: 1.75 (q, J = 7.6 Hz, 2H), 2.21 (t, J = 7.6 Hz, 2H), 2.35 (s, 3H), 3.68 (s, 2H), 3.71 (t, J = 7.6 Hz, 2H), 4.26 (d, J = 5.8 Hz, 2H), 7.15-7.60 (m, 9H), 8.38 (br s, J = 5.8 Hz, 1H) |
| II-1017 | | ¹H NMR (DMSO, 300 MHz) δ: 1.77 (q, J = 7.5 Hz, 2H), 2.23 (t, J = 7.5 Hz, 2H), 2.36 (s, 3H), 3.59 (s, 2H), 3.87 (t, J = 7.5 Hz, 2H), 4.35 (d, J = 5.9 Hz, 2H), 7.18-7.30 (m, 2H), 7.34-7.48 (m, 3H), 7.49-7.60 (m, 3H), 7.73 (t, J = 8.7 Hz, 1H), 8.39-8.52 (m, 2H) |

TABLE 4-continued

Spectral data for compounds of the general formula II.

| No | Formula | $^1$H NMR DMSO-d6, δ, ppm; LCMS, m/z (M + 1) |
|---|---|---|
| II-1018 | | $^1$H NMR (DMSO, 300 MHz) δ: 1.81 (q, J = 7.6 Hz, 2H), 2.30-2.44 (m, 5H), 3.61 (s, 2H), 3.72 (s, 3H), 3.92 (t, J = 6.6 Hz, 2H), 6.59 (d, J = 8.6 Hz, 1H), 7.06-7.21 (m, 2H), 7.26 (br s, 1H), 7.35-7.48 (m, 3H), 7.50-7.59 (m, 3H), 9.89 (br s, 1H) |
| II-1019 | | $^1$H NMR (DMSO, 300 MHz) δ: 1.72 (q, J = 7.4 Hz, 2H), 2.18 (t, J = 7.4 Hz, 2H), 2.38 (s, 3H), 3.59 (s, 2H), 3.82 (t, J = 7.4 Hz, 2H), 4.24 (d, J = 5.8 Hz, 2H), 6.21 (d, J = 4.0 Hz, 1H), 6.33-6.38 (m, 1H), 7.33-7.58 (m, 6H), 8.30 (br t, J = 5.8 Hz, 1H) |
| II-1020 | | $^1$H NMR (DMSO, 300 MHz) δ: 1.69 (q, J = 7.4 Hz, 2H), 2.13 (t, J = 7.4 Hz, 2H), 2.38 (s, 3H), 3.11-3.25 (m, 5H), 3.27-3.33 (m, 2H), 3.59 (s, 2H), 3.82 (t, J = 7.4 Hz, 2H), 4.24 (d, J = 5.8 Hz, 2H), 7.34-7.59 (m, 5H), 7.90 (br s, J = 5.9 Hz, 1H) |
| II-1021 | | $^1$H NMR (DMSO, 300 MHz) δ: 1.70 (q, J = 7.6 Hz, 2H), 2.10 (t, J = 7.6 Hz, 2H), 2.37 (s, 3H), 2.54 (d, J = 4.0 Hz, 3H), 3.57 (s, 2H), 3.84 (t, J = 7.6 Hz, 2H), 7.34-7.58 (m, 5H), 7.90 (br s, J = 4.0 Hz, 1H) |

TABLE 4-continued

Spectral data for compounds of the general formula II.

| No | Formula | $^1$H NMR DMSO-d6, δ, ppm; LCMS, m/z (M + 1) |
|---|---|---|
| II-1022 | | $^1$H NMR (DMSO, 300 MHz) δ: 1.40 (br s, 4H), 1.53 (br s, 4H), 1.75 (q, J = 7.4 Hz, 2H), 2.29 (t, J = 7.4 Hz, 2H), 2.37 (s, 3H), 3.31 (br s, 4H), 3.58 (s, 2H), 3.89 (t, J = 7.4 Hz, 2H), 4.24 (d, J = 5.8 Hz, 2H), 7.34-7.47 (m, 3H), 7.48-7.59 (m, 2H) |
| II-1023 | | $^1$H NMR (DMSO, 300 MHz) δ: 1.77 (q, J = 7.5 Hz, 2H), 2.29 (t, J = 7.5 Hz, 2H), 2.80-2.96 (m, 5H), 3.05 (br s, 4H), 3.44-3.65 (m, 6H), 3.90 (t, J = 7.5 Hz, 2H), 6.78 (t, J = 8.4 Hz, 1H), 6.87 (d, J = 8.4 Hz, 2H), 7.19 (d, J = 8.4 Hz, 2H), 7.34-7.57 (m, 5H) |
| II-1024 | | $^1$H NMR (DMSO, 300 MHz) δ: 1.75 (q, J = 7.4 Hz, 2H), 2.36 (t, J = 7.4 Hz, 2H), 2.40 (s, 3H), 3.25-3.86 (m, 4H), 3.48 (br s, 4H), 3.58 (s, 2H), 3.87 (t, J = 7.4 Hz, 2H), 4.24 (d, J = 5.8 Hz, 2H), 7.34-7.48 (m, 3H), 7.50-7.61 (m, 2H) |
| II-1025 | | $^1$H NMR (DMSO, 300 MHz) δ: 1.77 (q, J = 7.5 Hz, 2H), 2.30-2.38 (m, 5H), 3.37-3.56 (m, 8H), 3.60 (s, 2H), 3.89 (t, J = 7.5 Hz, 2H), 6.54-6.62 (m, 2H), 7.32-7.58 (m, 6H), 7.19 (d, J = 5.7 Hz, 1H) |

TABLE 4-continued

Spectral data for compounds of the general formula II.

| No | Formula | $^1$H NMR DMSO-d6, δ, ppm; LCMS, m/z (M + 1) |
|---|---|---|
| II-1026 | | $^1$H NMR (DMSO, 300 MHz) δ: 1.82 (q, J = 7.6 Hz, 2H), 2.33-2.44 m, 5H), 3.58 (s, 2H), 3.69 (s, 3H), 3.96 (t, J = 7.6 Hz, 2H), 6.85 (d, J = 9.8 Hz, 2H), 7.34-7.58 (m, 7H), 9.77 (br s, 1H) |

EXAMPLE 5

Synthesis of Compounds of the General Formula III, (Scheme 3)

Compounds c3. The mixture of aminopyridine c1 (0.04 mol) and nitrobromoacetophenone c2 (0.04 mol) in ethanol (80 ml) was boiled for 3 hours, after that it was cooled to room temperature. The solid precipitated was filtered off, washed and dried in the opened air. Pure, yellow, crystalline product c3 was prepared with 66-75% yield.

Compounds c4. Mixture of compound 3 (0.05 mol), $SnCl_2$ (0.18 mol), water (60 ml) and hydrochloric acid (80 ml) was stirred at 60° C. for 1 hour, then cooled to room temperature and poured into water (500 ml). The resultant mixture was basified with 10% solution of soda to pH 9-10. The solid precipitated was filtered off, washed with water, dried in the opened air and recrystallized from ethanol, it gave pure compound c4 as white crystals. The yield of compounds c4 was 75-88%.

Compounds of the general formula III. Carboxylic acid (1.1 mmol) was added to the solution of 1,1'-carbonyldiimidazole (1.2 mmol) in absolute DMF (5 ml). The reaction mixture was stirred at 80° C. for 1 hour without air access. Then primary or secondary amine (1 mmol) was added and the resultant mixture was stirred at 100° C. for additional 3-4 hours and left for a night at room temperature. After that the reaction mixture was poured into 10-fold volume of water, the solid precipitated was filtered off, washed with water and dried in the opened air. Pure compounds of the general formula III were prepared by recrystallization from isopropanol, yield 30-75%, some of them are presented in Table 5.

TABLE 5

Spectral data for compounds of the general formula III.

| No | Formula | $^1$H NMR DMSO-d6, δ, ppm; LCMS, m/z (M + 1) |
|---|---|---|
| III-1001 | | $^1$H NMR (DMSO, 400 MHz) δ: 3.88 (s, 3H), 6.76 (t, J = 6.8 Hz, 2H), 7.02 (dd, J = 8.7 Hz, J = 3.1 Hz, 1H), 7.12-7.16 (m, 1H), 7.34 (t, J = 7.4 Hz, 1H), 7.48-7.57 (m, 3H), 7.77-7.85 (m, 4H), 8.12 (s, 1H), 8.38 (d, J = 7.0 Hz, 1H), 10.03 (s, 1H) |
| III-1002 | | $^1$H NMR (DMSO, 400 MHz) δ: 1.15 (t, J = 7.8 Hz, 3H), 2.33 (q, J = 7.8 Hz, 2H), 6.72 (t, J = 6.3 Hz, 1H), 7.11 (t, J = 6.8 Hz, 1H), 7.48 (d, J = 6.3 Hz, 1H), 7.69 (d, J = 8.3 Hz, 2H), 7.82 (d, J = 8.3 Hz, 2H), 8.07 (s, 1H), 8.35 (d, J = 5.7 Hz, 1H), 9.61 (br s, 1H) |
| III-1003 | | $^1$H NMR (DMSO, 400 MHz) δ: 6.77 (t, J = 6.3 Hz, 1H), 7.14 (t, J = 6.8 Hz, 1H), 7.44 (d, J = 6.8 Hz, 1H), 7.80-7.94 (m, 6H), 8.18 (s, 1H), 8.41 (d, J = 6.8 Hz, 1H), 8.71 (d, J = 6.3 Hz, 2H), 10.34 (s, 1H) |

TABLE 5-continued

Spectral data for compounds of the general formula III.

| No | Formula | $^1$H NMR DMSO-d6, δ, ppm; LCMS, m/z (M + 1) |
|---|---|---|
| III-1004 | | $^1$H NMR (DMSO, 400 MHz) δ: 7.11 (t, J = 7.1 Hz, 1H), 7.15 (br s, 1H), 7.40-7.52 (m, 1H), 7.64-7.75 (m, 2H), 7.80-7.98 (m, 4H), 8.05 (s, 1H), 8.43 (s, 1H), 8.64 (d, J = 5.9 Hz, 1H), 10.29 (br s, 1H) |
| III-1005 | | $^1$H NMR (DMSO, 400 MHz) δ: 6.75 (t, J = 6.8 Hz, 1H), 7.09-7.16 (m, 1H), 7.44-7.51 (m, 3H), 7.83 (d, J = 8.3 Hz, 2H), 7.88 (d, J = 8.3 Hz, 2H), 8.02 (d, J = 8.1 Hz, 2H), 8.16 (s, 1H), 8.41 (d, J = 6.5 Hz, 1H), 10.12 (br s, 1H) |
| III-1006 | | $^1$H NMR (DMSO, 400 MHz) δ: 3.84 (s, 3H), 6.76 (t, J = 6.9 Hz, 1H), 6.96 (d, J = 8.8 Hz, 2H), 7.09-7.16 (m, 1H), 7.48 (d, J = 8.8 Hz, 1H), 7.84 (d, J = 8.4 Hz, 2H), 7.87 (d, J = 8.4 Hz, 2H), 7.98 (d, J = 8.8 Hz, 2H), 8.13 (s, 1H), 8.40 (d, J = 6.5 Hz, 1H), 9.92 (br s, 1H) |
| III-1007 | | $^1$H NMR (DMSO, 400 MHz) δ: 2.08 (s, 3H), 7.42 (t, J = 6.5 Hz, 1H), 7.78 (J = 8.6 Hz, 4H), 7.86-8.00 (m, 2H), 8.72 (s, 1H), 8.91 (d, J = 6.5 Hz, 1H), 10.11 (br s, 1H) |
| III-1008 | | $^1$H NMR (DMSO, 400 MHz) δ: 2.04 (s, 3H), 2.59 (s, 3H), 6.63 (t, J = 6.8 Hz, 1H), 6.87 (d, J = 6.8 Hz, 1H), 7.60 (d, J = 8.1 Hz, 2H), 7.84 (d, J = 8.1 Hz, 2H), 8.03 (s, 1H), 8.19 (d, J = 6.4 Hz, 1H), 9.69 (s, 1H) |
| III-1009 | | $^1$H NMR (DMSO, 400 MHz) δ: 1.18 (t, J = 7.3 Hz, 3H), 2.30 (q, J = 7.3 Hz, 2H), 2.59 (s, 3H), 6.62 (t, J = 6.8 Hz, 1H), 6.88 (d, J = 6.8 Hz, 1H), 7.62 (d, J = 8.0 Hz, 2H), 7.85 (d, J = 8.0 Hz, 2H), 8.01 (s, 1H), 8.17 (d, J = 6.4 Hz, 1H), 9.52 (s, 1H) |
| III-1010 | | $^1$H NMR (DMSO, 400 MHz) δ: 1.15 (d, J = 6.8 Hz, 6H), 2.50-2.65 (m, 4H), 6.61 (t, J = 6.8 Hz, 1H), 6.88 (d, J = 6.8 Hz, 1H), 7.62 (d, J = 8.0 Hz, 2H), 7.83 (d, J = 8.0 Hz, 2H), 8.00 (s, 1H), 8.17 (d, J = 6.4 Hz, 1H), 9.52 (s, 1H) |

TABLE 5-continued

Spectral data for compounds of the general formula III.

| No | Formula | ¹H NMR DMSO-d6, δ, ppm; LCMS, m/z (M + 1) |
|---|---|---|
| III-1011 | 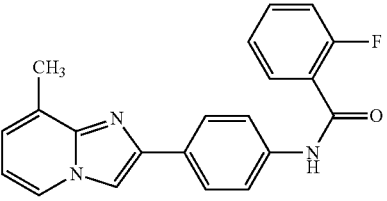 [SMILES: Cc1cccn2cc(-c3ccc(NC(=O)c4ccccc4F)cc3)nc12] | ¹H NMR (DMSO, 400 MHz) δ: 2.59 (s, 3H), 6.63 (t, J = 6.8 Hz, 1H), 6.88 (d, J = 6.8 Hz, 1H), 7.20 (t, J = 9.0 Hz, 1H), 7.26 (t, J = 7.6 Hz, 1H), 7.46-7.53 (m, 1H), 7.72-7.84 (m, 3H), 7.93 (d, J = 8.3 Hz, 2H), 8.08 (s, 1H), 8.20 (d, J = 6.3 Hz, 1H), 9.96 (s, 1H) |
| III-1012 | 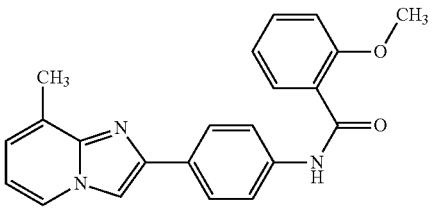 [SMILES: COc1ccccc1C(=O)Nc1ccc(-c2cn3cccc(C)c3n2)cc1] | ¹H NMR (DMSO, 400 MHz) δ: 2.61 (s, 3H), 4.02 (s, 3H), 6.63 (t, J = 6.8 Hz, 1H), 6.90 (d, J = 6.8 Hz, 1H), 7.06-7.13 (m, 2H), 7.45 (t, J = 7.7 Hz, 1H), 7.77 (d, J = 8.3 Hz, 2H), 7.90-7.97 (m, 3H), 8.09 (s, 1H), 8.21 (d, J = 6.4 Hz, 1H), 9.93 (s, 1H) |
| III-1013 | 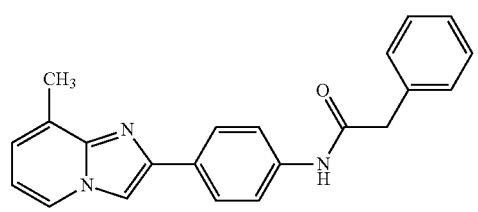 [SMILES: Cc1cccn2cc(-c3ccc(NC(=O)Cc4ccccc4)cc3)nc12] | ¹H NMR (DMSO, 400 MHz) δ: 2.60 (s, 3H), 3.62 (s, 2H), 6.60 (t, J = 6.8 Hz, 1H), 6.86 (d, J = 6.8 Hz, 1H), 7.20 (t, J = 7.0 Hz, 1H), 7.28 (t, J = 7.0 Hz, 2H), 7.37 (d, J = 7.0 Hz, 2H), 7.65 (d J = 8.0 Hz, 2H), 7.85 (d, 8.0 Hz, 2H), 8.00 (s, 1H), 8.15 (d, J = 6.3 Hz, 1H), 9.82 (s, 1H) |
| III-1014 | 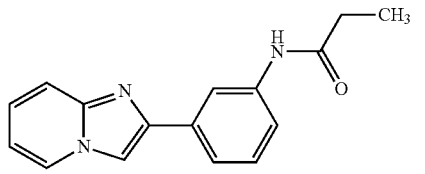 [SMILES: CCC(=O)Nc1cccc(-c2cn3ccccc3n2)c1] | ¹H NMR (DMSO, 400 MHz) δ: 1.15 (t, J = 7.8 Hz, 3H), 2.32 (qv, J = 7.8 Hz, 2H), 6.83 (t, J = 6.3 Hz, 1H), 7.11 (t, J = 6.8 Hz, 1H), 7.26 (t, J = 6.6 Hz, 1H), 7.51 (d, J = 6.8 Hz, 1H), 7.54 (d, J = 6.6 Hz, 1H), 7.61 (d, J = 6.3 Hz, 1H), 8.15 (s, 2H), 8.40 (d, J = 5.7 Hz, 1H), 9.62 (br s, 1H) |
| III-1015 | 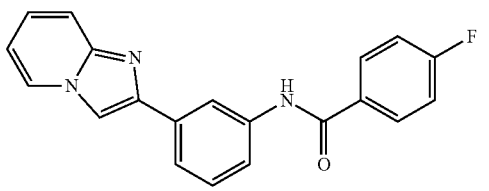 [SMILES: O=C(Nc1cccc(-c2cn3ccccc3n2)c1)c1ccc(F)cc1] | ¹H NMR (DMSO, 400 MHz) δ: 6.72 (t, J = 7.2 Hz, 1H), 7.04-7.23 (m, 3H), 7.49 (d, J = 8.4 Hz, 1H), 7.75-7.96 (m, 4H), 8.08 (br s, 3H), 8.34 (d, J = 5.6 Hz, 1H), 10.01 (br s, 1H) |
| III-1016 | 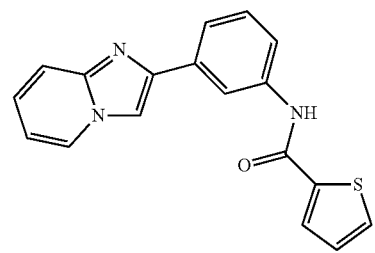 [SMILES: O=C(Nc1cccc(-c2cn3ccccc3n2)c1)c1cccs1] | ¹H NMR (DMSO, 400 MHz) δ: 6.82 (t, J = 6.2 Hz, 1H), 7.16 (t, J = 4.8 Hz, 1H), 7.22 (t, J = 6.8 Hz, 1H), 7.34 (t, J = 7.8 Hz, 1H), 7.51-7.70 (m, 3H), 7.81 (d, J = 7.8 Hz, 1H), 8.06 (br s, 1H), 8.25 (s, 1H), 8.33 (s, 1H), 8.48 (d, J = 5.8 Hz, 1H), 10.14 (br s, 1H) |

TABLE 5-continued

Spectral data for compounds of the general formula III.

| No | Formula | $^1$H NMR DMSO-d6, δ, ppm; LCMS, m/z (M + 1) |
|---|---|---|
| III-1017 | | $^1$H NMR (DMSO, 300 MHz) δ: 2.38 (s, 3H), 2.71 (s, 3H), 6.72 (d, J = 6.8 Hz, 1H), 7.32 (s, 1H), 7.37 (t, J = 7.2 Hz, 1H), 7.47-7.57 (m, 3H), 7.62-7.70 (m, 2H), 7.94-8.03 (m, 2H), 8.24 (s, 1H), 8.32 (s, 1H), 8.41 (d, J = 6.6 Hz, 1H), 10.28 (br s, 1H) |
| III-1018 | | $^1$H NMR (DMSO, 400 MHz) δ: 3.83 (s, 1H), 6.86 (d, J = 8.8 Hz, 2H), 7.25 (t, J = 6.8 Hz, 1H), 7.42 (t, J = 8.2 Hz, 1H), 7.68 (t, J = 6.8 Hz, 1H), 7.75-7.84 (m, 2H), 7.92 (d, J = 8.2 Hz, 1H), 8.02 (d, J = 8.8 Hz, 2H), 8.51 (s, 1H), 8.61 (s, 1H), 8.81 (d, J = 6.4 Hz, 1H), 10.41 (br s, 1H) |
| III-1019 | | $^1$H NMR (DMSO, 400 MHz) δ: 2.61 (s, 3H), 3.83 (s, 1H), 6.62 (t, J = 6.8 Hz, 1H), 6.95 (d, J = 8.6 Hz, 2H), 7.08-7.15 (m, 1H), 7.31 (t, J = 7.8 Hz, 1H), 7.42 (d, J = 8.6 Hz, 1H), 7.65 (d, J = 7.8 Hz, 1H), 7.80 (d, J = 7.8 Hz, 1H), 7.98-8.04 (m, 3H), 8.36 (s, 1H), 9.91 (br s, 1H) |
| III-1020 | | $^1$H NMR (DMSO, 400 MHz) δ: 2.58 (s, 3H), 6.68 (t, J = 6.7 Hz, 1H), 6.94 (d, J = 6.7 Hz, 1H), 7.33 (t, J = 8.1 Hz, 1H), 7.40-7.47 (m, 1H), 7.67 (d, J = 7.4 Hz, 1H), 7.81 (d, J = 7.4 Hz, 1H), 8.15 (s, 1H), 8.25-8.37 (m, 3H), 8.70 (d, J = 4.0 Hz, 1H), 9.15 (d, J = 2.4 Hz, 1H), 10.18 (br s, 1H) |
| III-1021 | | $^1$H NMR (DMSO, 400 MHz) δ: 2.04 (s, 3H), 2.62 (s, 3H), 6.61 (d, J = 6.7 Hz, 1H), 7.05-7.12 (m, 1H), 7.24 (t, J = 7.9 Hz, 1H), 7.39 (d, J = 8.8 Hz, 1H), 7.57 (d, J = 7.9 Hz, 1H), 7.63 (d, J = 7.9 Hz, 1H), 7.94 (s, 1H), 8.13 (s, H), 9.71 (s, 1H) |
| III-1022 | | $^1$H NMR (DMSO, 400 MHz) δ: 2.69 (s, 3H), 6.61 (d, J = 6.6 Hz, 1H), 7.08-7.15 (m, 2H), 7.32 (t, J = 7.8 Hz, 1H), 7.41 (d, J = 8.7 Hz, 1H), 7.58 (d, J = 4.9 Hz, 1H), 7.66 (d, J = 7.8 Hz, 1H), 7.80 (d, J = 7.8 Hz, 1H), 8.01-8.06 (m, 2H), 8.32 (s, 1H), 10.09 (s, 1H) |

TABLE 5-continued

Spectral data for compounds of the general formula III.

| No | Formula | ¹H NMR DMSO-d6, δ, ppm; LCMS, m/z (M + 1) |
|---|---|---|
| III-1023 | 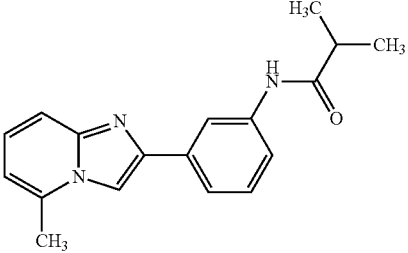 [SMILES: Cc1cccc2nc(-c3cccc(NC(=O)C(C)C)c3)cn12] | ¹H NMR (DMSO, 400 MHz) δ: 1.12 (d, J = 6.7 Hz, 6H), 2.56 (s, J = 6.7 Hz, 1H), 2.62 (s, 3H), 6.61 (d, J = 6.6 Hz, 1H), 7.07-7.14 (m, 1H), 7.26 (t, J = 7.6 Hz, 1H), 7.40 (d, J = 8.7 Hz, 1H), 7.58 (d, J = 7.7 Hz, 1H), 7.63 (d, J = 7.7 Hz, 1H), 7.97 (s, 1H), 8.18 (s, 1H), 9.62 (s, 1H) |
| III-1024 | 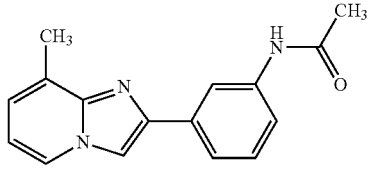 [SMILES: CC(=O)Nc1cccc(-c2cn3cccc(C)c3n2)c1] | ¹H NMR (DMSO, 400 MHz) δ: 2.02 (s, 3H), 2.58 (s, 3H), 6.64 (t, J = 6.8 Hz, 1H), 6.89 (d, J = 6.8 Hz, 1H), 7.24 (t, J = 7.8 Hz, 1H), 7.56 (d, J = 7.8 Hz, 1H), 7.63 (d, J = 7.8 Hz, 1H), 8.04 (s, 1H), 8.09 (s, 1H), 8.23 (d, J = 6.4 Hz, 1H), 9.77 (s, 1H) |
| III-1025 | 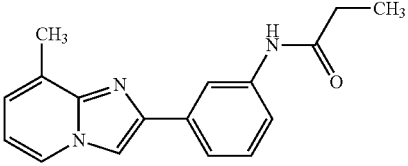 [SMILES: CCC(=O)Nc1cccc(-c2cn3cccc(C)c3n2)c1] | ¹H NMR (DMSO, 400 MHz) δ: 1.12 (t, J = 7.4 Hz, 3H), 2.33 (q, J = 7.4 Hz, 2H), 2.56 (s, 3H), 6.63 (t, J = 6.8 Hz, 1H), 6.89 (d, J = 6.8 Hz, 1H), 7.24 (t, J = 7.8 Hz, 1H), 7.58 (d, J = 6.8 Hz, 1H), 7.64 (d, J = 6.8 Hz, 1H), 8.07 (s, 1H), 8.10 (s, 1H), 8.23 (d, J = 6.4 Hz, 1H), 9.69 (s, 1H) |
| III-1026 | 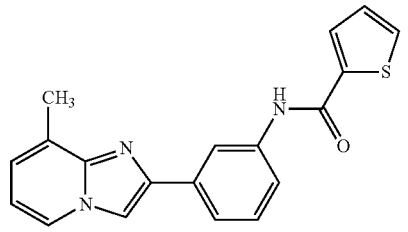 [SMILES: Cc1cccn2cc(-c3cccc(NC(=O)c4cccs4)c3)nc12] | ¹H NMR (DMSO, 400 MHz) δ: 2.63 (s, 3H), 6.85 (t, J = 6.8 Hz, 1H), 7.09-7.16 (m, 2H), 7.32 (t, J = 7.9 Hz, 1H), 7.59 (d, J = 4.9 Hz, 1H), 7.73 (d, J = 7.8 Hz, 1H), 7.81 (d, J = 7.8 Hz, 1H), 8.14 (d, J = 3.4 Hz, 1H), 8.32-8.36 (m, 2H), 8.43 (d, J = 6.4 Hz, 1H), 10.30 (s, 1H) |
| III-1027 | 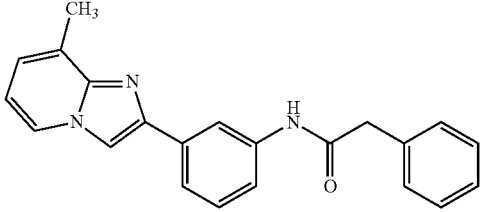 [SMILES: Cc1cccn2cc(-c3cccc(NC(=O)Cc4ccccc4)c3)nc12] | ¹H NMR (DMSO, 400 MHz) δ: 2.53 (s, 3H), 3.60 (s, 2H), 6.63 (t, J = 6.8 Hz, 1H), 6.89 (d, J = 6.8 Hz, 1H), 7.19 (t, J = 7.3 Hz, 1H), 7.21-7.32 (m, 3H), 7.37 (d, J = 7.6 Hz, 2H), 7.56 (d, J = 7.8 Hz, 1H), 7.65 (d, J = 7.8 Hz, 1H), 8.10 (s, 1H), 8.12 (s, 1H), 8.22 (d, J = 6.4 Hz, 1H), 10.03 (s, 1H) |
| III-1028 | 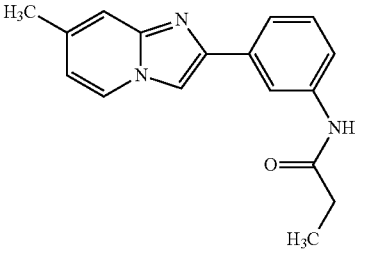 [SMILES: CCC(=O)Nc1cccc(-c2cn3ccc(C)cc3n2)c1] | ¹H NMR (DMSO, 300 MHz) δ: 1.19 (t, J = 7.4 Hz, 3H), 2.32 (qv, J = 7.4 Hz, 2H), 2.39 (s, 3H), 6.57 (t, J = 6.8 Hz, 1H), 7.21-7.28 (m, 2H), 7.52 (d, J = 7.7 Hz, 1H), 7.63 (d, J = 7.7 Hz, 1H), 8.02 (s, 1H), 8.12 (s, 1H), 8.26 (d, J = 6.8 Hz, 1H), 9.62 (s, 1H) |

TABLE 5-continued
Spectral data for compounds of the general formula III.
| No | Formula | $^1$H NMR DMSO-d6, δ, ppm; LCMS, m/z (M + 1) |
|---|---|---|
| III-1029 | 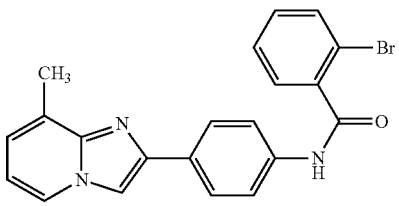 [SMILES: Cc1cccn2cc(-c3ccc(NC(=O)c4ccccc4Br)cc3)nc12] | $^1$H NMR (DMSO, 400 MHz) δ: 2.61 (s, 3H), 6.63 (t, J = 6.8 Hz, 1H), 6.89 (d, J = 6.8 Hz, 1H), 7.33 (t, J = 7.8 Hz, 1H), 7.43 (t, J = 7.8 Hz, 1H), 7.53 (d, J = 7.8 Hz, 1H), 7.63 (d, J = 7.8 Hz, 1H), 7.79 (d, J = 8.3 Hz, 2H), 7.92 (d, J = 8.3 Hz, 2H), 8.06 (s, 1H), 8.18 (d, J = 6.6 Hz, 1H), 10.18 (s, 1H); LCMS m/z 408 (M + 1) |
| III-1030 | 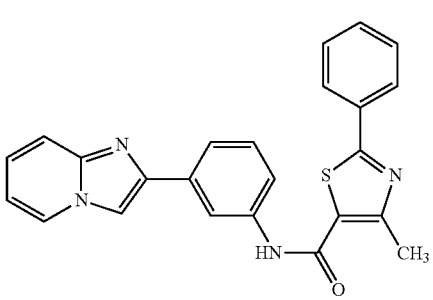 [SMILES: Cc1nc(-c2ccccc2)sc1C(=O)Nc1cccc(-c2cn3ccccc3n2)c1] | LCMS m/z 411 (M + 1) |
| III-1031 | 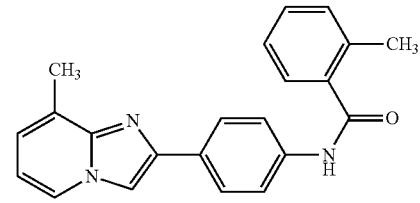 [SMILES: Cc1ccccc1C(=O)Nc1ccc(-c2cn3cccc(C)c3n2)cc1] | LCMS m/z 342 (M + 1) |
| III-1032 | 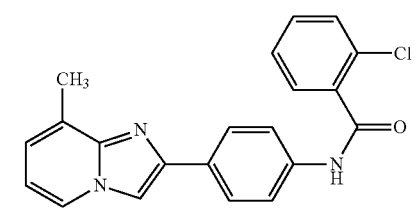 [SMILES: Cc1cccn2cc(-c3ccc(NC(=O)c4ccccc4Cl)cc3)nc12] | LCMS m/z 362 (M + 1) |
| III-1033 | 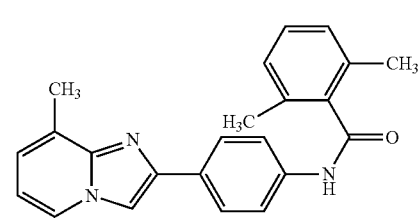 [SMILES: Cc1cccc(C)c1C(=O)Nc1ccc(-c2cn3cccc(C)c3n2)cc1] | LCMS m/z 356 (M + 1) |
| III-1034 | 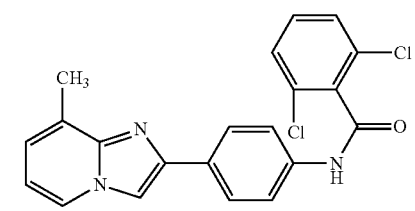 [SMILES: Cc1cccn2cc(-c3ccc(NC(=O)c4c(Cl)cccc4Cl)cc3)nc12] | LCMS m/z 397 (M + 1) |

TABLE 5-continued
Spectral data for compounds of the general formula III.
| No | Formula | $^1$H NMR DMSO-d6, δ, ppm; LCMS, m/z (M + 1) |
|---|---|---|
| III-1035 | 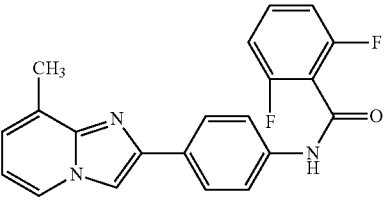 [SMILES: Cc1cccn2cc(-c3ccc(NC(=O)c4c(F)cccc4F)cc3)nc12] | LCMS m/z 364 (M + 1) |
| III-1036 | 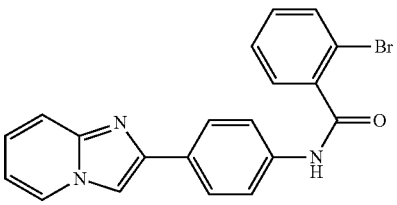 [SMILES: O=C(Nc1ccc(-c2cn3ccccc3n2)cc1)c1ccccc1Br] | LCMS m/z 393 (M + 1) |
| III-1037 | 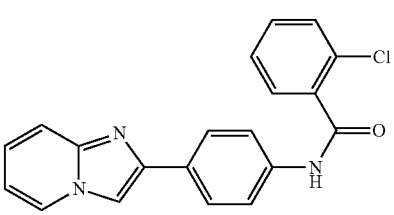 [SMILES: O=C(Nc1ccc(-c2cn3ccccc3n2)cc1)c1ccccc1Cl] | LCMS m/z 349 (M + 1) |
| III-1038 | 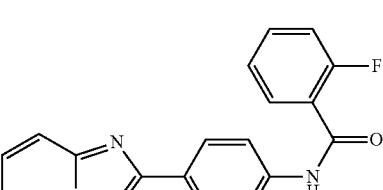 | LCMS m/z 332 (M + 1) |
| III-1039 | 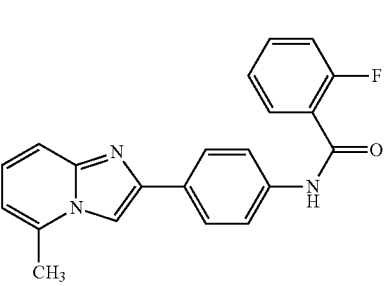 [SMILES: Cc1cccc2nc(-c3ccc(NC(=O)c4ccccc4F)cc3)cn12] | LCMS m/z 346 (M + 1) |
| III-1040 | 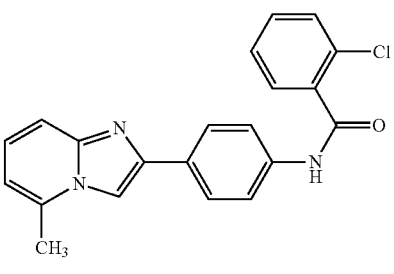 [SMILES: Cc1cccc2nc(-c3ccc(NC(=O)c4ccccc4Cl)cc3)cn12] | LCMS m/z 362 (M + 1) |

TABLE 5-continued

Spectral data for compounds of the general formula III.

| No | Formula | ¹H NMR DMSO-d6, δ, ppm; LCMS, m/z (M + 1) |
|---|---|---|
| III-1041 | 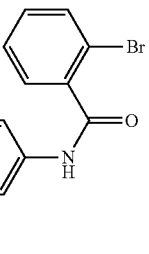 | LCMS m/z 408 (M + 1) |
| III-1042 | 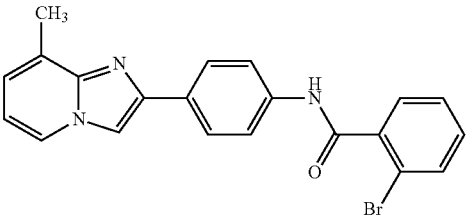 | LCMS m/z 409 (M + 1) |
| III-1043 | 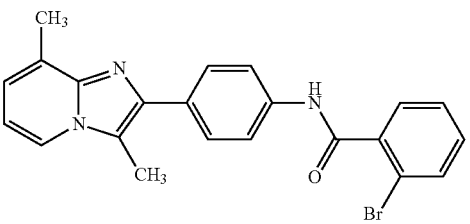 [SMILES: Cc1cccn2c(C)c(-c3ccc(NC(=O)c4ccccc4Br)cc3)nc12] | LCMS m/z 422 (M + 1) |

EXAMPLE 6

Synthesis of Compounds of the General Formula IV (Scheme 4)

Compounds d3. The solution of compounds d1 (0.1 mol) and d2 (0.1 mol) in acetone (50 ml) was boiled for 2 hours and cooled to 0° C., the solid precipitated was filtered off and washed with acetone and ether. The product was dissolved in soda solution (0.1 mol in 300 ml of water). The solution obtained was boiled for 1 hour and cooled to 0-5° C. The solid was filtered off, washed with icy water and dried in the opened air. The yield of compounds d3 was 60-65%.

Compounds d4. Compound d3 (0.1 mol) was suspended in the solution of HCl (0.2 mol in 100 ml of water and 5 ml of ethanol). The reaction mixture was boiled until complete dissolution of solid, cooled to room temperature and basified with 5% water solution of NaOH. The solid precipitated was filtered off, washed with water, dried in the opened air and recrystallised from ethanol. The yield of compounds d4 was 60-65%.

Compounds of the general formula IV. Aniline d4 (1 mmol) was added to the solution of carboxylic acid chloride (1 mmol) and pyridine (1.1 mmol) in dioxane (5 ml). The reaction mixture was stirred at 45-55° C. for 4 hours and left for a night at room temperature. After that it was poured into 10-fold volume of water, the precipitated solid was filtered off, washed with water, dried in the opened air and recrystallized from isopropanol. The yield of compounds of the general formula IV was 65-90%, some of them are presented in Table 6.

TABLE 6

Spectral data for compounds of the general formula IV.

| No | Formula | ¹H NMR DMSO-d6, δ, ppm; LCMS, m/z (M + 1) |
|---|---|---|
| IV-1001 | 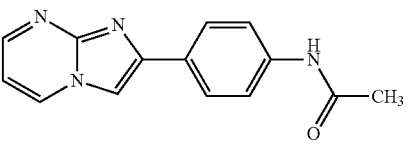 [SMILES: CC(=O)Nc1ccc(-c2cn3cccnc3n2)cc1] | ¹H NMR (DMSO, 400 MHz) δ: 2.09 (s, 3H), 6.95-6.99 (m, 1H), 7.65 (d, J = 8.3 Hz, 2H), 7.86 (d, J = 8.3 Hz, 2H), 8.20 (s, 1H), 8.45 (s, 1H), 8.81 (d, J = 6.8 Hz, 1H), 9.93 (s, 1H) |

US 8,486,945 B2

TABLE 6-continued

Spectral data for compounds of the general formula IV.

| No | Formula | $^1$H NMR DMSO-d6, δ, ppm; LCMS, m/z (M + 1) |
|---|---|---|
| IV-1002 | 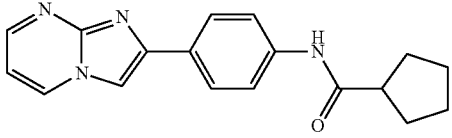 [SMILES: O=C(Nc1ccc(-c2cn3cccnc3n2)cc1)C1CCCC1] | $^1$H NMR (DMSO, 400 MHz) δ: 1.50-1.65 (m, 2H), 1.67-1.95 (m, 6H), 2.50-2.60 (m, 1H), 6.91-6.98 (m, 1H), 7.67 (d, J = 8.3 Hz, 2H), 7.87 (d, J = 8.3 Hz, 2H), 8.18 (s, 1H), 8.44 (s, 1H), 8.90 (d, J = 6.8 Hz, 1H), 9.77 (s, 1H) |
| IV-1003 | 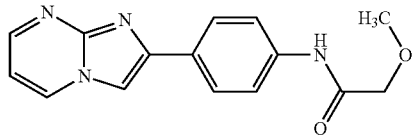 [SMILES: COCC(=O)Nc1ccc(-c2cn3cccnc3n2)cc1] | $^1$H NMR (DMSO, 400 MHz) δ: 3.44 (s, 3H), 4.00 (s, 2H), 6.97-7.01 (m, 1H), 7.76 (d, J = 8.3 Hz, 2H), 7.92 (d, J = 8.3 Hz, 2H), 8.24 (s, 1H), 8.46 (br s, 1H), 8.93 (d, J = 6.8 Hz, 1H), 9.74 (s, 1H) |
| IV-1004 | 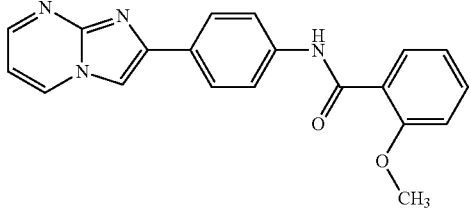 [SMILES: COc1ccccc1C(=O)Nc1ccc(-c2cn3cccnc3n2)cc1] | $^1$H NMR (DMSO, 400 MHz) δ: 3.95 (s, 3H), 7.02-7.12 (m, 2H), 7.20 (d, J = 8.3 Hz, 2H), 7.50 (t, J = 8.1 Hz, 2H), 7.65 (d, J = 8.1 Hz, 2H), 7.86 (d, J = 8.3 Hz, 2H), 8.00 (d, J = 8.3 Hz, 2H), 8.34 (s, 1H), 8.52 (br s, 1H), 8.95 (d, J = 6.8 Hz, 1H), 10.27 (s, 1H) |
| IV-1005 | 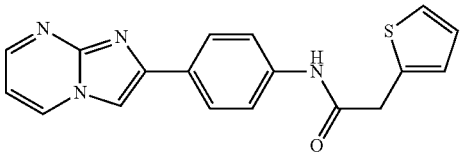 [SMILES: O=C(Cc1cccs1)Nc1ccc(-c2cn3cccnc3n2)cc1] | $^1$H NMR (DMSO, 400 MHz) δ: 3.86 (s, 2H), 6.92-7.00 (m, 3H), 7.26 (d, J = 5.4 Hz, 1H), 7.67 (d, J = 8.3 Hz, 2H), 7.90 (d, J = 8.3 Hz, 2H), 8.19 (s, 1H), 8.42-8.47 (m, 1H), 8.91 (d, J = 6.8 Hz, 1H), 10.18 (s, 1H) |
| IV-1006 | 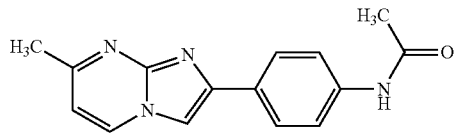 [SMILES: CC(=O)Nc1ccc(-c2cn3ccc(C)nc3n2)cc1] | $^1$H NMR (DMSO, 400 MHz) δ: 2.06 (s, 3H), 2.52 (s, 3H), 6.92 (d, J = 6.8 Hz, 1H), 7.65 (d, J = 8.3 Hz, 2H), 7.88 (d, J = 8.3 Hz, 2H), 8.16 (s, 1H), 8.78 (d, J = 6.8 Hz, 1H), 10.04 (s, 1H) |
| IV-1007 | 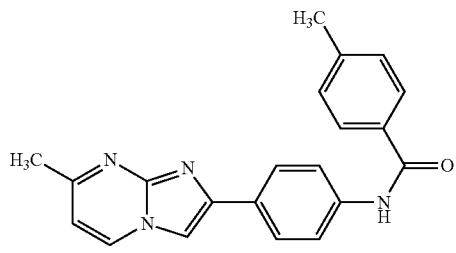 [SMILES: Cc1ccc(C(=O)Nc2ccc(-c3cn4ccc(C)nc4n3)cc2)cc1] | $^1$H NMR (DMSO, 400 MHz) δ: 2.41 (s, 3H), 2.55 (s, 3H), 6.85 (d, J = 6.8 Hz, 1H), 7.30 (d, J = 8.3 Hz, 2H), 7.75-7.98 (m, 6H), 8.20 (s, 1H), 8.76 (d, J = 6.8 Hz, 1H), 10.09 (br s, 1H) |
| IV-1008 | 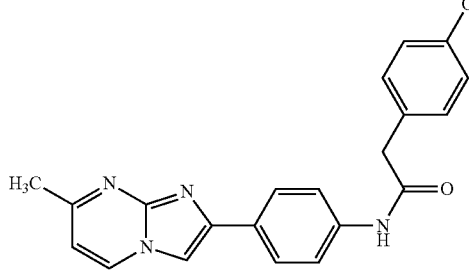 | $^1$H NMR (DMSO, 400 MHz) δ: 2.52 (s, 3H), 3.58 (s, 2H), 3.72 (s, 3H), 6.87-6.92 (m, 3H), 7.26 (d, J = 8.3 Hz, 2H), 7.67 (d, J = 8.7 Hz, 2H), 7.88 (d, J = 8.7 Hz, 2H), 8.16 (s, 1H), 8.77 (d, J = 6.8 Hz, 1H), 10.22 (s, 1H) |

TABLE 6-continued

Spectral data for compounds of the general formula IV.

| No | Formula | ¹H NMR DMSO-d6, δ, ppm; LCMS, m/z (M + 1) |
|---|---|---|
| IV-1009 | 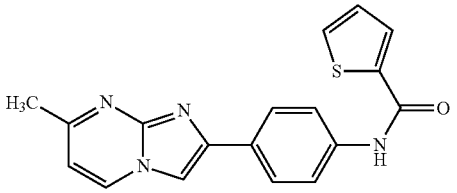 [SMILES: Cc1ccn2cc(-c3ccc(NC(=O)c4cccs4)cc3)nc2n1] | ¹H NMR (DMSO, 400 MHz) δ: 2.55 (s, 3H), 6.84 (d, J = 6.8 Hz, 1H), 7.11-7.23 (m, 1H), 7.72 (d, J = 6.1 Hz, 1H), 7.77 (d, J = 8.3 Hz, 2H), 7.88 (d, J = 8.3 Hz, 2H), 7.96 -8.03 (m, 1H), 8.19 (s, 1H), 8.75 (d, J = 6.8 Hz, 1H), 10.17 (s, 1H) |
| IV-1010 | 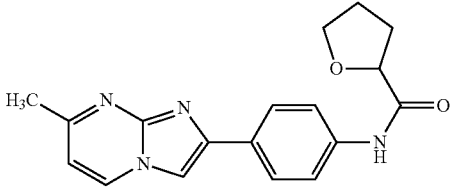 [SMILES: Cc1ccn2cc(-c3ccc(NC(=O)C4CCCO4)cc3)nc2n1] | ¹H NMR (DMSO, 400 MHz) δ: 1.80-1.90 (m, 2H), 1.95-2.06 (m, 1H), 2.14-2.25 (m, 1H), 2.52 (s, 3H), 3.80-3.87 (m, 1H), 3.94-4.05 (m, 1H), 4.37-4.45 (m, 1H), 6.92 (d, J = 6.8 Hz, 1H), 7.77 (d, J = 8.3 Hz, 2H), 7.89 (d, J = 8.3 Hz, 2H), 8.18 (s, 1H), 8.78 (d, J = 6.8 Hz, 1H), 9.76 (s, 1H) |
| IV-1011 | 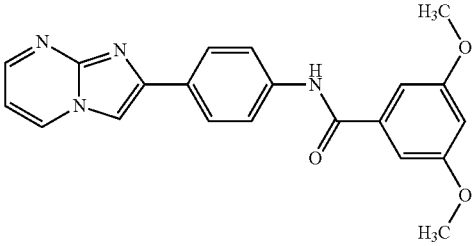 [SMILES: COc1cc(OC)cc(C(=O)Nc2ccc(-c3cn4cccnc4n3)cc2)c1] | ¹H NMR (DMSO, 400 MHz) δ: 3.85 (s, 6H), 6.73 (s, 1H), 7.02-7.08 (m, 1H), 7.13 (s, 2H), 7.88 (d, J = 8.5 Hz, 2H), 8.00 (d, J = 8.3 Hz, 2H), 8.34 (s, 1H), 8.52 (br s, 1H), 8.95 (d, J = 7.0 Hz, 1H), 10.30 (sc, 1H) |
| IV-1012 | 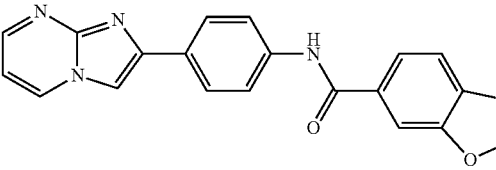 | ¹H NMR (DMSO, 400 MHz) δ: 6.15 (s, 2H), 7.00-7.13 (m, 2H), 7.54 (s, 1H), 7.61 (d, J = 6.8 Hz, 1H), 7.88 (d, J = 8.3 Hz, 2H), 8.00 (d, J = 8.35 Hz, 2H), 8.33 (s, 1H), 8.52 (br s, 1H), 8.95 (d, J = 6.8 Hz, 1H), 10.19 (s, 1H) |
| IV-1013 | 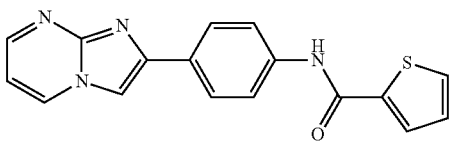 [SMILES: O=C(Nc1ccc(-c2cn3cccnc3n2)cc1)c1cccs1] | ¹H NMR (DMSO, 400 MHz) δ: 6.91-7.08 (m, 1H), 7.15-7.26 (m, 1H), 7.78 (d, J = 5.3 Hz, 1H), 7.84 (d, J = 8.3 Hz, 2H), 7.97 (d, J = 8.3 Hz, 2H), 8.04 (d, J = 5.0 Hz, 1H), 8.27 (s, 1H), 8.52 (br s, 1H), 8.95 (d, J = 6.8 Hz, 1H), 10.27 (s, 1H) |
| IV-1014 | 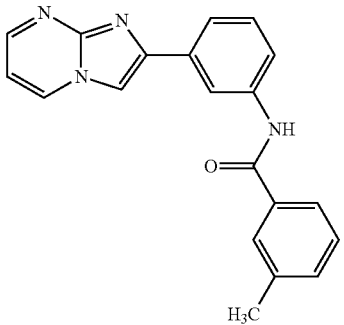 [SMILES: Cc1cccc(C(=O)Nc2cccc(-c3cn4cccnc4n3)c2)c1] | ¹H NMR (DMSO, 400 MHz) δ: 2.44 (s, 3H), 7.00-7.07 (m, 1H), 7.35-7.47 (m, 3H), 7.70 (d, J = 8.0 Hz, 1H), 7.54-7.88 (m, 3H), 8.30 (s, 1H), 8.46 (s, 1H), 8.49-8.55 (m, 2H), 8.97 (dd, J = 7.7 Hz, J = 2.2 Hz, 1H), 10.25 (s, 1H) |

TABLE 6-continued

Spectral data for compounds of the general formula IV.

| No | Formula | ¹H NMR DMSO-d6, δ, ppm; LCMS, m/z (M + 1) |
|---|---|---|
| IV-1015 | | ¹H NMR (DMSO, 400 MHz) δ: 3.87 (s, 2H), 6.88-7.07 (m, 3H), 7.27 (d, J = 5.4 Hz, 1H), 7.33 (t, J = 8.4 Hz, 1H), 7.61 (d, J = 8.4 Hz, 2H), 8.24 (s, 2H), 8.47 (br s, 1H), 8.92 (d, J = 6.8 Hz, 1H), 10.22 (s, 1H) |
| IV-1016 | | ¹H NMR (DMSO, 400 MHz) δ: 1.52-1.66 (m, 2H), 1.68-1.95 (m, 6H), 2.67-2.77 (m, 1H), 6.93-7.00 (m, 1H), 7.31 (t, J = 8.3 Hz, 1H), 7.59 (d, J = 8.3 Hz, 1H), 7.64 (d, J = 8.3 Hz, 1H), 8.23 (s, 1H), 8.24 (s, 1H), 8.40-8.50 (m, 1H), 8.92 (d, J = 7.0 Hz, 1H), 9.82 (s, 1H) |
| IV-1017 | | ¹H NMR (DMSO, 400 MHz) δ: 6.64-6.70 (m, 1H), 6.98-7.06 (m, 1H), 7.34-7.43 (m, 2H), 7.70 (d, J = 8.3 Hz, 1H), 7.81 (d, J = 8.3 Hz, 1H), 7.87 (s, 1H), 8.29 (s, 1H), 8.42 (s, 1H), 8.52 (br s, 1H), 8.96 (d, J = 6.8 Hz, 1H), 10.20 (s, 1H) |
| IV-1018 | | ¹H NMR (DMSO, 400 MHz) δ: 1.17 (d, J = 6.4 Hz, 6H), 2.23 (s, 3H), 2.60-2.76 (m, 1H), 6.96-7.05 (m, 1H), 7.25 (d, J = 8.0 Hz, 1H), 7.67 (d, J = 8.0 Hz, 1H), 7.97 (s, 1H), 8.24 (s, 1H), 8.46 (br s, 1H), 8.90 (d, J = 6.8 Hz, 1H), 9.18 (br s, 1H) |
| IV-1019 | | ¹H NMR (DMSO, 400 MHz) δ: 2.29 (s, 3H), 3.89 (s, 3H), 6.80-7.09 (m, 3H), 7.34 (d, J = 8.4 Hz, 1H), 7.77 (d, J = 8.4 Hz, 1H), 7.95-8.08 (m, 3H), 8.30 (s, 1H), 8.49 (br s, 1H), 8.94 (d, J = 6.8 Hz, 1H), 9.78 (br s, 1H) |

TABLE 6-continued

Spectral data for compounds of the general formula IV.

| No | Formula | ¹H NMR DMSO-d6, δ, ppm; LCMS, m/z (M + 1) |
|---|---|---|
| IV-1020 | | ¹H NMR (DMSO, 400 MHz) δ: 2.22 (s, 3H), 2.35 (s, 3H), 3.65 (s, 2H), 6.66-7.04 (m, 2H), 7.05-7.13 (m, 4H), 7.68 (d, J = 8.2 Hz, 1H), 8.03 (s, 1H), 8.23 (s, 1H), 8.47 (br s, 1H), 8.90 (d, J = 6.8 Hz, 1H), 9.43 (br s, 1H) |
| IV-1021 | | ¹H NMR (DMSO, 400 MHz) δ: 2.29 (s, 3H), 6.94-7.12 (m, 1H), 7.20 (t, J = 6.2 Hz, 1H), 7.34 (d, J = 8.4 Hz, 1H) 7.72-7.84 (m, 2H), 7.94-8.04 (m, 2H), 8.31 (s, 1H), 8.49 (br s, 1H), 8.93 (d, J = 6.8 Hz, 1H), 9.97 (br s, 1H) |
| IV-1022 | | ¹H NMR (DMSO, 400 MHz) δ: 2.15 (s, 3H), 3.88 (s, 3H), 6.92-7.00 (m, 1H), 7.04 (d, J = 8.1 Hz, 1H), 7.69 (d, J = 8.4 Hz, 1H), 8.15 (s, 1H), 8.44 (br s, 1H), 8.59 (s, 1H), 8.90 (d, J = 6.8 Hz, 1H), 9.04 (br s, 1H) |
| IV-1023 | | ¹H NMR (DMSO, 400 MHz) δ: 0.70-0.83 (m, 2H), 0.84-0.94 (2H), 2.02-2.16 (m, 1H), 3.93 (s, 3H), 6.95-7.01 (m, 1H), 7.09 (d, J = 8.4 Hz, 1H), 7.70 (dd, J = 8.4 Hz, J = 2.1 Hz, 1H), 8.17 (s, 1H), 8.46 (br s, 1H), 8.61 (s, 1H), 8.90 (d, J = 6.7 Hz, 1H), 9.32 (s, 1H) |
| IV-1024 | | ¹H NMR (DMSO, 400 MHz) δ: 3.85 (s, 3H), 3.91 (s, 3H), 6.98-7.05 (m, 1H), 7.10-7.22 (m, 2H), 7.44 (t, J = 8.4 Hz, 1H), 7.49-7.60 (m, 2H), 7.82 (d, J = 8.4 Hz, 1H), 8.25 (s, 1H), 8.50 (br s, 1H), 8.93 (d, J = 6.8 Hz, 1H), 9.36 (br s, 1H) |

TABLE 6-continued

Spectral data for compounds of the general formula IV.

| No | Formula | $^1$H NMR DMSO-d6, δ, ppm; LCMS, m/z (M + 1) |
|---|---|---|
| IV-1025 | (imidazo[1,2-a]pyrimidine linked to methoxyphenyl with NHC(O)CH$_2$-phenyl substituent) | $^1$H NMR (DMSO, 400 MHz) δ: 3.77 (s, 2H), 3.93 (s, 3H), 6.90-7.00 (m, 1H), 7.05 (d, J = 8.4 Hz, 1H), 7.17-7.45 (m, 5H), 7.70 (d, J = 8.4 Hz, 1H), 8.14 (s, 1H), 8.43 (br s, 1H), 8.62 (s, 1H), 8.87 (d, J = 6.8 Hz, 1H), 9.10 (br s, 1H) |
| IV-1026 | (imidazo[1,2-a]pyrimidine linked to methoxyphenyl with NHC(O)-furan-2-yl substituent) | $^1$H NMR (DMSO, 400 MHz) δ: 3.96 (s, 3H), 6.70 (br s, 1H), 6.95-7.05 (m, 1H), 7.17 (d, J = 8.3 Hz, 1H), 7.29 (d, J = 5.1 Hz, 1H), 7.98 (d, J = 8.3 Hz, 1H), 7.89 (s, 1H), 8.23 (s, 1H), 8.48 (br s, 1H), 8.72 (s, 1H), 8.93 (d, J = 6.7 Hz, 1H), 9.04 (br s, 1H) |

EXAMPLE 7

Synthesis of Compounds of the General Formula V (Scheme 5)

Compounds e2. Mixture of thiophencarbaldehyde e1 (1 mol) and azidoacetic ester (1 mol) was added drop by drop to the solution of sodium methylate (1 mol sodium in 300 ml of abs. methanol) at vigorous stirring so that the temperature of the reaction mixture did not exceed −10-5° C. The resultant mixture was left for 12-15 hours at 0° C. and poured into water solution of NH$_4$Cl (1 mol in 1000 ml of water). The precipitated solid was filtered off and dried in vacuum. Oily products were extracted three times with methylene chloride, combined extracts were washed with water, dried over MgSO$_4$ and evaporated at reduced pressure and temperature below 50° C. Crude product e2 prepared in this way with 67-75% yield was used in the next stage without additional purification.

Compounds e3. Dry crude product e2 (1 mol) was dissolved in absolute toluene (1000 ml) and carefully warmed till the beginning of exothermic reaction. The reaction was accompanied by considerable effervescence of nitrogen. After vigorous gas evolution was over the reaction mixture was carefully warmed at stirring until full completion of gas evolution, after that it was boiled for additional hour. Then the reaction mixture was cooled to 0° C., the precipitated solid was filtered off, washed with cold toluene and dried in the opened air. The yield of compounds e3 was 85-95%.

Compounds e4. Dried K$_2$CO$_3$ (0.15 mol), alkylating agent (0.1 mol) and crown-16 (0.5 mmol) were added to the solution of compound e3 (0.1 mol) in DMF (100 ml). The suspension obtained was stirred at 80-90° C. for 4 hours, cooled to room temperature and poured into 10-fold volume of water. The precipitated solid was filtered off, washed with water, dried in the opened air and recrystallized from ethanol. The oily products were extracted three times with methylene chloride, combined extracts were washed with water, dried over MgSO$_4$ and evaporated at reduced pressure. The residue was recrystallized from ethanol. If required, recrystallization was repeated from the proper solvent. The yield of compounds e4 was 30-75%.

Compounds e5. Saturated water solution of KOH (1.2 mol) was added to the solution of compound e4 (1 mol) in methanol (1000 ml). The mixture obtained was boiled for 3 hours and evaporated at reduced pressure nearly to dryness. The residue was dissolved in water (500 ml) and the solution was acidified with 10% solution of HCl to pH=3. The precipitated solid was filtered off, washed with water and dried in the opened air. The yield of acids was 75-80%. Then 1,1'-carbonyldiimidazole (0.55 mol) was added in portions to the solution of acid (0.5 mol) in absolute DMF (500 ml) and the resultant mixture was stirred at 60° C. for 1 hour without air access. Then isonipicotic ester (0.60 mol) was added to the mixture and stirring was continued at 100° C. for 2 hours without air access. After cooling to room temperature the reaction mixture was poured into 10-fold volume of water, the solid precipitated was filtered off, washed with water and dried in the opened air. The yield of compounds e5 was 75-80%.

Compounds of the general formula V. Saturated water solution of KOH (1.2 mol) was added to the solution of compound e5 (0.1 mol) in methanol (200 ml). The mixture obtained was boiled for 3 hours and evaporated at reduced pressure nearly to dryness. The residue was dissolved in water (100 ml) and acidified with 10% solution of HCl to pH=3. The precipitated solid was filtered off, washed with water and dried in the opened air. The yield of the acids was 75-80%. Then 1,1'-carbonyldiimidazole (1.15 mmol) was added to the solution of the acid (1 mmol) in absolute DMF (5 ml) and the resultant mixture was stirred at 80° C. for 1 hour in nitrogen atmosphere. Then primary or secondary amine (1.4 mmol) was added to the mixture and stirring was continued at the same temperature for additional 6 hours. After cooling to room temperature the reaction mixture was poured into 3% solution of soda (50 ml) and stirred until solid precipitated. The latter was filtered off, washed twice with water and dried in the opened air. If required, the product was recrystallized from the proper solvent. The oily products were extracted with methylene chloride, combined extracts were washed twice with water, dried over MgSO$_4$ and evaporated at reduced pressure. The crude product was purified either by recrystallization from the proper solvent or by flash chromatography on silica gel. The yield of the amides of the general formula V was 20-85%, some of them are presented in Table 7.

TABLE 7

Spectral data for compounds of the general formula V.

| No | Formula | $^1$H NMR DMSO-d6, δ, ppm; LCMS, m/z (M + 1) |
|---|---|---|
| V-1001 | | $^1$H NMR (DMSO, 300 MHz) δ: 1.25-1.45 (m, 2H), 1.50-1.65 (m, 2H), 2.75-3.06 (m, 3H), 3.32-3.65 (m, 8H), 4.15-4.35 (m, 2H), 5.41 (s, 2H), 6.67 (s, 1H), 7.02-7.24 (m, 5H), 7.35 (d, J = 5.5 Hz, 1H); LCMS m/z 456 (M + 1); M.p. 120-122° C. |
| V-1002 | | $^1$H NMR (DMSO, 400 MHz) δ: 1.50-1.65 (m, 2H), 1.68-1.80 (m, 2H), 2.26 (s, 6H), 2.42-3.60 (m, 1H), 2.87-3.05 (m, 2H), 4.30-4.42 (m, 2H), 5.56 (s, 2H), 6.57 (s, 1H), 6.60 (s, 1H), 6.97-7.05 (m, 3H), 7.14-7.25 (m, 5H); LCMS m/z 490 (M + 1); M.p. 203-205° C. |
| V-1003 | | $^1$H NMR (DMSO, 400 MHz) δ: 1.57-1.70 (m, 2H), 1.75-1.87 (m, 2H), 2.33-2.45 (m, 1H), 2.94-3.08 (m, 2H), 3.82 (s, 3H), 4.32-4.44 (m, 2H), 6.43 (s, 1H), 6.47 (s, 1H), 6.93 (d, J = 5.4 Hz, 1H), 7.04 (s, 1H), 7.13 (d, J = 5.4 Hz, 1H) |
| V-1004 | | $^1$H NMR (DMSO, 400 MHz) δ: 1.34 (t, J = 6.9 Hz, 3H), 1.50-1.85 (m, 10H), 2.25-2.40 (m, 1H), 2.88-3.07 (m, 2H), 3.90-4.04 (m, 1H), 4.24 (qv, J = 6.9 Hz, 2H), 4.33-4.46 (m, 2H), 6.46 (s, 1H), 6.99 (d, J = 5.6 Hz, 1H), 7.15 (d, J = 5.6 Hz, 1H), 7.40 (br s, J = 6.9 Hz, 1H) |

TABLE 7-continued

Spectral data for compounds of the general formula V.

| No | Formula | $^1$H NMR DMSO-d6, δ, ppm; LCMS, m/z (M + 1) |
|---|---|---|
| V-1005 | | $^1$H NMR (DMSO, 400 MHz) δ: 1.34 (t, J = 6.9 Hz, 3H), 1.55-1.70 (m, 2H), 1.72-1.88 (m, 2H), 2.39-2.51 (m, 1H), 2.95-3.10 (m, 2H), 4.18-4.30 (m, 4H), 4.33-4.44 (m, 2H), 6.13 (br s, 1H), 6.28 (br s, 1H), 6.47 (s, 1H), 6.99 (d, J = 5.6 Hz, 1H), 7.15 (d, J = 5.6 Hz, 1H), 7.36 (s, 1H), 8.08 (br s, 1H) |
| V-1006 | | $^1$H NMR (DMSO, 400 MHz) δ: 1.34 (t, J = 6.9 Hz, 3H), 1.53-1.70 (m, 2H), 1.72-1.89 (m, 2H), 2.42-2.53 (m, 1H), 2.95-3.10 (m, 2H), 3.81 (s, 3H), 4.15-4.30 (m, 4H), 4.32-4.48 (m, 2H), 6.47 (s, 1H), 6.77-6.92 (m, 2H), 6.95-7.27 (m, 4H), 7.92 (br s, 1H) |
| V-1007 | | $^1$H NMR (DMSO, 400 MHz) δ: 1.31 (br t, J = 6.9 Hz, 3H), 1.50-1.65 (m, 4H), 1.67-1.82 (m, 6H), 2.29-2.39 (m, 1H), 2.40-2.60 (m, 4H), 3.05-3.17 (m, 2H), 4.22 (q, J = 6.9 Hz, 2H), 4.30-4.43 (m, 2H), 6.45 (s, 1H), 6.97 (d, J = 5.7 Hz, 1H), 7.17 (d, J = 5.7 Hz, 1H), 7.68 (br s, 1H) |
| V-1008 | | $^1$H NMR (DMSO, 400 MHz) δ: 1.31 (t, J = 6.8 Hz, 3H), 1.50-1.76 (m, 4H), 2.88-3.12 (m, 7H), 3.56-3.72 (m, 4H), 4.18 (q, J = 6.8 Hz, 2H), 4.32-4.41 (m, 2H), 6.48 (s, 1H), 6.77 (t, J = 7.2 Hz, 1H), 6.88 (d, J = 7.2 Hz, 1H), 7.07 (d, J = 5.4 Hz, 1H), 7.19 (t, J = 7.2 Hz, 1H), 7.24 (d, J = 5.4 Hz, 1H) |

TABLE 7-continued

Spectral data for compounds of the general formula V.

| No | Formula | $^1$H NMR DMSO-d6, δ, ppm; LCMS, m/z (M + 1) |
|---|---|---|
| V-1009 | | $^1$H NMR (DMSO, 400 MHz) δ: 1.37 (t, J = 6.9 Hz, 3H), 1.53-1.75 (m, 4H), 1.77-1.88 (m, 2H), 1.89-2.00 (m, 2H), 2.59-2.70 (m, 1H), 2.97-3.12 (m, 2H), 3.30 (t, J = 6.8 Hz, 2H), 3.48 (t, J = 6.8 Hz, 2H), 4.20 (q, J = 6.9 Hz, 2H), 4.37-4.47 (m, 2H), 6.46 (s, 1H), 6.95 (d, J = 5.5 Hz, 1H), 7.13 (d, J = 5.5 Hz, 1H) |
| V-1010 | | $^1$H NMR (DMSO, 400 MHz) δ: 1.62-1.79 (m, 4H), 2.45-2.57 (m, 1H), 2.93-3.10 (m, 2H), 3.82 (s, 3H), 4.30-4.46 (m, 4H), 6.50 (s, 1H), 6.94 (d, J = 6.8 Hz, 1H), 7.13-7.19 (m, 2H), 7.26 (d, J = 8.0 Hz, 1H), 7.63 (t, J = 8.0 Hz, 1H), 8.14 (br s, 1H), 8.45 (d, J = 4.5 Hz, 1H) |
| V-1011 | | $^1$H NMR (DMSO, 400 MHz) δ: 1.58-1.77 (m, 4H), 2.37-2.50 (m, 1H), 2.95-3.12 (m, 2H), 3.84 (s, 3H), 4.25 (d, J = 6.4 Hz, 2H), 4.33-4.45 (m, 2H), 6.14 (br s, 1H), 6.28 (br s, 1H), 6.49 (s, 1H), 6.99 (d, J = 5.7 Hz, 1H), 7.16 (d, J = 5.7 Hz, 1H), 7.41 (br s, 1H), 8.01 (br s, 1H) |
| V-1012 | | $^1$H NMR (DMSO, 400 MHz) δ: 1.57-1.75 (m, 4H), 2.37-2.50 (m, 1H), 2.93-3.10 (m, 2H), 3.74 (s, 3H), 3.81 (s, 3H), 4.18 (d, J = 6.4 Hz, 2H), 4.33-4.45 (m, 2H), 6.48 (s, 1H), 6.77 (d, J = 8.3 Hz, 2H), 6.97 (d, J = 5.7 Hz, 1H), 7.10-7.20 (m, 3H), 7.98 (br s, 1H) |

TABLE 7-continued

Spectral data for compounds of the general formula V.

| No | Formula | $^1$H NMR DMSO-d6, δ, ppm; LCMS, m/z (M + 1) |
|---|---|---|
| V-1013 | | $^1$H NMR (DMSO, 400 MHz) δ: 1.52-1.80 (m, 4H), 2.35-2.45 (m, 1H), 2.92-3.07 (m, 2H), 3.20-3.25 (m, 2H), 3.26 (s, 3H), 3.33 (t, J = 6.6 Hz, 2H), 3.81 (s, 3H), 4.30-4.42 (m, 2H), 6.48 (s, 1H), 6.99 (d, J = 5.4 Hz, 1H), 7.16 (d, J = 5.4 Hz, 1H), 7.65 (br s, 1H) |
| V-1014 | | $^1$H NMR (DMSO, 400 MHz) δ: 1.50-1.67 (m, 2H), 1.69-1.80 (m, 2H), 2.70-2.85 (m, 1H), 2.90-3.20 (m, 4H), 4.12 (t, J = 6.5 Hz, 2H), 4.32-4.46 (m, 2H), 5.38 (s, 2H), 6.52 (s, 1H), 6.91 (t, J = 7.2 Hz, 1H), 6.95-7.03 (m, 3H), 7.06-7.14 (m, 2H), 7.15 (d, J = 5.3 Hz, 1H), 7.18-7.24 (m, 2H), 8.11 (br s, 1H) |
| V-1015 | | $^1$H NMR (DMSO, 400 MHz) δ: 0.98 (t, J = 7.2 Hz, 3H), 1.40-1.64 (m, 4H), 2.22-2.40 (m, 6H), 2.70-2.95 (m, 3H), 3.44-3.51 (m, 4H), 4.23-4.33 (m, 2H), 5.38 (s, 2H), 6.52 (s, 1H), 6.91-7.00 (m, 3H), 7.10-7.13 (m, 3H) |
| V-1016 | | $^1$H NMR (DMSO, 400 MHz) δ: 1.03 (d, J = 6.5 Hz, 6H), 1.38-1.53 (m, 2H), 1.56-1.68 (m, 2H), 2.19-2.33 (m, 1H), 2.77-2.90 (m, 2H), 3.82 (s, J = 6.5 Hz, 1H), 4.23-4.35 (m, 2H), 5.36 (s, 2H), 6.51 (s, 1H), 6.90-7.00 (m, 3H), 7.10-7.28 (m, 4H) |

TABLE 7-continued

Spectral data for compounds of the general formula V.

| No | Formula | ¹H NMR DMSO-d6, δ, ppm; LCMS, m/z (M + 1) |
|---|---|---|
| V-1017 | | ¹H NMR (DMSO, 400 MHz) δ: 1.42-1.68 (m, 4H), 2.19 (s, 3H), 2.24-2.34 (m, 4H), 2.80-3.01 (m, 3H), 3.42-3.54 (m, 4H), 4.25-4.39 (m, 2H), 5.43 (s, 2H), 6.57 (s, 1H), 6.95 (d, J = 5.4 Hz, 1H), 7.11-7.28 (m, 5H) |
| V-1018 | | ¹H NMR (DMSO, 400 MHz) δ: 1.40-1.72 (m, 10H), 2.72-2.83 (m, 1H), 2.90-3.10 (m, 2H), 3.37-3.50 (m, 4H), 4.26-4.40 (m, 2H), 5.43 (s, 2H), 6.57 (s, 1H), 6.95 (d, J = 5.4 Hz, 1H), 7.10-7.29 (m, 5H) |
| V-1019 | | ¹H NMR (DMSO, 400 MHz) δ: 1.45-1.63 (m, 2H), 1.65-1.80 (m, 2H), 2.36-2.45 (m, 1H), 2.80-3.02 (m, 2H), 4.20-4.42 (m, 4H), 5.42 (s, 2H), 6.58 (s, 1H), 6.98 (d, J = 5.4 Hz, 1H), 7.08-7.30 (m, 6H), 7.59 (d, J = 7.2 Hz, 1H), 8.15 (br s, 1H), 8.39 (d, J = 4.1 Hz Гц, 2H), 8.43 (s, 1H) |
| V-1020 | | ¹H NMR (DMSO, 400 MHz) δ: 1.35 (t, J = 6.9 Hz, 3H), 1.54-1.72 (m, 4H), 2.18 (s, 3H), 2.22-2.37 (m, 4H), 2.87-2.93 (m, 1H), 2.97-3.05 (m, 2H), 3.40-3.55 (m, 4H), 4.21 (q, J = 6.9 Hz, 2H), 4.33-4.42 (m, 2H), 6.47 (s, 1H), 6.95 (d, J = 5.4 Hz, 1H), 7.14 (d, J = 5.4 Hz, 1H) |

TABLE 7-continued

Spectral data for compounds of the general formula V.

| No | Formula | $^1$H NMR DMSO-d6, δ, ppm; LCMS, m/z (M + 1) |
|---|---|---|
| V-1021 | | $^1$H NMR (DMSO, 400 MHz) δ: 1.37 (t, J = 6.9 Hz, 3H), 1.50-1.75 (m, 8H), 2.87-2.93 (m, 1H), 2.98-3.10 (m, 2H), 3.45-3.57 (m, 4H), 3.82 (s, 4H), 4.20 (q, J = 6.9 Hz, 2H), 4.34-4.45 (m, 2H), 6.45 (s, 1H), 6.96 (d, J = 5.4 Hz, 1H), 7.15 (d, J = 5.4 Hz, 1H) |
| V-1022 | | $^1$H NMR (DMSO, 400 MHz) δ: 1.60-1.83 (m, 4H), 2.87-2.93 (m, 1H), 3.05-3.15 (m, 6H), 3.60-3.75 (m, 4H), 3.78 (s, 3H), 4.35-4.47 (m, 2H), 6.51 (s, 1H), 6.78 (t, J = 7.3 Hz, 1H), 6.89 (d, J = 7.3 Hz, 2H), 6.99 (d, J = 5.5 Hz, 1H), 7.14-7.22 (m, 3H) |
| V-1023 | | $^1$H NMR (DMSO, 400 MHz) δ: 1.43-1.60 (m, 2H), 1.67-1.78 (m, 2H), 2.40-2.50 (m, 1H), 2.90-3.05 (m, 2H), 4.24-4.40 (m, 4H), 5.36 (s, 2H), 6.51 (s, 1H), 6.90-7.00 (m, 3H), 7.10-7.23 (m, 5H), 7.62 (t, J = 7.5 Hz, 1H), 8.10 (br s, 1H), 8.41 (d, J = 4.3 Hz, 1H) |
| V-1024 | | $^1$H NMR (DMSO, 400 MHz) δ: 1.28-1.40 (m, 2H), 1.41-1.72 (m, 8H), 1.74-1.86 (m, 2H), 2.22-2.33 (m, 1H), 2.80-2.93 (m, 2H), 3.95-4.01 (m, 1H), 4.23-4.33 (m, 4H), 5.39 (s, 2H), 6.51 (s, 1H), 6.94-7.01 (m, 3H), 7.12-7.23 (m, 3H), 7.33 (br s, 1H) |

TABLE 7-continued

Spectral data for compounds of the general formula V.

| No | Formula | ¹H NMR DMSO-d6, δ, ppm; LCMS, m/z (M + 1) |
|---|---|---|
| V-1025 | | ¹H NMR (DMSO, 400 MHz) δ: 1.13 (t, J = 7.1 Hz, 3H), 1.50-1.65 (m, 2H), 1.68-1.82 (m, 2H), 2.49-2.61 (m, 3H), 2.84-2.92 (m, 2H), 4.25-4.40 (m, 2H), 5.42 (s, 2H), 6.52 (s, 1H), 6.96-7.04 (m, 5H), 7.13-7.23 (m, 3H), 7.45 (d, J = 7.5 Hz, 2H), 9.48 (br s, 1H) |
| V-1026 | | ¹H NMR (DMSO, 400 MHz) δ: 1.40-1.75 (m, 4H), 2.25-2.45 (m, 7H), 2.78-3.00 (m, 2H), 3.13-3.35 (m, 2H), 3.50-3.65 (m, 4H), 4.25-4.37 (m, 2H), 5.42 (s, 2H), 6.52 (s, 1H), 6.92-7.03 (m, 3H), 7.14 (d, J = 5.5 Hz, 1H), 7.16-7.23 (m, 2H), 7.26 (br s, 1H) |
| V-1027 | | ¹H NMR (DMSO, 400 MHz) δ: 1.45-1.70 (m, 4H), 1.78-2.00 (m, 4H), 2.57-2.68 (m, 1H), 2.89-3.03 (m, 2H), 3.34 (t, J = 6.5 Hz, 2H), 3.46 (t, J = 6.5 Hz, 2H), 4.30-4.40 (m, 2H), 5.43 (s, 2H), 6.57 (s, 1H), 6.99 (d, J = 5.4 Hz, 1H), 7.14-7.21 (m, 3H), 7.23-7.28 (m, J = 7.8 Hz, 2H) |
| V-1030 | | LCMS m/z 495 (M + 1) |

TABLE 7-continued

Spectral data for compounds of the general formula V.

| No | Formula | ¹H NMR DMSO-d6, δ, ppm; LCMS, m/z (M + 1) |
|---|---|---|
| V-1031 | | LCMS m/z 477 (M + 1) |
| V-1032 | | LCMS m/z 500 (M + 1) |
| V-1033 | | LCMS m/z 490 (M + 1) |
| V-1034 | | LCMS m/z 490 (M + 1) |
| V-1035 | | LCMS m/z 490 (M + 1) |
| V-1036 | | LCMS m/z 444 (M + 1) |

TABLE 7-continued

Spectral data for compounds of the general formula V.

| No | Formula | $^1$H NMR DMSO-d6, δ, ppm; LCMS, m/z (M + 1) |
|---|---|---|
| V-1037 | | LCMS m/z 495 (M + 1) |
| V-1038 | | LCMS m/z 497 (M + 1) |
| V-1039 | | LCMS m/z 472 (M + 1) |
| V-1040 | | LCMS m/z 459 (M + 1) |
| V-1041 | | LCMS m/z 499 (M + 1) |
| V-1042 | | LCMS m/z 497 (M + 1) |

TABLE 7-continued

Spectral data for compounds of the general formula V.

| No | Formula | $^1$H NMR DMSO-d6, δ, ppm; LCMS, m/z (M + 1) |
|---|---|---|
| V-1043 | | LCMS m/z 485 (M + 1) |
| V-1044 | | LCMS m/z 457 (M + 1) |
| V-1045 | | LCMS m/z 494 (M + 1) |
| V-1046 | | LCMS m/z 487 (M + 1) |
| V-1047 | | LCMS m/z 485 (M + 1) |
| V-1048 | | LCMS m/z 469 (M + 1) |

TABLE 7-continued
Spectral data for compounds of the general formula V.
| No | Formula | $^{1}$H NMR DMSO-d6, δ, ppm; LCMS, m/z (M + 1) |
|---|---|---|
| V-1049 | 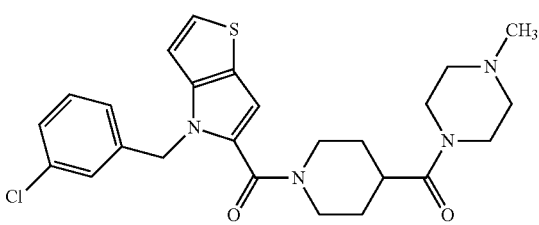 [SMILES: CN1CCN(C(=O)C2CCN(C(=O)c3cc4sccc4n3Cc3cccc(Cl)c3)CC2)CC1] | LCMS m/z 484 (M + 1) |
| V-1050 | 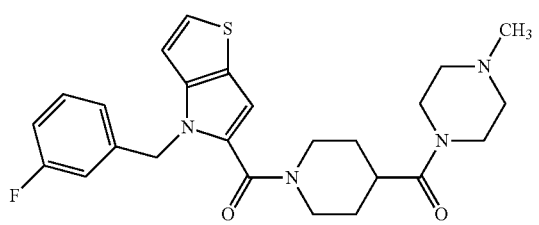 [SMILES: CN1CCN(C(=O)C2CCN(C(=O)c3cc4sccc4n3Cc3cccc(F)c3)CC2)CC1] | LCMS m/z 469 (M + 1) |
| V-1051 | 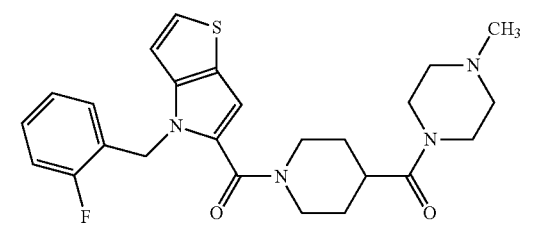 [SMILES: CN1CCN(C(=O)C2CCN(C(=O)c3cc4sccc4n3Cc3ccccc3F)CC2)CC1] | LCMS m/z 469 (M + 1) |
| V-1052 | 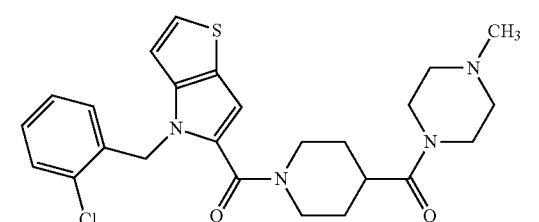 | LCMS m/z 484 (M + 1) |
| V-1053 | 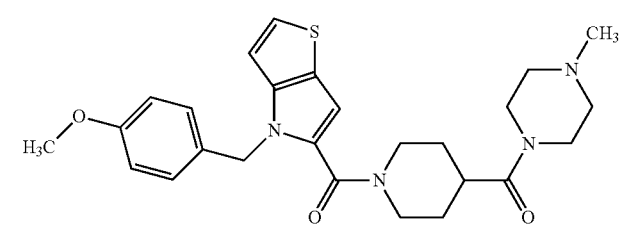 | LCMS m/z 480 (M + 1) |
| V-1054 | 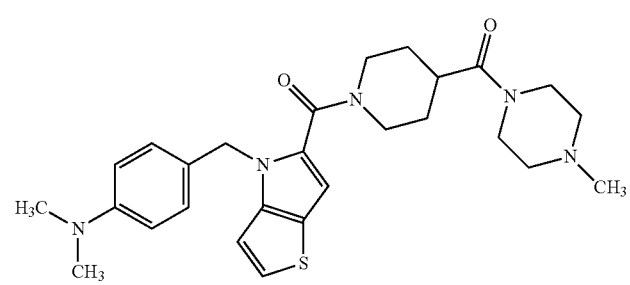 | LCMS m/z 494 (M + 1) |

TABLE 7-continued

Spectral data for compounds of the general formula V.

| No | Formula | $^1$H NMR DMSO-d6, δ, ppm; LCMS, m/z (M + 1) |
|---|---|---|
| V-1055 | | LCMS m/z 495 (M + 1) |
| V-1056 | | LCMS m/z 500 (M + 1) |
| V-1057 | | LCMS m/z 514 (M + 1) |
| V-1058 | | LCMS m/z 528 (M + 1) |
| V-1059 | | LCMS m/z 452 (M + 1) |
| V-1060 | | LCMS m/z 457 (M + 1) |

TABLE 7-continued

Spectral data for compounds of the general formula V.

| No | Formula | ¹H NMR DMSO-d6, δ, ppm; LCMS, m/z (M + 1) |
|---|---|---|
| V-1061 | | LCMS m/z 467 (M + 1) |
| V-1062 | | LCMS m/z 452 (M + 1) |
| V-1063 | | LCMS m/z 520 (M + 1) |
| V-1064 | | LCMS m/z 511 (M + 1) |
| V-1065 | | LCMS m/z 487 (M + 1) |
| V-1066 | | LCMS m/z 451 (M + 1) |

TABLE 7-continued

Spectral data for compounds of the general formula V.

| No | Formula | $^{1}$H NMR DMSO-d6, δ, ppm; LCMS, m/z (M + 1) |
|---|---|---|
| V-1067 | (3,5-dichlorobenzyl thienopyrrole piperidine N-methylpiperazine diamide) | LCMS m/z 520 (M + 1) |
| V-1068 | (4-bromobenzyl thienopyrrole piperidine N-methylpiperazine diamide) | LCMS m/z 530 (M + 1) |
| V-1069 | (4-(2-hydroxyethoxy)benzyl thienopyrrole piperidine N-methylpiperazine diamide) | LCMS m/z 511 (M + 1) |

EXAMPLE 8

Synthesis of Compounds of the General Formula VI (Scheme 6)

Compounds f1. 1,1'-Carbonyldiimidazole (0.11 mol) was added in portions to the solution of 2-chloroisonicotinic acid (0.1 mol) in absolute DMF (50 ml) and the resultant mixture was stirred at 80° C. for 1-2 hours without air access. Then to the reaction mixture cooled to room temperature, the corresponding amine (0.1 mol) was added and stirring was continued at 100° C. for 3 hours without air access. After cooling to room temperature the reaction mixture was poured into 10-fold volume of water, the solid precipitated was filtered off, washed with water and dried in the opened air. Pure amides f1 were obtained by recrystallization from methanol with 45-75% yield.

Compounds f2. Dried $K_2CO_3$ (0.2 mol) was added to the solution of amide f1 (0.1 mol) and isonipecotic ester (0.11 mol) in absolute DMF (100 ml). The reaction mixture was boiled for 4 hours, cooled to room temperature and filtered. Filtrate was evaporated at reduced pressure. The residue was diluted with water (300 ml), the solid precipitated was filtered off, washed with water and dried in the opened air. Pure compounds f2 were obtained by recrystallization from methanol with 65-70% yield.

Compounds of the general formula VI. Compound f2 (0.1 mol) was suspended in solution of NaOH (0.25 mol in 500 ml of water and 10 ml of ethanol). The reaction mixture was stirred at 80° C. until complete dissolution of the solid and after cooling to room temperature it was acidified with acetic acid to pH=5-6. The solid precipitated was filtered off, washed with water and dried in the opened air. After recrystallization from dioxane pure acids were prepared with 75-80% yield. Then 1,1'-carbonyldiimidazole (0.95 mmol) was added to the solution of acid (1 mmol) in dry dioxane (5 ml) and the resultant mixture was stirred at 60° C. for 1 hour in nitrogen atmosphere. Primary or secondary amine (1 mmol) was added, the mixture was boiled for 3-4 hours and left for a night at room temperature. After that it was poured in 3% solution of soda (50 ml) and stirring was continued until solid precipitated. The latter was filtered off, washed twice with water and dried in the opened air. If required, the product was recrystallized from the proper solvent. The oily products were extracted with methylene chloride, combined extracts were washed twice with water, dried over $MgSO_4$ and evaporated at reduced pressure. The crude product was purified either by recrystallization from isopropanol or by flash chromatography on silica gel. The yield of amides of the general formula VI was 40-85%, some of them are presented in Table 8.

TABLE 8

Spectral data for compounds of the general formula VI.

| № | Formula | $^1$H NMR, DMSO-d6, δ, ppm; LCMS, m/z (M + 1) |
|---|---------|------------------------------------------------|
| VI-1001 | | $^1$H NMR (DMSO, 400 MHz) δ: 1.34 (t, J = 6.7 Hz, 3H), 1.50-1.71 m, 6H), 2.30-2.45 (m, 1H), 2.52-2.60 (m, 2H), 2.81-2.96 (m, 2H), 3.00-3.10 (m, 2H), 4.01(q, J = 6.7 Hz, 2H), 4.33-4.48 (m, 2H), 6.88 (d, J = 8.8 Hz, 2H), 7.01 (d, J = 4.8 Hz, 1H), 7.11-7.30 (m, 6H), 7.60 (d, J = 8.8 Hz, 2H), 7.56 (br s, J = 6.0 Hz, 1H), 8.18 (d, J = 4.8 Hz, 1H), 10.07 (s, 1H); LCMS m/z 487 (M + 1); M.p. 203-205° C. |
| VI-1002 | | $^1$H NMR (DMSO, 400 MHz) δ: 1.36 (t, J = 6.8 Hz, 3H), 1.60-1.75 (m, 2H), 1.80-1.92 (m, 2H), 2.17(s, 3H), 2.20 (s, 3H), 2.54-2.66 (m, 1H), 2.87-2.99 (m, 2H), 4.03 (q, J = 6.8 Hz, 2H), 4.48-4.51 (m, 2H), 6.86 (d, J = 8.8 Hz, 2H), 6.95-7.06 (m, 2H), 7.23 (s, 1H), 7.28 (d, (d, J = 8.8 Hz, 2H),8.21 (d, J = 4.8 Hz, 1H), 9.64(s, 1H), 10.09 (s, 1H); LCMS m/z 473 (M + 1); M.p. 235-237° C. |
| VI-1003 | | $^1$H RMP (πMCO, 400 Mτμ) δ 1.37 (t, J = 6.8 Hz, 3H), 1.60-1.75 (m, 2H), 1.80-1.92 (m, 2H), 2.23 (s, 6H), 2.54-2.66 (m, 1H), 2.85-3.00 (m, 2H), 4.02 (q, J = 6.8 Hz, 2H), 4.40-4.50 (m, 2H), 6.64 (s, 1H), 6.87 (d, J = 8.7 Hz, 2H), 7.15 (d, J = 4.8 Hz, 1H), 7.16-7.26 (m, 3H), 7.62 (d, J = 8.7 Hz, 2H), 8.21 (d, J = 4.8 Hz, 1H), 9.65 (s, 1H), 10.09 (s, 1H); LCMS m/z 473 (M + 1); M.p. 250-252° C. |
| VI-1004 | | LCMS m/z 491 (M + 1); M.p. 200-202° C. |

TABLE 8-continued

Spectral data for compounds of the general formula VI.

| N° | Formula | ¹H NMR, DMSO-d6, δ, ppm; LCMS, m/z (M + 1) |
|---|---|---|
| VI-1005 | | LCMS m/z 487 (M + 1); M.p. 243-245° C. |
| VI-1006 | | ¹H NMR (DMSO, 400 MHz) δ: 1.36 (t, J = 6.8 Hz, 3H), 1.58-1.73 (m, 2H), 1.80-1.95 (m, 2H), 2.76-3.00 (m, 3H), 3.84 (s, 3H), 4.00 (q, J = 6.8 Hz, 2H), 4.37-4.51 (m, 2H), 6.82-6.92 (m, 3H), 6.94-7.10 (m, 3H), 7.21(s, 1H), 7.62 (d, J = 8.7 Hz, 2H). 7.9S (d, J = 7.9 Hz, 1H), 8.22 (d, J = 4.7 Hz. 1H), 8.94 (s, 1H), 10.08 (s, 1H); LCMS m/z 475 (M + 1); M.p. 182-184° C. |
| VI-1007 | | ¹H NMR (DMSO, 300 MHz) δ: 1.32 (t, J = 6.7 Hz, 3H), 1.55-1.74 (m, 2H), 1.83-1.94 (m, 2H), 2.07-2.20 (m, 1H), 2.88-3.03 (m, 2H), 4.03 (q, J = 6.7 Hz, 2H), 4.38-4.50 (m, 2H), 6.92 (d, J = 8.8 Hz, 2H), 7.02-7.15 (m, 3H), 7.25 (s, 1H), 7.58-7.67 (m, 4H), 8.24 (d, J = 4.8 Hz, 1H), 9.95 (s, 1H), 10.13 (s, 1H) |
| VI-1008 | | ¹H NMR (DMSO, 300 MHz) δ: 1.32 (t, J = 6.7 Hz, 3H), 1.50-1.78 (m,4H), 2.85-3.07 (m, 3H), 3.37-3.68 (m, 8H), 4.03 (q, J = 6.7 Hz, 2H). 4.31-4.45 (m, 2H), 6.93 (d, J = 8.8 Hz, 2H), 7.03 (d, J = 4.8 Hz, 1H), 7.22 (s, 1H), 7.63 (d, J = 8.8 Hz, 2H), 8.22 (d, J = 4.8 Hz, 1H), 10.11 (s, 1H) |

TABLE 8-continued
Spectral data for compounds of the general formula VI.
| Nº | Formula | ¹H NMR, DMSO-d6, δ, ppm; LCMS, m/z (M + 1) |
|---|---|---|
| VI-1009 | 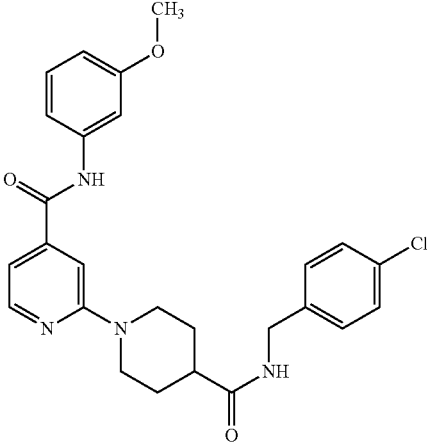 [SMILES: COc1cccc(NC(=O)c2ccnc(N3CCC(C(=O)NCc4ccc(Cl)cc4)CC3)c2)c1] | ¹H NMR (DMSO, 500 MHz) δ: 1.52-1.65 (m, 2H), 1.76-1.83 (m, 2H), 2.40-2.50 (m, 1H), 2.85-2.96 (m, 2H), 3.76 (s, 3H), 4.24 (d, J = 6.3 Hz, 2H), 4.35-4.44 (m, 2H), 6.72 (d, J = 8.6 Hz, 1H), 7.04 (d, J = 4.8 Hz, 1H), 7.22-7.28 (m, 4H), 7.32-7.39 (m, 3H), 7.44 (s, 1H), 8.24 (d, J = 4.8Hz, 1H), 8.43 (br t, J = 6.6 Hz, 1H), 10.28 (br s, 1H) |
| VI-1010 | 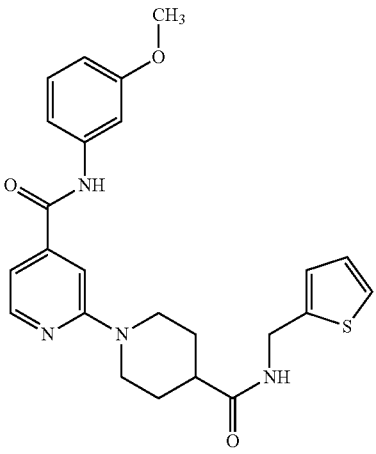 [SMILES: COc1cccc(NC(=O)c2ccnc(N3CCC(C(=O)NCc4cccs4)CC3)c2)c1] | ¹H NMR (DMSO, 500 MHz) δ: 1.52-1.65 (m, 2H), 1.72-1.80 (m, 2H), 2.40-2.50 (m, 1H), 2.85-2.96 (m, 2H), 3.76 (s, 3H), 4.36-4.47 (m, 4H), 6.71 (d, J = 8.6 Hz, 1H), 6.91-6.96 (m, 2H), 7.02 (d, J = 4.8 Hz, 1H), 7.21-7.28 (m, 2H), 7.32-7.38 (m, 2H), 7.45 (s, 1H), 8.24 (d, J = 4.8 Hz, 1H), 8.50 (br s, J = 6.6 Hz, 1H), 10.30 (br s, 1H) |
| VI-1011 | 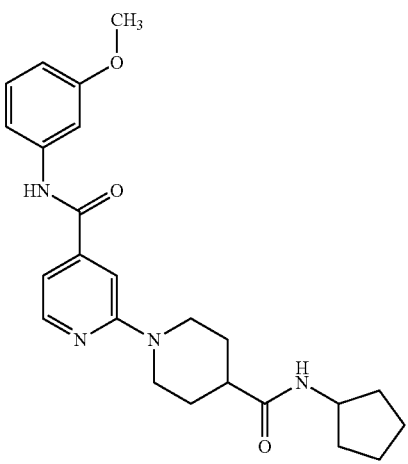 [SMILES: COc1cccc(NC(=O)c2ccnc(N3CCC(C(=O)NC4CCCC4)CC3)c2)c1] | ¹H NMR (DMSO, 500 MHz) δ: 1.30-1.80 (m, 12H), 2.32-2.40 (m, 1H), 2.82-2.92 (m, 2H), 3.74 (s, 3H), 3.92-4.00 (m, 1H), 4.35-4.45 (m, 2H), 6.72 (d, J = 8.6 Hz, 1H), 7.02 (d, J = 4.8 Hz, 1H), 7.22 (s, 1H), 7.27 (t, J = 8.6 Hz, 1H), 7.32-7.35 (m, 1H), 7.43 (s, 1H), 7.78 (d, J = 7.1 Hz, 1H), 8.23 (d, J = 4.8 Hz, 1H), 10.30 (s, 1H) |

TABLE 8-continued

Spectral data for compounds of the general formula VI.

| № | Formula | $^1$H NMR, DMSO-d6, δ, ppm; LCMS, m/z (M + 1) |
|---|---------|------------------------------------------------|
| VI-1012 | | $^1$H NMR (DMSO, 300 MHz) δ: 1.43-1.64 (m, 2H), 1.65-1.78 (m, 2H), 2.25-2.45 (m, 1H), 2.65-2.77 (m, 2H), 2.86-3.06 (m, 2H), 3.20-3.34 (m, 2H), 3.74 (s, 3H), 4.25-4.44 (m, 2H), 6.71 (d, J = 8.6 Hz, 1H), 7.06 (d, J = 4.8 Hz, 1H), 7.12-7.38 (m, 8H), 7.43 (s, 1H), 7.93 (t, J = 6.6 Hz, 1H), 8.24 (d, J = 4.8 Hz, 1H), 8.43 (br s, J = 6.0 Hz, 1H), 10.28 (br s, 1H) |
| VI-1013 | | LCMS m/z 461 (M + 1) |
| VI-1014 | | LCMS m/z 463 (M + 1) |
| VI-1015 | | LCMS m/z 427 (M + 1) |
| VI-1016 | | LCMS m/z 452 (M + 1); |

TABLE 8-continued

Spectral data for compounds of the general formula VI.

| № | Formula | $^1$H NMR, DMSO-d6, δ, ppm; LCMS, m/z (M + 1) |
|---|---|---|
| VI-1017 | | LCMS m/z 423 (M + 1) |
| VI-1018 | | LCMS m/z 407 (M + 1) |
| VI-1019 | | LCMS m/z 423 (M + 1) |
| VI-1020 | | LCMS m/z 409 (M + 1) |
| VI-1021 | | LCMS m/z 393 (M + 1) |

TABLE 8-continued

Spectral data for compounds of the general formula VI.

| № | Formula | ¹H NMR, DMSO-d6, δ, ppm; LCMS, m/z (M + 1) |
|---|---------|---------------------------------------------|
| VI-1022 | | LCMS m/z 486 (M + 1) |
| VI-1023 | | LCMS m/z 451 (M + 1) |
| VI-1024 | | LCMS m/z 475 (M + 1) |
| VI-1025 | | LCMS m/z 459 (M + 1) |

TABLE 8-continued

Spectral data for compounds of the general formula VI.

| № | Formula | $^1$H NMR, DMSO-d6, δ, ppm; LCMS, m/z (M + 1) |
|---|---------|-----------------------------------------------|
| VI-1026 | | LCMS m/z 489 (M + 1) |

EXAMPLE 9

Synthesis of Compounds of the General Formula VII (Scheme 7)

Compounds g1. Mixture of 6-methyltetrahydroquinoline (0.5 mol), sulfonyl chloride (0.55 mol) and triethylamine (0.6 mol) in methylene chloride (200 ml) was boiled at stirring until the reaction was completed. Monitoring of the reaction was conducted by TLC (CHCl$_3$:CH$_3$OH, 4:1). After cooling to room temperature the solvent was evaporated at reduced pressure, the residue was diluted with water (1000 ml). The solid obtained was filtered off, washed with water and dried in the opened air. The yield of compounds g1 was 78-85%.

Compounds g2. KMnO$_4$ (1.32 mol) was added in small portions to the suspension of compound g1 (0.5 mol) in water at vigorous stirring. The mixture was boiled at stirring until the volume of the reaction mixture diminished to 250 ml, cooled to 0° C. and carefully acidified with conc. HCl (150 ml). After that the reaction mixture was warmed to boiling and left for a night at room temperature. The solid obtained was filtered off, washed with water and dried in the opened air. The yield of acids g2 was 55-62%.

Compounds of the general formula VII. 1,1'-Carbonyldiimidazole (1.15 mmol) was added to the solution of acid 4 (1 mmol) in absolute DMF (5 ml) and the resultant mixture was stirred at 80° C. for 1 hour in nitrogen atmosphere. Then primary or secondary amine (1.4 mmol) was added and stirring was continued at the same temperature for additional 6 hours. After cooling to room temperature the reaction mixture was poured into 3% solution of soda (50 ml) and stirred until solid precipitated. The latter was filtered off, washed twice with water and dried in the opened air. If required, the product was recrystallized from the proper solvent. The oily products were extracted with methylene chloride, combined extracts were washed twice with water, dried over MgSO4 and evaporated at reduced pressure. The crude product was purified either by recrystallization from the proper solvent or by flash chromatography on silica gel. The yield of amides of the general formula VII was 20-85%, some of them are presented in Table 9.

TABLE 9

Spectral data for compounds of the general formula VII.

| № | Formula | $^1$H NMR, DMSO-d6, δ, ppm; LCMS, m/z (M + 1) |
|---|---------|-----------------------------------------------|
| VII-1001 | 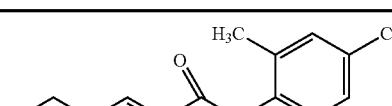 | $^1$H NMR (DMSO, 300 MHz) δ: 1.66 (br s, 2H), 2.12 (s, 6H), 2.26 (s, 3H), 2.48 (s, 3H), 2.60 (br t, 2H), 3.81 (br t, 2H), 6.88 (s, 1H), 7.36 (d, J = 8.0 Hz, 2H), 7.57 (d, J = 8.0 Hz, 2H), 7.66-7.82 (m, 3H), 9.52 (br s, 1H); LCMS m/z 449 (M + 1); M.p. 252-255° C. |

TABLE 9-continued

Spectral data for compounds of the general formula VII.

| № | Formula | $^1$H NMR, DMSO-d6, δ, ppm; LCMS, m/z (M + 1) |
|---|---|---|
| VII-1002 | | 1H NMR (DMSO, 300 MHz) δ: 1.94 (q, J = 5.8 Hz, 2H), 2.75 (d, J = 3.5 Hz, 3H), 2.85 (t, J = 5.8 Hz, 2H), 3.06 (s, 3H), 3.71 (t, J = 5.8 Hz, 2H), 7.56-7.68 (m, 3H), 8.23 (br s, 1H) |
| VII-1003 | | 1H NMR (DMSO, 300 MHz) δ: 1.94 (q, J = 5.7 Hz, 2H), 2.83 (t, J = 5.7 Hz, 2H), 3.07 (s, 3H), 3.65-3.83 (m, 5H), 4.38 (d, J = 5.5 Hz, 2H), 6.87 (d, J = 8.8 Hz, 2H), 7.23 (d, J = 8.8 Hz, 2H), 7.56-7.75 (m, 3H), 8.74 (br s, 1H) |
| VII-1004 | | $^1$H NMR (DMSO, 300 MHz) δ: 1.94 (q, J = 5.8 Hz, 2H), 2.85 (t, J = 5.8 Hz, 2H), 3.09 (s, 3H), 3.72 (t, J = 5.8 Hz, 2H), 4.58 (d, J = 5.6 Hz, 2H), 7.16-7.34 (m, 2H), 7.58-7.80 (m, 4H), 8.50 (d, J = 6.3 Hz, 1H), 8.94 (br s, 1H) |
| VII-1005 | | $^1$H NMR (DMSO, 400 MHz) δ: 1.96 (q, J = 5.7 Hz, 2H), 2.87 (t, J = 5.7 Hz, 2H), 3.10 (s, 3H), 3.73 (t, J = 5.7 Hz, 2H), 5.99 (s, 2H), 6.88 (d, J = 8.3 Hz, 1H), 7.33 (dd, J = 8.3 Hz, J = 2.1 Hz, 1H), 7.43 (s, 1H), 7.63-7.79 (m, 3H), 10.05 (br s, 1H) |
| VII-1006 | | $^1$H NMR (DMSO, 300 MHz) δ: 2.02 (q, J = 5.7 Hz, 2H), 2.88 (t, J = 5.7 Hz, 2H), 3.00 (s, 3H), 3.40-3.71 (m, 8H), 3.78 (t, J = 5.7 Hz, 2H), 7.12-7.21 (m, 2H), 7.62-7.68 (m, 1H) |
| VII-1007 | | $^1$H NMR (DMSO, 300 MHz) δ: 1.96 (q, J = 5.7 Hz, 2H), 2.85 (t, J = 5.7 Hz, 2H), 3.00-3.16 (m, 7H), 3.40-3.78 (m, 6H), 6.90-7.08 (m, 4H), 7.18-7.26 (m, 2H), 7.62 (d, J = 8.8 Hz, 1H) |

TABLE 9-continued

Spectral data for compounds of the general formula VII.

| Nº | Formula | $^1$H NMR, DMSO-d6, δ, ppm; LCMS, m/z (M + 1) |
|---|---|---|
| VII-1008 | | $^1$H NMR (DMSO, 300 MHz) δ: 1.16 (t, J = 6.9 Hz, 3H), 1.65 (q, J = 5.8 Hz, 2H), 2.53(t, J = 5.8 Hz, 2H), 3.30 (q, J = 6.9 Hz, 2H), 3.80 (t, J = 5.8 Hz, 2H), 3.71 (t, J = 5.8 Hz, 2H), 7.44-7.76 (m, 8H), 8.14 (br t, J = 6.0 Hz, 1H) |
| VII-1009 | | $^1$H NMR (DMSO, 300 MHz) δ: 1.66 (q, J = 5.7 Hz, 2H), 2.32 (s, 3H), 2.56 (t, J = 5.7 Hz, 2H), 3.82 (t, J = 5.7 Hz, 2H), 4.42 (d, J = 5.5 Hz, 2H), 7.08 (d, J = 8.4 Hz, 2H), 7.19 (d, J = 8.4 Hz, 2H), 7.45-7.54 (m, 2H), 7.56-7.66 (m, 4H), 7.68-7.77 (m, 2H), 8.68 (br t, J = 5.5 Hz, 1H) |
| VII-1010 | | $^1$H NMR (DMSO, 300 MHz) δ: 1.67 (q, J = 5.7 Hz, 2H), 2.54 (t, J = 5.7 Hz, 2H), 2.77 (t, J = 5.8 Hz, 2H), 3.47 (q, J = 5.8 Hz, 2H), 3.77 (s, 6H), 3.80 (t, J = 5.7 Hz, 2H), 6.68-6.79 (m, 3H), 7.46-7.55 (m, 3H), 7.57-7.67 (m, 4H), 7.72 (d, J = 7.6 Hz, 1H), 8.24 (br t, J = 5.8 Hz, 1H) |
| VII-1011 | | $^1$H NMR (DMSO, 300 MHz) δ: 1.67 (q, J = 5.8 Hz, 2H), 2.53 (t, J = 5.8 Hz, 2H), 3.82 (t, J = 5.8 Hz, 2H), 4.48 (d, J = 5.5 Hz, 2H), 7.22-7.28 (m, 1H), 7.45-7.53 (m, 2H), 7.55-7.66 (m, 4H), 7.68-7.80 (m, 3H), 8.40 (d, J = 4.7 Hz, 1H), 8.52 (s, 1H), 8.82 (br t, J = 5.5 Hz, 1H) |

TABLE 9-continued

Spectral data for compounds of the general formula VII.

| № | Formula | ¹H NMR, DMSO-d6, δ, ppm; LCMS, m/z (M + 1) |
|---|---|---|
| VII-1012 | | ¹H NMR (DMSO, 300 MHz) δ: 1.66 (q, J = 5.8 Hz, 2H), 2.60 (t, J = 5.8 Hz, 2H), 3.84 (t, J = 5.8 Hz, 2H), 7.12 (t, J = 8.3 Hz, 2H), 7.51-7.60 (m, 2H), 7.62-7.70 (m, 4H), 7.71-7.81 (m, 4H), 10.30 (br s, 1H) |
| VII-1013 | | ¹H NMR (DMSO, 300 MHz) δ: 1.68 (q, J = 5.8 Hz, 2H), 1.80-2.05 (m, 4H), 2.52 (t, J = 5.8 Hz, 2H), 3.40-3.58 (m, 4H), 3.81 (t, J = 5.8 Hz, 2H), 7.19 (s, 1H), 7.28 (d, J = 8.3 Hz, 2H), 7.46-7.54 (m, 2H), 7.55-7.67 (m, 3H), 7.72 (d, J = 8.3 Hz, 1H) |
| VII-1014 | | ¹H NMR (DMSO, 300 MHz) δ: 1.66 (q, J = 5.7 Hz, 2H), 2.38 (s, 3H), 2.59 (t, J = 5.7 Hz, 2H), 3.77 (s, 3H), 3.82 (t, J = 5.7 Hz, 2H), 6.88 (d, J = 8.6 Hz, 2H), 7.35 (d, J = 8.6 Hz, 2H), 7.55 (d, J = 8.6 Hz, 2H), 7.58-7.68 (m, 3H), 7.70-7.77 (m, 2H), 9.97 (br s, 1H) |
| VII-1015 | | ¹H NMR (DMSO, 300 MHz) δ: 1.13 (t, J = 6.8 Hz, 3H), 1.62 (q, J = 5.8 Hz, 2H), 2.55 (t, J = 5.8 Hz, 2H), 3.27 (q, J = 6.8 Hz, 2H), 3.81 (t, J = 5.8 Hz, 2H), 7.56-7.71 (m, 7H), 8.41 (br t, 1H) |

TABLE 9-continued

Spectral data for compounds of the general formula VII.

| № | Formula | ¹H NMR, DMSO-d6, δ, ppm; LCMS, m/z (M + 1) |
|---|---|---|
| VII-1016 | | ¹H NMR (DMSO, 300 MHz) δ: 1.65 (q, J = 5.8 Hz, 2H), 2.55 (t, J = 5.8 Hz, 2H), 3.82 (t, J = 5.8 Hz, 2H), 4.43 (d, J = 5.5 Hz, 2H), 6.23 (br s, 1H), 6.36 (br s, 1H), 7.51 (s, 1H), 7.55-7.70 (m, 7H), 8.65 (br t, J = 5.5 Hz, 1H) |
| VII-1017 | | ¹H NMR (DMSO, 300 MHz) δ: 1.68 (q J = 5.7 Hz, 2H), 2.20 (s 3H), 2.22 (s, 3H), 2.60 (t, J = 5.7 Hz, 2H), 3.83 (t, J = 5.7 Hz, 2H), 7.05 (d, J = 8.3 Hz, 1H), 7.40-7.52 (m, 2H), 7.56-7.80 (m, 7H), 9.93 (br s, 1H) |
| VII-1018 | | ¹H NMR (DMSO, 300 MHz) δ: 1.40-1.72 (m, 8H), 2.58 (t, J = 5.8 Hz, 2H), 3.25-3.60 (m, 4H), 3.80 (t, J = 5.8 Hz, 2H), 7.08 (s, 1H), 7.16 (d, J = 8.2 Hz, 2H), 7.54-7.70 (m, 5H) |
| VII-1019 | | ¹H NMR (DMSO, 300 MHz) δ: 1.65 (q, J = 5.6 Hz, 2H), 2.30-2.45 (m, 6H), 2.56 (t, J = 5.6 Hz, 2H), 3.30-3.42 (m, 2H), 3.50-3.62 (m, 4H), 3.70 (t, J = 5.6 Hz, 2H), 7.52-7.70 (m, 7H), 8.27 (br s, 1H) |

TABLE 9-continued

Spectral data for compounds of the general formula VII.

| № | Formula | $^1$H NMR, DMSO-d6, δ, ppm; LCMS, m/z (M + 1) |
|---|---|---|
| VII-1020 | 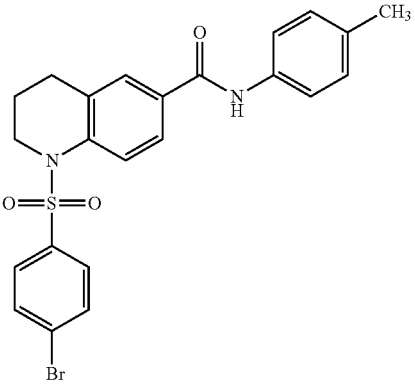 [SMILES: Cc1ccc(NC(=O)c2ccc3c(c2)CCCN3S(=O)(=O)c2ccc(Br)cc2)cc1] | $^1$H NMR (DMSO, 300 MHz) δ: 1.68 (q, J = 5.7 Hz, 2H), 2.28 (s, 3H), 2.59 (t, J = 5.7 Hz, 2H), 3.82 (t, J = 5.7 Hz, 2H), 7.14 (d, J = 8.3 Hz, 2H), 7.55-7.67 (m, 4H), 7.68-7.85 (m, 5H), 10.06 (br s, 1H) |
| VII-1021 | 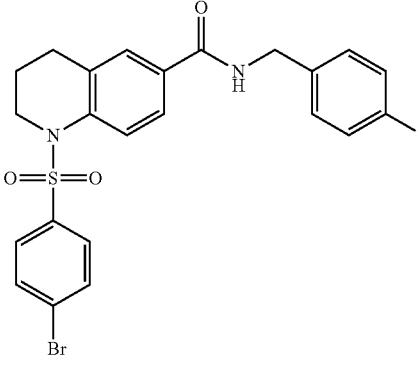 | $^1$H NMR (DMSO, 300 MHz) δ: 1.66 (q, J = 5.7 Hz, 2H), 2.28 (s, 3H), 2.55 (t, J = 5.7 Hz, 2H), 3.82 (t, J = 5.7 Hz, 2H), 4.40 (d, J = 6.0 Hz, 2H), 7.11 (d, J = 7.7 Hz, 2H), 7.19 (d, J = 7.7 Hz, 2H), 7.54-7.73 (m, 5H), 7.73-7.82 (m, 2H), 8.87 (br t, J = 6.0 Hz, 1H) |
| VII-1022 | 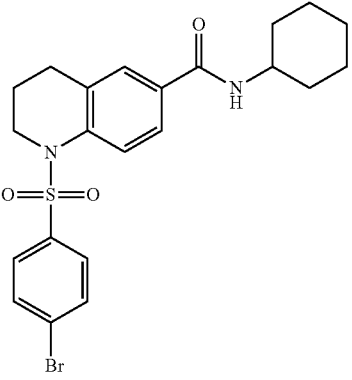 [SMILES: O=C(NC1CCCCC1)c1ccc2c(c1)CCCN2S(=O)(=O)c1ccc(Br)cc1] | 1H NMR (DMSO, 300 MHz) δ: 0.95-1.40 (m, 5H), 1.45-1.96 (m, 7H), 2.54 (t, J = 5.6 Hz, 2H), 3.14-3.33 (m, 1H), 3.60-3.87 (m, 3H), 7.48-7.61 (m, 3H), 7.65 (s, 2H), 7.70-7.81 (m, 2H), 8.20 (br d, J = 6.4 Hz, 1H) |
| VII-1023 | 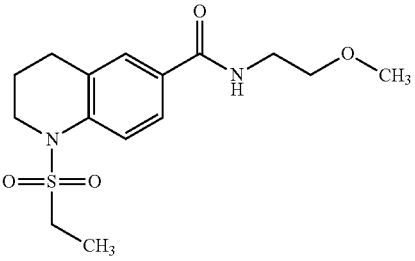 [SMILES: CCS(=O)(=O)N1CCCc2cc(C(=O)NCCOC)ccc21] | $^1$H NMR (DMSO, 300 MHz) δ: 1.30 (t, J = 6.4 Hz, 3H), 2.01 (q, J = 5.6 Hz, 2H), 2.88 (t, J = 5.6 Hz, 2H), 3.28 (q, J = 6.4 Hz, 2H), 3.33 (s, 3H), 3.38-3.51 (m, 4H), 3.77 (t, J = 5.6 Hz, 2H), 7.52-7.68 (m, 3H), 8.18 (br t, 1H) |

TABLE 9-continued

Spectral data for compounds of the general formula VII.

| № | Formula | $^1$H NMR, DMSO-d6, δ, ppm; LCMS, m/z (M + 1) |
|---|---|---|
| VII-1024 | | $^1$H NMR (DMSO, 300 MHz) δ: 1.38 (t, J = 6.2 Hz, 3H), 2.00 (q, J = 5.6 Hz, 2H), 2.90 (t, J = 5.6 Hz, 2H), 3.19 (q, J = 6.2 Hz, 2H), 3.78 (t, J = 5.6 Hz, 2H), 4.48 (d, J = 5.7 Hz, 2H), 7.22-7.28 (m, 1H), 7.55-7.72 (m, 4H), 8.40 (d, J = 4.2 Hz, 1H), 8.52 (s, 1H), 8.79 (br t, 1H) |
| VII-1025 | | $^1$H NMR (DMSO, 300 MHz) δ: 1.30 (t, J = 6.2 Hz, 3H), 2.04 (q, J = 5.6 Hz, 2H), 2.94 (t, J = 5.6 Hz, 2H), 3.25 (q, J = 6.2 Hz, 2H), 3.80 (t, J = 5.6 Hz, 2H), 7.08-7.22 (m, 3H), 7.67 (d, J = 8.0 Hz, 1H), 7.71-7.84 (m, 3H), 9.68 (br s, 1H) |
| VII-1026 | | $^1$H NMR (DMSO, 300 MHz) δ: 1.30 (t, J = 6.3 Hz, 3H), 2.01 (q, J = 5.7 Hz, 2H), 2.88 (t, J = 5.7 Hz, 2H), 3.20 (q, J = 6.3 Hz, 2H), 3.35-3.70 (m, 8H), 3.77 (t, J = 5.7 Hz, 2H), 7.07-7.21 (m, 2H), 7.54 (d, J = 8.0 Hz, 1H) |

EXAMPLE 10

Synthesis of Compounds of the General Formula VIII (Scheme 8)

Compounds h2. The solution of morpholine (5 ml) and diethylamine (3 ml) in ethanol (10 ml) was added to the previously heated to 50° C. mixture of N-substituted piperidin-4-one (0.1 mol), nitrile h1 (0.1 mol) and sulfur (0.1 mol) in ethanol (100 ml) and heating at 60° C. was continued until complete dissolution of the solid. After cooling to 5° C., the reaction mixture was poured into icy water (200 ml) and acidified with 10% solution of HCl. The solid precipitated was filtered off, washed with water, heptane, dried in the opened air and recrystallized from ethanol. The yield of product h2 was 70-75%.

Compounds of the general formula VIII. Carboxylic acid (1.1 mmol) was added to the solution of 1,1'-carbonyldiimidazole (1.2 mmol) in absolute DMF (5 ml). The reaction mixture was stirred at 80° C. for 1 hour without air access. Then amine h2 (1 mmol) was added, the reaction mixture was stirred at 100° C. for additional 3-4 hours and left for a night at room temperature. After that it was poured into 10-fold volume of water, the solid precipitated was filtered off, washed with water and dried in the opened air. Pure compounds of the general formula VIII were prepared by recrystallization from propanol with 40-85% yield. Some of them are presented in Table 10.

TABLE 10

Spectral data for compounds of the general formula VIII.

| № | Formula | $^1$H NMR, DMSO-d6, δ, ppm; LCMS, m/z (M + 1) |
|---|---|---|
| VIII-1001 | 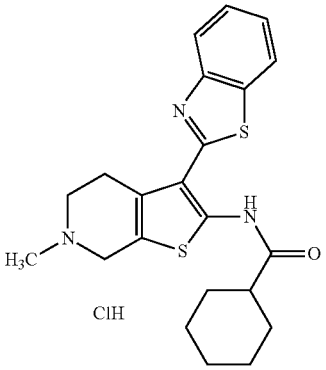 [SMILES: CN1CCc2c(sc(NC(=O)C3CCCCC3)c2-c2nc3ccccc3s2)C1 ; Cl] | $^1$H NMR (DMSO, 400 MHz) δ: 1.15-1.90 (m, 8H), 1.95-2.12 (m, 2H), 2.50-2.63 (m, 1H), 2.90 (s, 3H), 3.12-3.30 (m, 2H), 3.47-3.80 (m, 2H), 4.10-4.57 (m, 2H), 7.49 (t, J = 8.2 Hz, 1H), 7.61 (t, J = 8.2 Hz, 1H), 8.01 (d, J = 8.2 Hz, 1H), 8.19 (d, J = 8.2 Hz, 1H), 11.40 (br s, 1H), 12.90 (s, 1H); LCMS m/z 412 (M + 1) |
| VIII-1002 | 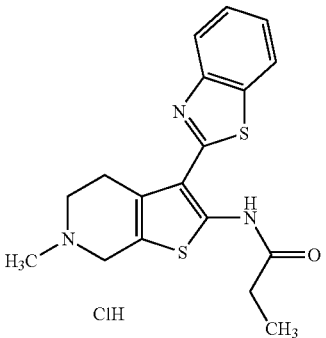 [SMILES: CCC(=O)Nc1sc2c(c1-c1nc3ccccc3s1)CCN(C)C2 ; Cl] | $^1$H NMR (DMSO, 400 MHz) δ: 1.26 (t, J = 6.8 Hz, 3H), 2.66 (q, J = 6.8 Hz, 2H), 2.90 (s, 3H), 3.20-3.32 (m, 2H), 3.50-3.66 (m, 2H), 4.35-4.50 (m, 2H), 7.49 (t, J = 7.9 Hz, 1H), 7.60 (t, J = 7.9 Hz, 1H), 8.10 (d, J = 7.9 Hz, 1H), 8.19 (d, J = 7.9 Hz, 1H), 11.38 (br s, 1H), 12.72 (s, 1H) |
| VIII-1003 | 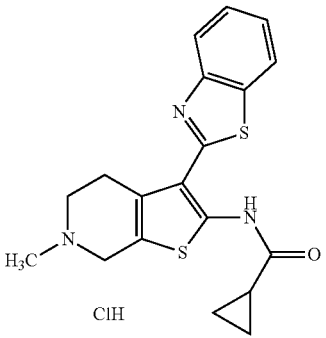 [SMILES: CN1CCc2c(sc(NC(=O)C3CC3)c2-c2nc3ccccc3s2)C1 ; Cl] | $^1$H NMR (TFAA, 400 MHz) δ: 0.99-1.18 (m, 4H), 1.57-1.70 (m, 1H), 3.02-3.33 (m, 5H), 3.43-3.56 (m, 1H), 3.86-3.97 (m, 1H), 4.33 (d, J = 13 Hz, 1H), 4.72 (d, J = 13 Hz, 1H), 7.79 (t, J = 7.9 Hz, 1H), 7.86 (t, J = 7.9 Hz, 1H), 8.08 (d, J = 7.9 Hz, 1H), 8.12 (d, J = 7.9 Hz, 1H) |
| VIII-1004 | 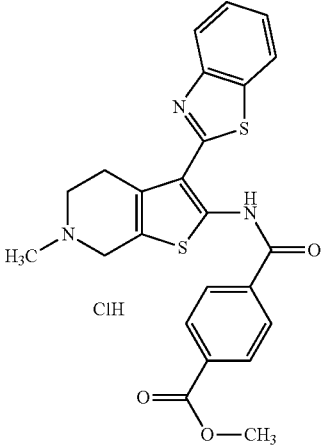 [SMILES: COC(=O)c1ccc(C(=O)Nc2sc3c(c2-c2nc4ccccc4s2)CCN(C)C3)cc1 ; Cl] | $^1$H NMR (TFAA, 400 MHz) δ: 3.20-3.46 (m, 4H), 3.55-3.77 (m, 2H), 4.02-4.25 (m, 4H), 4.56 (d, J = 15 Hz, 1H), 4.96 (d, J = 15 Hz, 1H), 7.85-8.16 (m, 4H), 8.22-8.33 (m, 4H) |

TABLE 10-continued
Spectral data for compounds of the general formula VIII.
| Nº | Formula | $^1$H NMR, DMSO-d6, δ, ppm; LCMS, m/z (M + 1) |
|---|---|---|
| VIII-1005 | 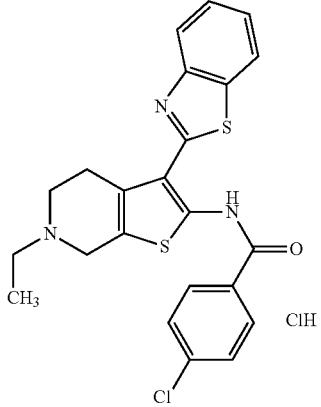 [SMILES: CCN1CCc2c(sc(NC(=O)c3ccc(Cl)cc3)c2-c2nc3ccccc3s2)C1 ; Cl] | $^1$H NMR (TFAA, 400 MHz) δ: 1.54 (t, J = 6.9 Hz, 3H), 3.11-3.22 (m, 1H), 3.28-3.44 (m, 1H), 3.45-3.66 (m, 3H), 3.91-4.05 (m, 1H), 4.41 (d, J = 15 Hz, 1H), 4.83 (d, J = 15 Hz, 1H), 7.43 (d, J = 8.2 Hz, 2H), 7.73 (d, J = 8.2 Hz, 2H), 7.81 (t, J = 7.8 Hz, 1H), 7.87 (t, J = 7.8 Hz, 1H), 8.10 (d, J = 7.8 Hz, 1H), 8.15 (d, J = 7.8 Hz, 1H) |
| VIII-1006 | 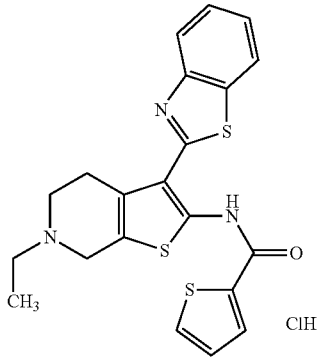 [SMILES: CCN1CCc2c(sc(NC(=O)c3cccs3)c2-c2nc3ccccc3s2)C1 ; Cl] | $^1$H NMR (TFAA, 400 MHz) δ: 1.65 (t, J = 6.9 Hz, 3H), 3.22-3.38 (m, 1H), 3.42-3.78 (m, 4H), 4.03-4.07 (m, 1H), 4.50 (d, J = 15 Hz, 1H), 4.96 (d, J = 15 Hz, 1H), 7.23 (br s, 1H), 7.76-8.40 (m, 4H), 8.17-8.31 (m, 2H) |
| VIII-1007 | 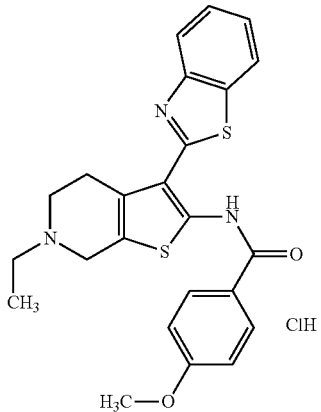 [SMILES: CCN1CCc2c(sc(NC(=O)c3ccc(OC)cc3)c2-c2nc3ccccc3s2)C1 ; Cl] | $^1$H NMR (DMSO, 400 MHz) δ: 1.42 (t, J = 6.8 Hz, 3H), 3.00-3.55 (m, 3H), 3.78-3.88 (m, 1H), 3.95 (s, 3H), 4.27-4.40 (m, 1H), 4.58-4.73 (m, 1H), 7.26 (d, J = 8.5 Hz, 2H), 7.51 (t, J = 7.8 Hz, 1H), 7.64 (t, J = 7.8 Hz, 1H), 8.09 (d, J = 8.5 Hz, 2H), 8.12-8.20 (m, 2H), 11.20 (br s, 1H), 13.95 (s, 1H) |

TABLE 10-continued
Spectral data for compounds of the general formula VIII.
| № | Formula | $^1$H NMR, DMSO-d6, δ, ppm; LCMS, m/z (M + 1) |
|---|---------|----------------------------------------------|
| VIII-1008 | 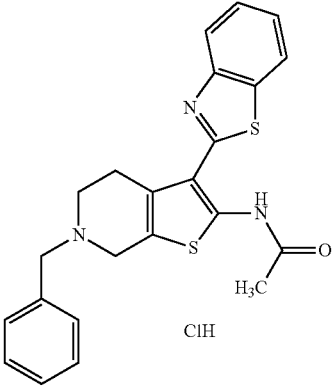 [SMILES: CC(=O)Nc1sc2c(c1-c1nc3ccccc3s1)CCN(Cc1ccccc1)C2 ; Cl] | $^1$H NMR (TFAA, 400 MHz) δ: 2.25 (s, 3H), 3.04-3.13 (m, 1H), 3.30-3.61 (m, 2H), 3.97-4.09 (m, 1H), 4.30-4.72 (m, 4H), 7.40-7.53 (m, 5H), 7.76-7.90 (m, 2H), 8.10-8.16 (m, 2H) |
| VIII-1009 | 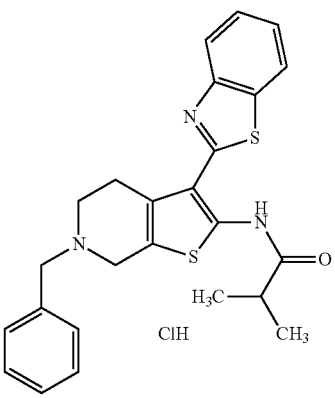 [SMILES: CC(C)C(=O)Nc1sc2c(c1-c1nc3ccccc3s1)CCN(Cc1ccccc1)C2 ; Cl] | $^1$H NMR (DMSO, 400 MHz) δ: 1.20 (d, J = 6.6 Hz, 6H), 2.86 (s, J = 6.6 Hz, 1H), 3.20-3.48 (m, 3H), 3.62-3.84 (m, 1H), 4.20-4.37 (m, 2H), 4.40-4.59 (m, 2H), 7.45-7.52 (m, 4H), 7.63 (t, J = 7.8 Hz, 1H), 7.64-7.71 (m, 2H), 8.05 (d, 7.8 Hz, 1H), 8.18 (d, 7.8 Hz, 1H), 11.69 (br s, 1H), 12.90 (br s, 1H) |
| VIII-1010 | 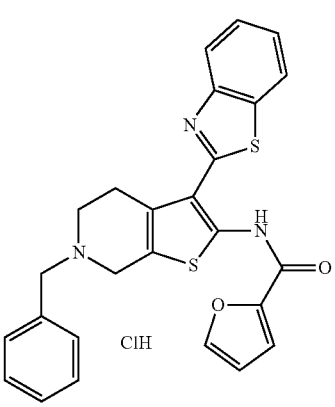 [SMILES: O=C(Nc1sc2c(c1-c1nc3ccccc3s1)CCN(Cc1ccccc1)C2)c1ccco1 ; Cl] | $^1$H NMR (DMSO, 400 MHz) δ: 3.20-3.30 (m, 1H), 3.61-3.75 (m, 2H), 4.15-4.25 (m, 1H), 4.51 (d, J = 15 Hz, 1H), 4.60 (d, J = 12 Hz, 1H), 4.70 (d, J = 15 Hz, 1H), 4.80 (d, J = 12 Hz, 1H), 6.70 (s, 1H), 7.50-7.66 (m, 7H), 7.92 (t, J = 7.8 Hz, 1H), 7.99 (t, J = 7.8 Hz, 1H), 8.22-8.30 (m, 2H), 11.69 (br s, 1H), 12.90 (s, 1H) |

TABLE 10-continued

Spectral data for compounds of the general formula VIII.

| № | Formula | $^1$H NMR, DMSO-d6, δ, ppm;<br>LCMS, m/z (M + 1) |
|---|---------|---------------------------------------------------|
| VIII-1011 | 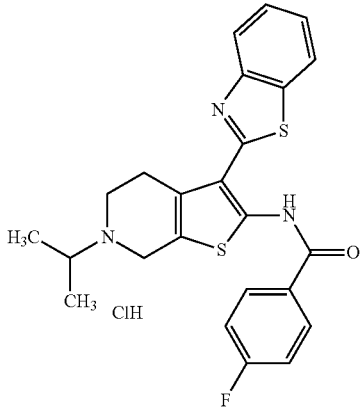 [SMILES: CC(C)N1CCc2c(sc(NC(=O)c3ccc(F)cc3)c2-c2nc3ccccc3s2)C1 ; Cl] | $^1$H NMR (TFAA, 400 MHz) δ: 1.50-1.70 (m, 6H), 3.22-3.35 (m, 1H), 3.39-3.50 (m, 1H), 3.58-3.70 (m, 1H), 3.95-4.09 (m, 2H), 4.51 (d, J = 13 Hz, 1H), 4.68 (d, J = 13 Hz, 1H), 7.22 (t, J = 8.4 Hz, 2H), 7.86-8.10 (m, 4H), 8.19 (d, J = 8.0 Hz, 1H), 8.25 (d, J = 8.0 Hz, 1H) |
| VIII-1012 | 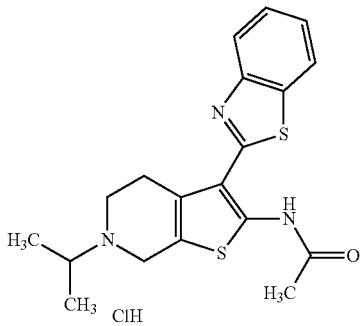 [SMILES: CC(=O)Nc1sc2c(c1-c1nc3ccccc3s1)CCN(C(C)C)C2 ; Cl] | $^1$H NMR (DMSO, 400 MHz) δ: 1.45-1.63 (m, 6H), 2.37 (s, 3H), 3.23-3.39 (m, 3H), 3.62-3.72 (m, 1H), 3.77-3.87 (m, 1H), 4.34-4.56 (m, 2H), 7.52 (t, J = 7.8 Hz, 1H), 7.63 (t, J = 7.8 Hz, 1H), 8.17-8.23 (m, 2H), 11.03 (br s, 1H), 12.54 (s, 1H) |
| VIII-1013 | 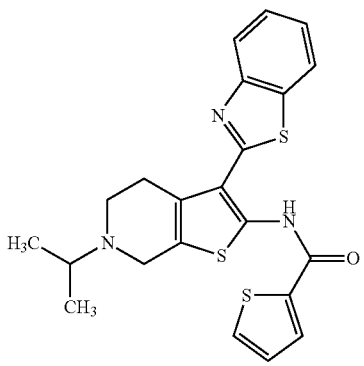 [SMILES: CC(C)N1CCc2c(sc(NC(=O)c3cccs3)c2-c2nc3ccccc3s2)C1] | $^1$H NMR (TFAA, 400 MHz) δ: 1.50-1.70 (m, 6H), 3.30 (d, J = 15 Hz, 1H), 3.49-3.80 (m, 2H), 3.89-4.13 (m, 3H), 4.51-4.67 (m, 1H), 4.80 (d, J = 15 Hz, 1H), 7.24 (t, J = 5.4 Hz, 1H), 7.78-8.05 (m, 4H), 8.22-8.36 (m, 3H) |
| VIII-1014 | 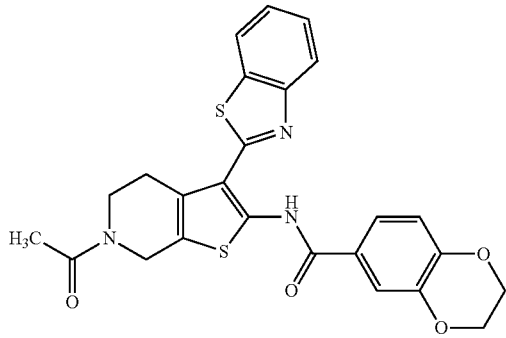 [SMILES: CC(=O)N1CCc2c(sc(NC(=O)c3ccc4c(c3)OCCO4)c2-c2nc3ccccc3s2)C1] | $^1$H NMR (TFAA, 400 MHz) δ: 2.70 (s, 3H), 3.06-3.27 (m, 2H), 4.12-4.52 (m, 6H), 5.07-5.22 (m, 2H), 7.08 (d, J = 8.0 Hz, 1H), 7.47-7.56 (m, 2H), 7.91 (t, J = 7.8 Hz, 1H), 7.97 (t, J = 7.8 Hz, 1H), 8.20 (d, J = 7.8 Hz, 1H), 8.25 (d, J = J = 7.8 Hz, 1H) |

TABLE 10-continued

Spectral data for compounds of the general formula VIII.

| №  | Formula | $^1$H NMR, DMSO-d6, δ, ppm; LCMS, m/z (M + 1) |
|---|---|---|
| VIII-1015 | | $^1$H NMR (TFAA, 400 MHz) δ: 2.70 (s, 3H), 3.05-3.26 (m, 2H), 4.15-4.34 (m, 2H), 5.05-5.25 (m, 2H), 6.72 (s, 1H), 7.52 (br s, 1H), 7.65 (s, 1H), 7.91 (t, J = 7.8 Hz, 1H), 7.98 (t, J = 7.8 Hz, 1H), 8.21 (d, J = 7.8 Hz, 1H), 8.25 (d, J=7.8 Hz, 1H) |
| VIII-1016 | | $^1$H NMR (TFAA, 400 MHz) δ: 1.15-1.42 (m, 3H), 1.42-1.60 (m, 2H), 1.70-2.04 (m, 5H), 2.43-2.57 (m, 1H), 2.67 (s, 3H), 2.97-3.20 (m, 2H), 4.00-4.31 (m, 2H), 4.95-5.17 (m, 2H), 7.85-8.03 (m, 2H), 8.17-8.28 (m, 2H) |
| VIII-1017 | | $^1$H NMR (DMSO, 300 MHz) δ: 2.00-2.15 (m, 3H), 2.82-3.02 (m, 2H), 3.70-3.84 (m, 2H), 3.95 (s, 2H), 4.56-4.69 (m, 2H), 7.28-7.57 (m, 7H), 7.81 (d, J = 8.0 Hz, 1H), 8.02 (d, J = 8.0 Hz, 1H), 12.55-12.62 (m, 1H) |
| VIII-1018 | | $^1$H NMR (DMSO, 300 MHz) δ: 2.00-2.20 (m, 3H), 2.88-3.07 (m, 2H), 3.73-3.90 (m, 2H), 4.56-4.70 (m, 2H), 7.35-7.45 (m, 1H), 7.52-7.60 (m, 1H), 7.96-8.08 (m, 2H), 8.15-8.23 (m, 1H), 8.32-8.39 (m, 1H), 8.82 (s, 1H), 13.99-14.05 (m, 1H) |

TABLE 10-continued

Spectral data for compounds of the general formula VIII.

| № | Formula | ¹H NMR, DMSO-d6, δ, ppm; LCMS, m/z (M + 1) |
|---|---|---|
| VIII-1019 | | ¹H NMR (DMSO, 400 MHz) δ: 2.03-2.14 (m, 3H), 2.86-3.03 (m, 2H), 3.72-3.82 (m, 2H), 4.03 (s, 2H), 4.56-4.67 (m, 2H), 6.99 (t, J = 8.2 Hz, 2H), 7.38-7.48 (m, 3H), 7.54 (t, J = 7.6 Hz, 1H), 8.05 (t, J = 8.2 Hz, 2H), 13.60-13.69 (m, 1H) |
| VIII-1020 | | ¹H NMR (DMSO, 400 MHz) δ: 1.28 (t, J = 6.9 Hz, 3H), 2.29 (s, 3H), 2.95 (br s, 2H), 3.75 (br s, 2H), 4.12 (q, J = 6.9 Hz, 2H), 4.55 (br s, 2H), 7.40 (t, J = 7.8 Hz, 1H), 7.52 (t, J = 7.8 Hz, 1H), 7.96-8.04 (m, 2H), 12.70 (s, 1H) |
| VIII-1021 | | ¹H NMR (DMSO, 400 MHz) δ: 1.25 (t, J=6.9 Hz, 3H), 2.96 (br s, 2H), 3.78 (br s, 2H), 3.92 (s, 3H), 4.12 (q, J = 6.9 Hz, 2H), 4.55 (br s, 2H), 7.17 (d, J = 8.6 Hz, 2H), 7.42 (t, J = 7.8 Hz, 1H), 7.57 (t, J = 7.8 Hz, 1H), 7.96-8.10 (m, 4H), 13.85 (s, 1H) |
| VIII-1022 | | ¹H NMR (DMSO, 400 MHz) δ: 1.15-1.23 (m, 6H), 2.59 (q, J = 7.0 Hz, 2H), 2.97 (br s, 2H), 3.75 (br s, 2H), 4.11 (q, J = 6.8 Hz, 2H), 4.65 (br s, 2H), 7.38 (t, J = 8.0 Hz, 1H), 7.50 (t, J = 8.0 Hz, 1H), 7.92-8.04 (m, 2H), 12.85 (s, 1H) |

TABLE 10-continued
Spectral data for compounds of the general formula VIII.
| № | Formula | $^1$H NMR, DMSO-d6, δ, ppm; LCMS, m/z (M + 1) |
|---|---------|------------------------------------------------|
| VIII-1023 | 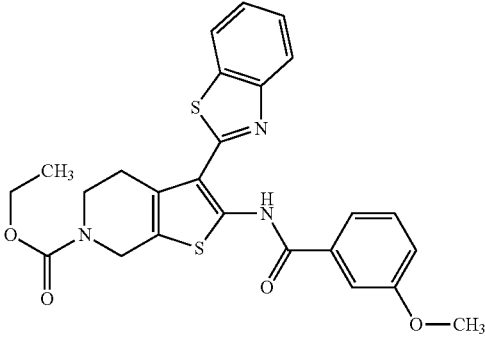 [SMILES: CCOC(=O)N1CCc2c(sc(NC(=O)c3cccc(OC)c3)c2-c2nc3ccccc3s2)C1] | $^1$H NMR (DMSO, 400 MHz) δ: 1.30 (t, J = 6.9 Hz, 3H), 3.03 (br s, 2H), 3.82 (br s, 2H), 3.96 (s, 3H), 4.16 (q, J = 6.9 Hz, 2H), 4.64 (br s, 2H), 7.28 (d, J = 8.3 Hz, 1H), 7.48 (t, J = 7.8 Hz, 1H), 7.58-7.72 (m, 4H), 8.04 (d, 7.8 Hz, 1H), 8.09 (d, 7.8 Hz, 1H), 13.98 (s, 1H) |
| VIII-1024 | 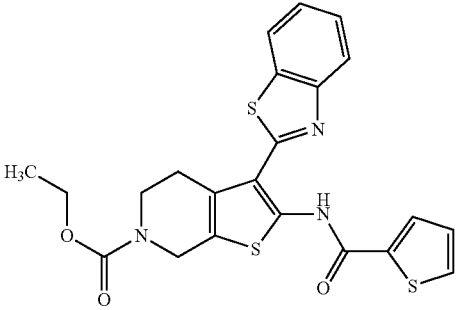 [SMILES: CCOC(=O)N1CCc2c(sc(NC(=O)c3cccs3)c2-c2nc3ccccc3s2)C1] | $^1$H NMR (DMSO, 400 MHz) δ: 1.30 (t, J = 6.9 Hz, 3H), 2.87 (br s, 2H), 3.73 (br s, 2H), 4.13 (q, J = 6.9 Hz, 2H), 4.53 (br s, 2H), 7.30 (t, J = 5.5 Hz, 1H), 7.39 (t, J = 7.8 Hz, 1H), 7.52 (t, J = 7.8 Hz, 1H), 7.80 (d, J = 5.7 Hz, 1H), 7.91 (d, J = 8.0 Hz, 1H), 7.94-8.04 (m, 2H), 13.73 (s, 1H) |
| VIII-1025 | 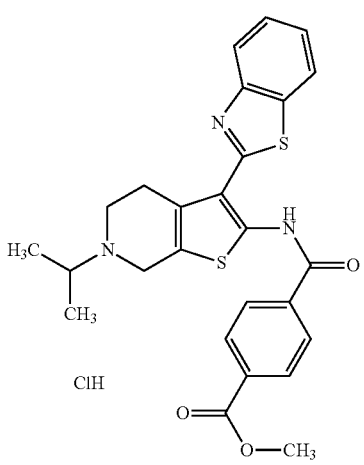 [SMILES: COC(=O)c1ccc(C(=O)Nc2sc3c(c2-c2nc4ccccc4s2)CCN(C(C)C)C3)cc1 ; Cl] | $^1$H NMR (TFAA, 400 MHz) δ: 1.55-1.70 (m, 6H), 3.22-3.35 (m, 1H), 3.39-3.55 (m, 1H), 3.58-3.71 (m, 1H), 3.95-4.07 (m, 2H), 4.11 (s, 3H), 4.61 (d, J = 13 Hz, 1H), 4.80 (d, J = 13 Hz, 1H), 7.87-8.06 (m, 4H), 8.17-8.28 (m, 4H) |

TABLE 10-continued

Spectral data for compounds of the general formula VIII.

| № | Formula | $^1$H NMR, DMSO-d6, δ, ppm; LCMS, m/z (M + 1) |
|---|---|---|
| VIII-1026 | 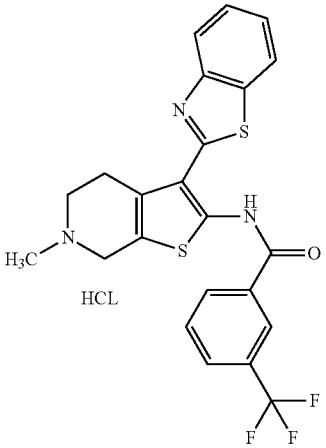 [SMILES: CN1CCc2c(sc(NC(=O)c3cccc(C(F)(F)F)c3)c2-c2nc3ccccc3s2)C1] | $^1$H NMR (TFAA, 400 MHz) δ: 3.10-3.41 (m, 5H), 3.50-3.65 (m, 1H), 3.92-4.02 (m, 1H), 4.45 (d, J = 14 Hz, 1H), 4.81 (d, J = 14 Hz, 1H), 7.62 (t, J = 8.0 Hz, 1H), 7.77-7.92 (m, 3H), 7.98-8.18 (m, 4H) |

EXAMPLE 11

Preparation of Pharmaceutical Composition

According to the invention pharmaceutical composition could be prepared by means of practice conventional in the art and consists in utilization of pharmacologically effective amount of drug substance which is, at least, one of the compounds of the general formulas I-VIII or its pharmaceutically acceptable salt, usually from 5 to 30 weight %, in combination with, at least, one pharmaceutically acceptable supportive additives, such as solvents, diluents, binding agents, distributing agents, adsorbing agents, flavouring agents, gustative agents. In compliance with the usual practice pharmaceutical compositions could be in liquid and solid forms.

Solid drug forms implicate, for example, tablets, gelatin capsules, pills and others.

Liquid drug forms for injections and parenteral introduction include, for example, solutions, emulsion, suspensions and others.

As a rule, pharmaceutical compositions could be prepared using standard procedures, consisting in mixing an active ingredient with liquid or finely grinded solid excipients.

For example, 100 mg of composition comprising 15.0 mg of 2-phenyl-3,4-dimethyl-6-{2-[4-(3-chlorophenyl)piperazin-1-yl]-2-oxoethyl}-2,6-dihydro-7H-pyrazolo[3,4-d]pyridazin-7-one (compound I-1002) includes:

| Compound 17 | 15.0 mg |
|---|---|
| Lactose | 40.0 mg |
| Alginic acid | 20.0 mg |
| Citric acid | 5.0 mg |
| Tragacant | 20.0 mg |

According to the invention pharmaceutical compositions comprising as a drug substance other compounds of the general formulas I-VIII could be prepared in the similar way.

EXAMPLE 12

Preparation of a Medicament in the Form of Tablets 1600 mg of starch, 1600 mg of grained lactose, 400 mg of talcum and 1000 mg of 2-phenyl-3,4-dimethyl-6-{2-[4-(3-chlorophenyl)piperazin-1-yl]-2-oxoethyl}-2,6-dihydro-7H-pyrazolo[3,4-d]pyridazin-7-one (compound I-1002) were mixed carefully and pressed together in a brick. Prepared brick was crushed to granules and riddled through sieves, granules of 14-16 mesh size were gathered. The granules obtained were pelletised in the tablets of suitable form 560 mg by weight each. According to the invention medicaments comprising as an active ingredient other compounds of the general formula I-VIII could be prepared in a similar way.

EXAMPLE 13

Preparation of a Medicament in the Form of Capsules

2-Phenyl-3,4-dimethyl-6-{2-[4-(3-chlorophenyl)piperazin-1-yl]-2-oxoethyl}-2,6-dihydro-7H-pyrazolo[3,4-c]pyridazin-7-one (compound I-1002) was mixed carefully with lactose powder in ratio 2:1. The prepared powdery mixture 300 mg by weight was packed into gelatinous capsules of suitable size.

EXAMPLE 14

Preparation of a Medicament in the Form of Compositions for Intramuscular, Intraperitoneal or Hypodermic Injections 500 mg Of 2-phenyl-3,4-dimethyl-6-{2-[4-(3-chlorophenyl)piperazin-1-yl]-2-oxoethyl}-2,6-dihydro-7H-pyrazolo [3,4-d]pyridazin-7-one (compound I-1002) were mixed with 300 mg of chlorobutanole, 2 ml of propylene glycol and 100 ml of water for injections. The prepared solution was filtered and placed in 1 ml ampoules which were sealed up and sterilized in an autoclave.

EXAMPLE 15

Determination of Acute Toxicity of Compounds of the General Formulas I-VIII

Acute toxicity of compounds of the general formulas I-VIII was determined using white outbread male mice 22-26 gr by weight. The compounds were introduced intraperitoneally in the form of solution or suspension in 1% starch solution. The period of observation was 14 days. Toxicity in the form of $LD_{50}$ was calculated by Litchfild and Wilcoxon method [Litchfild J. T., Wilcoxon F. J., *J. Pharmacol. Exp. Ther.*, 1949, v. 96, pp. 99-114].

As a result it was found that $LD_{50}$ of the investigated compounds varies from 150 up to 1500 mg/kg. In accordance with toxicity classification of chemicals these compounds fall into group of low- and medium-toxic substances.

EXAMPLE 16

Determination of Binding Parameters of Compounds of the General Formulas I-VIII to Smo Receptors, their Pharmacokinetic (PK) Parameters and Maximum Tolerated Doses Oral bioavailability % F of compounds of the general formulas I-VIII was calculated on the basis of experimental results according to the following equation:

$$\% F = [AUC_{0 \to t_n}(PO)/AUC_{0 \to t_n}(IP)] \times 100\%.$$

The parameters obtained (bioavailability % F, half-period of excretion T1/2 and maximum concentration Cmax) show that the compounds of the general formulas I-VIII exhibit a favourable pharmacokinetic profile.

Maximum tolerated dose of compounds was determined in tests on male mice of SHK line by intraperitoneal once daily introduction of the compounds in doses from 30 to 300 mg/kg during 5 days. 8 Mice were used in each group. Weight of mice and also animals' mortality were registered. As a result of the tests it was found that maximum tolerated dose (MTD) for the most part of tested compounds is above 200 mg/kg.

TABLE 11

Parameters of binding to Smo receptors for some compounds of the general formulas I-VIII

| | Compound | | | | | | |
|---|---|---|---|---|---|---|---|
| | III-1029 | III-1017 | III-1011 | I-1001 | VIII-1001 | V-1043 | V-1017 |
| IC50 (bodipy-cyclopamine) nM Mice SHK PK | 259 | ND* | 93 | ND | ND | 69 | 40 |
| % F (PO/IV) | 75 | 19 | 64 | 35 | ND | 3 | 63 |
| T½ (min) | 59 PO | 67 IP, 5 mg/Kg; 55 PO, 5 mg/Kg | 44 IP, 5 mg/Kg; 58 PO, 5 mg/Kg | 125 PO, 5 mg/Kg | 294 IP, 100 mg/Kg | 64 IP, 5 mg/Kg; | 68 IP, 5 mg/Kg; 137 PO, 20 mg/Kg |
| Cmax (mg mg/ml) | 378 IP, 5 mg/Kg 912 PO, 5 mg/Kg; | 357 IP, 5 mg/Kg 398 PO, 5 mg/Kg | 1038 IP, 5 mg/Kg; 564 PO, 5 mg/Kg | 4458 PO, 20 mg/Kg | 45 IP, 100 mg/Kg | 167 IP, 5 mg/Kg 71 PO, 5 mg/Kg | 289 IP, 5 mg/Kg 758 PO, 20 mg/Kg; |
| MTD (mg/kg) | >200 | >200 | >200 | >200 | >100 | >200 | >200 |

*ND - the values were not determined.

Binding parameters to Smo receptors for some of compounds of the general formulas I-VIII are presented in table 11 as the values of half-maximal displacement of cyclopamine labelled with fluorescent dye (bodipy-cyclopamine). The tests were carried out for Smo-HEK cells, comprising artificially expressed protein Smo. The results obtained show that the compounds of the general formulas I-VIII possess high affinity to Smo receptors, which are comparable to the affinity of cyclopamine.

Pharmacokinetic investigations were carried out on mice of BALB/c line. All animals were divided into three groups in a random manner: two experimental groups were used for pharmacokinetic analyses at peroral (PO) and intraperitoneal (IP) ways of substance introduction in various doses, and the control group for getting intact blood plasma.

Blood samples were taken by decapitation of animals before introduction of medicament (control samples), and by decapitation in 5, 15, 30, 60, 120 and 240 minutes after introduction of medicament. Three mice were used for each time interval point.

Analysis of samples comprising compounds of the general formulas I-VIII was carried out by Chromato-Mass-Spectrometry method. The data were analysed by means of software package WinNonLin (Pharsight, CIIIA).

According to the classification of chemical compounds toxicity the investigated compounds may be referred to low-toxic substances.

EXAMPLE 17

Influence of the Compound of the General Formula I-VIII on Induction of Transcriptional Factor Gli1 in Cell Culture Panc1 of Human's Pancreatic Carcinoma Examples of suppression of the transcription factor Gli1 induction in human's tumor cell culture Panc1 by compounds of the general formulas I-VIII are presented in FIG. 2. As a result of tests it was found that at concentration of 20 mkM the compounds III-1029, I-1001 and VII-1001 block effectively Hh-signalling cascade that resulted in fall-off expression of the transcription factor Gli1. This effect could be enhanced at combined action of the tested compound and kinas inhibitor (oncolitic Iressa). For caning out the experiments the tumour cell culture Panc1 was cultivated for 72 hours in the presence of 20 mkM of tested compounds.

Measurements of expression level Gli1 were carried out by determination of HGli mRNA amount according to the method [Lauth M., Bergstrom A., Shimokawa T., Toftgard R.

Inhibition of GLI-mediated transcription and tumor cell growth by small-molecule antagonists. PNAS. 2007, 104(20): 8455-8460].

EXAMPLE 18

Determination of Antitumour Activity of Compounds of the General formulas I-VIII in Xenograft Mice Models In Vivo Example of antitumour activity of compound III-1029 towards human's pancreatic carcinoma model Panc1, implanted to immunodeficient transgenic (naked) mice Balb-c/nude, is presented in FIG. 3. Mice of 8 weeks age which were implanted with pancreatic carcinoma by injection of $4\times10^6$ tumour cells were used in the experiments. Introduction of tested compound (peroral 50 mg/kg, daily during 14 days) was started in 7 days after transplantation of tumour (an average size of tumour was 30-60 mm$^3$). As a result of the tests it was shown that under the said way of introduction compound III-1029 suppresses tumour growth on 67% in comparison with the control group (mice with implanted tumour not treated with compound III-1029).

Example of antitumour activity of compounds III-1017 and III-1011 towards human's pancreatic carcinoma Panc1, implanted to immunodeficient transgenic (naked) mice Balb-c/nude, is presented in FIG. 4. Mice of 8 weeks age which were implanted with pancreatic carcinoma by injection of $4\times10^7$ tumour cells were used in the experiments. Introduction of tested compound (intraperitoneally 100 m mg/kg, daily during 21 days) was started in 8 days after transplantation of tumour (an average size of tumour is 60-140 mm$^3$). As a result of the tests it was shown that under the said way of introduction compounds III-1017 and III-1011 suppress tumour growth on 27 and 46% in comparison with the control group (mice with implanted tumour not treated with the tested compounds).

Thus, the compounds of the general formulas I-VIII exhibit pronounced antitumour activity, determined by suppression of Hh-signalling cascade.

INDUSTRIAL APPLICABILITY

The invention could be used in medicine, veterinary, biochemistry.

The invention claimed is:
1. A compound of a 2,6-dihydro-7H-pyrazolo[3,4-d]pyridazin-7-one of general formula I or a pharmaceutically acceptable salt thereof,

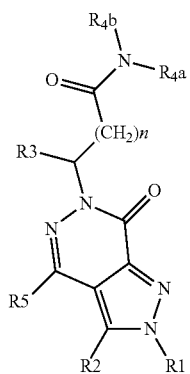

wherein:
n is integer number 0, 1, 2 or 3;
R1 represents H, inert substituent, NH-protective or electrophilic substituent;
R2, R5 represent H or lower alkyl;
R3 represents H or inert substituent;
R4 represents H or inert substituents or R4a and R4b together with the nitrogen atom they are attached to via R4a and R4b may form a substituted azaheterocycle.

2. The compound of claim 1, which is a substituted 2,6-dihydro-7H-pyrazolo[3,4-d]pyridazin-7-one of general formula I-1 or pharmaceutically acceptable salts thereof,

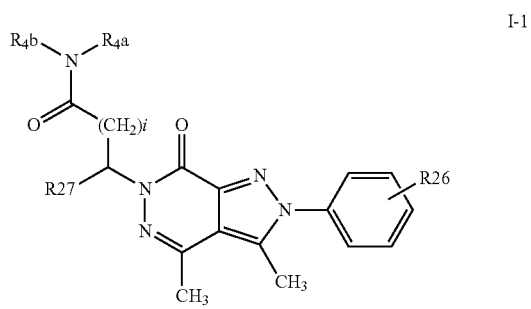

wherein:
R4 is as defined above;
i is integer number 0, 1 or 2;
R26 represents H, halogen, CF$_3$, CF$_3$O, CN, nitro group or inert substituent;
R27 represents H, optionally substituted benzyl, optionally substituted aryl or optionally substituted lower alkyl.

3. A compound selected from the group consisting of
2-Phenyl-3,4-dimethyl-6-{2-[4-(3-methoxyphenyl)piperazin-1-yl]-2-oxoethyl}-2,6-dihydro-7H-pyrazolo[3,4-d]pyridazin-7-one;
2-Phenyl-3,4-dimethyl-6-{2-[4-(3-chlorophenyl)piperazin-1-yl]-2-oxoethyl}-2,6-dihydro-7H-pyrazolo[3,4-d]pyridazin-7-one;
2-Phenyl-3,4-dimethyl-6-{2-[4-phenylpiperazin-1-yl]-2-oxoethyl}-2,6-dihydro-7H-pyrazolo[3,4-d]pyridazin-7-one;
2-Phenyl-3,4-dimethyl-6-{2-[4-(2,3-dimethylphenyl)piperazin-1-yl]-2-oxoethyl}-2,6-dihydro-7H-pyrazolo[3,4-d]pyridazin-7-one;
2-Phenyl-3,4-dimethyl-6-{2-[4-(2,5-dimethylphenyl)piperazin-1-yl]-2-oxoethyl}-2,6-dihydro-7H-pyrazolo[3,4-d]pyridazin-7-one;
2-Phenyl-3,4-dimethyl-6-{2-[4-(4-fluorophenyl)piperazin-1-yl]-2-oxoethyl}-2,6-dihydro-7H-pyrazolo[3,4-d]pyridazin-7-one;
2-Phenyl-3,4-dimethyl-6-{2-[4-(2-fluorophenyl)piperazin-1-yl]-2-oxoethyl}-2,6-dihydro-7H-pyrazolo[3,4-d]pyridazin-7-one;
2-Phenyl-3,4-dimethyl-6-{1-methyl-2-[4-phenylpiperazin-1-yl]-2-oxoethyl}-2,6-dihydro-7H-pyrazolo[3,4-d]pyridazin-7-one;
2-Phenyl-3,4-dimethyl-6-{1-methyl-2-[4-(3-chlorophenyl)piperazin-1-yl]-2-oxoethyl}-2,6-dihydro-7H-pyrazolo[3,4-d]pyridazin-7-one;
2-Phenyl-3,4-dimethyl-6-{1-methyl-2-[4-cyclohexylpiperazin-1-yl]-2-oxoethyl}-2,6-dihydro-7H-pyrazolo[3,4-d]pyridazin-7-one;
2-Phenyl-3,4-dimethyl-6-{1-methyl-2-[4-(2,3-dimethylphenyl)piperazin-1-yl]-2-oxoethyl}-2,6-dihydro-7H-pyrazolo[3,4-d]pyridazin-7-one;
2-Phenyl-3,4-dimethyl-6-{1-methyl-2-[4-benzylpiperazin-1-yl]-2-oxoethyl}-2,6-dihydro-7H-pyrazolo[3,4-d]pyridazin-7-one;

2-Phenyl-3,4-dimethyl-6-{1-methyl-2-[4-(2-fluorophenyl)piperazin-1-yl]-2-oxoethyl}-2,6-dihydro-7H-pyrazolo[3,4-d]pyridazin-7-one;

2-[2-(2,4-dimethylphenyl)-3,4-dimethyl-7-oxo-2,7-dihydro-6H-pyrazolo[3,4-d]pyridazin-6-yl]-N-(2-fluorophenyl)acetamide;

2-Phenyl-3,4-dimethyl-6-[1-(morpholin-4-ylcarbonyl)propyl]-2,6-dihydro-7H-pyrazolo[3,4-d]pyridazin-7-one;

2-[2-(4-Methylphenyl)-3,4-dimethyl-7-oxo-2,7-dihydro-6H-pyrazolo[3,4-d]pyridazin-6-yl]-N-[(5-methylfuran-2-yl)methyl]acetamide;

2-[2-(4-Methylphenyl)-3,4-dimethyl-7-oxo-2,7-dihydro-6H-pyrazolo[3,4-d]pyridazin-6-yl)-N-(2-thien-2-ylethyl)propanamide;

2-[2-(4-Methylphenyl)-3,4-dimethyl-7-oxo-2,7-dihydro-6H-pyrazolo[3,4-c]pyridazin-6-yl]-N-(cyclopropyl)butanamide;

3-(2-Phenyl-3,4-dimethyl-7-oxo-2,7-dihydro-6H-pyrazolo[3,4-d]pyridazin-6-yl)-N-(pyridin-3-ylmethyl)propanamide;

3-(2-Phenyl-3,4-dimethyl-7-oxo-2,7-dihydro-6H-pyrazolo[3,4-d]pyridazin-6-yl)-N-(furan-2-ylmethyl)propanamide;

2-Phenyl-3,4-dimethyl-6-(3-morpholin-4-yl-3-oxopropyl)-2,6-dihydro-7H-pyrazolo[3,4-d]pyridazin-7-one;

3-(2-Phenyl-3,4-dimethyl-7-oxo-2,7-dihydro-6H-pyrazolo[3,4-d]pyridazin-6-yl)-N-(thien-2-ylmethyl)propanamide;

4-[2-(4-Methylphenyl)-3,4-dimethyl-7-oxo-2,7-dihydro-6H-pyrazolo[3,4-d]pyridazin-6-yl]-N-(2-furan-2-ylethyl)butanamide;

2-(4-Methylphenyl)-3,4-dimethyl-6-[4-(4-ethylpiperazin-1-yl)-4-oxobutyl]-2,6-dihydro-7H-pyrazolo[3,4-d]pyridazin-7-one;

2-Phenyl-3,4-dimethyl-6-(4-morpholino-4-yl-4-oxobutyl)-2,6-dihydro-2H-pyrazolo[3,4-d]pyridazin-7-one;

4-(2-Phenyl-3,4-dimethyl-7-oxo-2,7-dihydro-6H-pyrazolo[3,4-d]pyridazin-6-yl)-N-[(1-methylethyl)phenyl]butanamide;

2-(2-Phenyl-3,4-dimethyl-7-oxo-2H-pyrazolo[4,3-d]pyridazin-6-yl)-N-[2-(4-benzylpiperidin-1-yl)ethyl]acetamide;

2-Phenyl-3,4-dimethyl-2H-pyrazolo[4,3-d]pyridazin-6-[2-(4-benzylpiperazin-1-yl)-4-oxoethyl]-7-one;

4-(2-p-Tolyl-3,4-dimethyl-7-oxo-2H-pyrazolo[3,4-d]pyridazin-6-yl)-N-(benzo[d][1,3]-dioxol-5-ylmethyl)butanamide;

2-p-Tolyl-3,4-dimethyl-6-[4-oxo-4-(4-(pyridin-2-yl)piperazin-1-yl)butyl]-2H-pyrazolo[3,4-d]pyridazin-7-one;

and pharmaceutical acceptable salts thereof.

4. A pharmaceutical composition, comprising an effective amount of at least one compound of claim 1 or a pharmaceutically acceptable salt thereof, and an excipient.

5. The pharmaceutical composition of claim 4 in the form of a tablet, a sheath, or an injection placed in pharmaceutically acceptable packing.

* * * * *